(12) United States Patent
Croce et al.

(10) Patent No.: US 9,480,699 B2
(45) Date of Patent: Nov. 1, 2016

(54) COMPOSITIONS AND METHODS FOR THE DIAGNOSIS AND THERAPY OF BCL2-ASSOCIATED CANCERS

(71) Applicant: The Ohio State University Research Foundation, Columbus, OH (US)

(72) Inventors: Carlo M. Croce, Columbus, OH (US); George A. Calin, Pearland, TX (US)

(73) Assignee: The Ohio State University Research Foundation, Columbus, OH (US)

(*) Notice: Subject to any disclaimer, the term of this patent is extended or adjusted under 35 U.S.C. 154(b) by 0 days.

(21) Appl. No.: 14/341,145

(22) Filed: Jul. 25, 2014

(65) Prior Publication Data

US 2014/0335161 A1 Nov. 13, 2014

Related U.S. Application Data

(60) Continuation of application No. 13/918,087, filed on Jun. 14, 2013, now abandoned, which is a division of application No. 11/991,773, filed as application No. PCT/US2006/035100 on Sep. 11, 2006, now Pat. No. 8,481,505.

(60) Provisional application No. 60/716,134, filed on Sep. 12, 2005.

(51) Int. Cl.
*A61K 31/7105* (2006.01)
*C12N 15/113* (2010.01)
*C12Q 1/68* (2006.01)
*A61K 31/713* (2006.01)
*A61K 9/127* (2006.01)
(Continued)

(52) U.S. Cl.
CPC ............ *A61K 31/7105* (2013.01); *A61K 9/127* (2013.01); *A61K 31/713* (2013.01); *A61K 45/06* (2013.01); *A61N 5/10* (2013.01); *C12N 15/1135* (2013.01); *C12Q 1/6886* (2013.01); *C12N 2310/141* (2013.01); *C12N 2310/53* (2013.01); *C12N 2320/31* (2013.01)

(58) Field of Classification Search
USPC ........................................ 514/44 A; 536/24.5
See application file for complete search history.

(56) References Cited

U.S. PATENT DOCUMENTS

2005/0176025 A1* 8/2005 McSwiggen et al. ............ 435/6

FOREIGN PATENT DOCUMENTS

EP             1937280 B1    8/2014
WO    WO 2004/043387   * 11/2003

OTHER PUBLICATIONS

Australian Examination Report No. 1, Application No. AU 2006291165 dated May 17, 2011 [7-28346/OSU-2006-009].

(Continued)

*Primary Examiner* — Terra C Gibbs
(74) *Attorney, Agent, or Firm* — MacMillan, Sobanski & Todd, LLC

(57) ABSTRACT

Provided are methods and compositions for the treatment of cancers associated with overexpression of a BCL2 gene and/or gene product in a subject, and methods and compositions for the improvement of anti-cancer therapy, such as chemotherapy and radiation therapy. Also provided are methods for determining the efficacy of a cancer therapy in a subject, methods for diagnosing cancer, methods for assessing patient prognosis, and methods for inducing apoptosis of a cell.

20 Claims, 6 Drawing Sheets
(3 of 6 Drawing Sheet(s) Filed in Color)

(51) Int. Cl.
   *A61K 45/06*   (2006.01)
   *A61N 5/10*    (2006.01)

(56) References Cited

OTHER PUBLICATIONS

Australian Examination Report No. 2, Application No. AU 2006291165 dated Feb. 13, 2012. [7-28346/OSU-2006-009].
Australian Notice of Acceptance, Application No. AU 2006291165 dated Feb. 27, 2013. [7-28346/OSU-2006-009].
Canadian Office Action, Application No. CA 2,845,251 dated Mar. 6, 2015. [2-55902/OSU-2006-009(CA2)].
Canadian Office Action, Application No. CA 2621441 dated Apr. 8, 2013. [2-28346/OSU-2006-009].
Canadian Patent No. CA 2,621,441 date on which the patent was granted and issued May 20, 2014. [2-28346/OSU-2006-009].
Canadian Response to the Office Action dated Mar. 6, 2015, Application No. CA 2845251 dated Aug. 11, 2015. [2-55902/OSU-2006-009(CA2)].
Claims as Filed in Reply to the Third Chinese Office Action, Application No. CN 200680039776.8 dated Jun. 13, 2012. [55-28346/OSU-2006-009].
English Translation of Japanese Interrogatory, Application No. JP 2008-531200 dated Feb. 13, 2014. [6-28346/OSU-2006-009].
European Examination Report, Application No. EP 14178114.6 dated Sep. 24, 2015. [57-56095/OSU-2006-009(EP2)].
Japanese Notification of Reasons for Rejection, Application No. JP 2013-081761 dated Mar. 10, 2015. [6-54882/OSU-2006-009(JP2)].
Notification of the First Chinese Office Action, Application No. CN 200680039776.8 dated Mar. 10, 2010. [55-28346/OSU-2006-009].
Notification of the First Chinese Office Action, Application No. CN 201210380806.9 dated Nov. 5, 2013. [55-54504/OSU-2006-009(CN2)].
Notification of the Third Chinese Office Action, Application No. CN 201210380806.9 dated Dec. 24, 2014. [55-54504/OSU-2006-009(CN2)].
Faguet, "Chronic Lymphocytic Leukemia: An Updated Review", Journal of Clinical Oncology, 1994, vol. 12, No. 9, pp. 1974-1990.
Johnson, "Treatment of Chronic Lymphocytic Leukemia by Total Body Irradiation Alone and Combined with Chemotherapy", International Journal of Radiation Oncology, Biology, and Physics, 1979, vol. 5, No. 2, pp. 159-164.

* cited by examiner

```
         GAGUAAAGUA          UA           GA    U
5' CCUUG            GCAGCACA    AUGGUUUGUG   UUU \
   GGAAC            CGUCGUGU    UACCGGACGU   AAA  G
        AUAAAAACUC          UA           GG    A
```

FIG. 1A

```
       AG   C              - A        CGUUA      UCUA
5' GUCAGC  UGC  UUAGCAGCAC  GU AAUAUUGG      AGAU       \
   CAGUUG  AUG  AGUCGUCGUG  CA UUAUGACC      UCUA       A
       GA   A              U A        -----      UUAA
```

FIG. 1B

```
                                                    3'M1
                                                  3'M2
Hsa_BCL2:       TATGGAATATCCAATCCTGTGCTGCTATCC
                                 | | | | | | | | |
Hsa_miR-15:            GTGTTTGGTAATACACGACGAT
Hsa_miR-16:            GCGGTTATAAATGCACGACGAT

Mmu_BCL2:       TGGGGAAGCCTGCAGTCTG:GCTGCTAGAA
                                | | | | | | | |
Mmu_miR-15:            GTGTTTGGTAATACACGACGAT
Mmu_miR-16:            GCGGTTATAAATGCACGACGAT
```

COMPOSITIONS AND METHODS FOR THE DIAGNOSIS AND THERAPY OF BCL2-ASSOCIATED CANCERS

CROSS-REFERENCE TO RELATED APPLICATIONS

This is a continuation application of U.S. patent application Ser. No. 13/918,087, filed Jun. 14, 2013, now abandoned, as a divisional application of U.S. patent application Ser. No. 11/991,773, now U.S. Pat. No. 8,481,505, issued Jul. 9, 2013, which entered the US national phase on May 14, 2008, from International Application No. PCT/US2006/0035100, filed Sep. 11, 2006, which claims the benefit of U.S. Provisional Patent Application No. 60/716,134, filed Sep. 12, 2005. The aforementioned applications are incorporated herein by reference for all purposes.

GOVERNMENT SUPPORT

This invention was supported, in whole or in part, by grant numbers P01CA76259, P01CA81534, and P30CA56036 from the National Cancer Institute. The Government has certain rights in this invention.

SEQUENCE LISTING

This application is being filed electronically via the USPTO EFS-WEB server, as authorized and set forth in MPEP§1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows: 604_28346_SeqListing_OSURF-26009.txt, and is 84,884 bytes in size.

FIELD OF THE INVENTION

The invention relates to the diagnosis of cancers, in particular to the diagnosis of BCL2-associated cancers. The invention further encompasses methods and compositions for the treatment of cancers involving overexpression of a BCL2 gene and/or gene product. The invention additionally provides novel methods and compositions for the improvement of anti-cancer therapies, such as chemotherapy and other conventional cancer therapies.

BACKGROUND OF THE INVENTION

MicroRNAs (miRNAs, miRs) are found in over one hundred distinct organisms, including fruit flies, nematodes and humans. miRNAs are believed to be involved in a variety of processes that modulate development in these organisms. The miRNAs are typically processed from 60- to 70-nucleotide foldback RNA precursor structures, which are transcribed from the miRNA gene. The RNA precursor or processed miRNA products are easily detected, and a lack of these molecules can indicate a deletion or loss of function of the corresponding miRNA gene.

Cancers are a significant source of mortality and morbidity in the U.S. and throughout the world. In particular, chronic lymphocytic leukemia ("CLL") and other BCL2-associated cancers (e.g., acute myeloid leukemia, multiple myeloma, melanomas, lymphomas (e.g., follicular lymphoma, large cell lymphoma, non-Hodgkin's lymphoma), carcinomas (e.g., brain carcinoma, breast carcinoma, prostate carcinoma, non-small cell lung carcinoma, renal carcinoma, hepatocellular carcinoma and gastric carcinoma), hematologic malignancies, solid tumors, colorectal cancer, Epstein-Barr virus-associated lymphoproliferative disease) are clinically important neoplastic diseases of adult humans. For example, CLL is the most common form of adult leukemia in the Western world, and the age-adjusted incidence of prostate cancer now surpasses that of all other cancers among men in the United States, and, after lung cancer, is the second leading cause of all male cancer deaths in the country.

Hemizygous and/or homozygous loss at 13q14 occurs in more than half of the reported CLL cases, and constitutes the most frequent chromosomal abnormality in CLL. The karyotyping of tissue samples from CLL patients identified relatively few chromosomal abnormalities, suggesting that the specificity and frequency of observed deletions at 13q14 have pathologic significance. In addition, 13q14 deletions also occur in 60% of prostate cancers, suggesting that one or more tumor suppressor genes located at 13q14 are involved in the pathogenesis of both CLL and prostate cancers.

The presence of both clonal homozygous and heterozygous deletions, and the very high frequency of 13q14 loss in CLL and prostate cancers, indicates that deletions in this region are related to the etiology of certain cancer types. Several groups have used positional cloning in order to identify the gene or genes in the deleted areas. To date, a total of eight genes from the deleted regions of 13q14 in sporadic and familial cases of CLL have been identified and screened for alterations at the DNA and/or RNA level: Leu1 (BCMS or EST70/Leu1), Leu 2 (ALT1 or 1B4/Leu2), Leu 5 (CAR), CLLD6, KPNA3, CLLD7, LOC51131 (putative zinc finger protein NY-REN-34 antigen) and CLLD8. However, detailed genetic analyses, including extensive loss of heterozygosity (LOH), mutation and expression studies, have failed to demonstrate the consistent involvement of any of these genes in carcinogenesis.

The malignant, mostly non-dividing B cells of CLL overexpress Bcl2 protein (Kitada, S., et al., *Blood* 91: 3379-3389 (1998)), an apoptosis inhibitor that plays a central role in promoting survival of eukaryotic cells by inhibiting cell death (Cory, S., and Adams, J. M., *Nature Reviews* 2: 647-656 (2002)). Overexpression of Bcl2 has been associated with many types of human cancers, including leukemias, lymphomas and carcinomas (Sanchez-Beato, M., et al., *Blood* 101: 1220-1235 (2003)). In follicular lymphomas, and in a fraction of diffuse B-cell lymphomas, the mechanism of BCL2 activation was found to be a chromosomal translocation, t(14;18)(q32;q21), which places the BCL2 gene under the control of immunoglobulin heavy chain enhancers, resulting in deregulated expression of the gene (Tsujimoto, Y., et al., *Science* 226: 1097-1099 (1984); Tsujimoto, Y., et al., *Science* 228: 1440-1443 (1985)). However, the BCL2 gene is juxtaposed to immunoglobulin loci in less than 5% of CLL cases (Adachi, M., et al., *J. Exp. Med.* 171: 559-564 (1990)), and the mechanism by which BCL2 is overexpressed in the majority of CLL cancers is unknown.

Current therapies for CLL typically involve chemotherapy, administered alone or in combination with autologous bone marrow transplantation. The chemotherapy agents employed are generally toxic to the patient and cause only partial remissions in a relatively large proportion of patients. Therapies for BCL2-associated cancer therapies can also involve chemotherapy, often following surgical resection of a tumor. However, as with CLL, the curative properties of the chemotherapeutic agents (with or without surgery) are limited.

Treatment with chemotherapy alone is limited in that cancer cells often become resistant to a broad spectrum of structurally unrelated chemotherapeutic agents. Such resistance, termed "multidrug resistance" (MDR), is a common problem in the treatment of patients with cancer, and the resistance of tumor cells to chemotherapeutic drugs represents a major problem in clinical oncology.

Apoptosis is an important component of the sequence of events during which chemotherapeutic drugs induce an antitumor response, and studies have implicated Bcl2 as having a critical role in anticancer drug-induced apoptosis (Kim, R et al., *Cancer* 101(11): 2491-2502 (2004)). Furthermore, tumor cells engineered to overexpress Bcl2 develop resistance to the cytotoxic effects of a number of different drugs (Kamesaki et al., Cancer Res. 53: 4251-4256 (1993); Miyashita and Reed, *Blood* 81: 151-157 (1993)).

There is a need for a rapid, economical and accurate diagnostic test for CLL and other BCL2-associated cancers. There is also a need for an economical and effective treatment for BCL2-associated cancers, such as CLL, which does not have a significant negative impact on the patient. There is a further need for new anti-cancer therapies that are directed to inhibiting expression of Bcl2, given that a wide variety of common cancers are associated with Bcl2 protein overexpression. In addition, there is a need for improved anti-cancer therapies that display increased efficacy relative to other conventional anti-cancer treatments. Furthermore, there is a need to identify agents and methods that can increase the sensitivity of cancer cells to the cytotoxic effects of anti-cancer agents, thereby improving cancer therapies. There is also a need for methods of inducing apoptosis in a cell that overexpresses an anti-apoptotic protein, such as Bcl2.

SUMMARY OF THE INVENTION

It has now been discovered that certain microRNAs with sequences that are complementary to nucleotide sequences in the BCL2 gene transcript are deregulated in cancer cells that overexpress Bcl2 protein.

Accordingly, embodiments of the invention provide methods of preventing a cancer or treating a cancer associated with overexpression of a BCL2 gene or gene product (e.g., RNA, protein) in a subject in need of such treatment, comprising administering an effective amount of at least one miR gene product. As used herein, the term "BCL2" refers to a BCL2 nucleic acid (e.g., a BCL2 gene, cDNA, RNA transcript, DNA construct), while "Bcl2" refers to the Bcl2 protein product. In a particular embodiment, the at least one miR gene product comprises a nucleotide sequence that is complementary to a nucleotide sequence in a BCL2 gene transcript. In a particular embodiment, the at least one miR gene product comprises a nucleotide sequence that is complementary to nucleotides 3741 to 3749 of SEQ ID NO: 55. Examples of such miR gene products include, but are not limited to, miR15, miR16, miR-15b and miR-16-2. The miR15 and miR16 genes are localized at 13q14 and are commonly referred to as mir-15a and miR-16-1, respectively. As used herein, the terms "miR15" and "miR-15a" are interchangeable, as are the terms "miR16" and "miR-16-1". In a further embodiment, the miR gene product is selected from the group consisting of miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186, and combinations thereof. In another embodiment, the miR gene product is selected from the group consisting of miR-182, miR-181, miR-30, miR-15a, miR-16-1, miR-15b, miR-16-2, miR-195 and combinations thereof. In a particular embodiment, the miR gene product is not miR-15a or miR-16-1.

Embodiments of the invention further provide a pharmaceutical composition for treating a subject having a cancer associated with Bcl2 overexpression, comprising at least one chemotherapeutic agent and at least one miR gene product, wherein the at least one miR gene product comprises a nucleotide sequence that is complementary to a nucleotide sequence in a BCL2 gene transcript. In one embodiment, the at least one miR gene product is miR-15a. In another embodiment, the at least one miR gene product is miR-16-1. In yet another embodiment, the at least one miR gene product is selected from the group consisting of miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186, and combinations thereof. In another embodiment, the miR gene product is selected from the group consisting of miR-182, miR-181, miR-30, miR-15a, miR-16-1, miR-15b, miR-16-2, miR-195 and combinations thereof. In a particular embodiment, the miR gene product is not miR-15a or miR-16-1.

Embodiments of the invention also encompass methods for determining the efficacy of a cancer therapy in a subject who has a BCL2-associated cancer, comprising administering at least one agent to the subject, and subsequently measuring the expression of a miR gene product that comprises a nucleotide sequence that is complementary to a nucleotide sequence in a BCL2 gene transcript. In a particular embodiment, an increase in the expression of the miR gene product following administration of the agent is indicative of successful treatment. In one embodiment, the at least one miR gene product is miR-15a. In another embodiment, the at least one miR gene product is miR-16-1. In yet another embodiment, the at least one miR gene product is selected from the group consisting of miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186, and combinations thereof. In another embodiment, the miR gene product is selected from the group consisting of miR-182, miR-181, miR-30, miR-15a, miR-16-1, miR-15b, miR-16-2, miR-195 and combinations thereof. In a particular embodiment, the miR gene product is not miR-15a or miR-16-1.

Embodiments of the invention additionally provide methods for increasing the efficacy of anti-cancer treatments (e.g., chemotherapy, radiation therapy) comprising providing at least one miR gene product to a tumor cell, in combination with at least one anti-cancer treatment. In a particular embodiment, the at least one miR gene product comprises a nucleotide sequence that is complementary to a nucleotide sequence in a BCL2 gene transcript. In a further embodiment, the at least one miR gene product is miR-15a or miR-16-1. In yet another embodiment, the at least one miR gene product is selected from the group consisting of miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186, and combinations thereof. In another embodiment, the miR gene product is selected from the group consisting of miR-182, miR-181, miR-30, miR-15a, miR-16-1, miR-15b, miR-16-2, miR-195 and combinations thereof. In a certain embodiment, the miR gene product is not miR-15a or miR-16-1.

Embodiments of the invention provide a method for increasing the sensitivity of a cancer cell to the cytotoxic effects of an anti-cancer agent, comprising providing at least one miR gene product to the cancer cell, wherein the at least one miR gene product comprises a nucleotide sequence that is complementary to a nucleotide sequence in a BCL2 gene transcript. In one embodiment, the at least one miR gene product is miR-15a or miR-16-1. In another embodiment, the at least one miR gene product is selected from the group consisting of miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186, and combinations thereof. In another embodiment, the miR gene product is selected from the group consisting of miR-182, miR-181, miR-30, miR-15a, miR-16-1, miR-15b, miR-16-2, miR-195 and combinations thereof. In a certain embodiment, the miR gene product is not miR-15a or miR-16-1. In a particular embodiment, the anti-cancer agent is a chemotherapeutic agent. In another embodiment, the anti-cancer agent is radiation treatment.

Embodiments of the invention also encompass methods of inducing apoptosis of a cell, comprising contacting a cell with at least one miR gene product that comprises a nucleotide sequence that is complementary to a nucleotide sequence in a BCL2 gene transcript. In a particular embodiment, the miR gene product comprises a nucleotide sequence that is complementary to nucleotides 3741-3749 of SEQ ID NO:55. In a further embodiment, the at least one miR gene product is miR-15a or miR-16-1. In yet another embodiment, the at least one miR gene product is selected from the group consisting of miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186, and combinations thereof. In another embodiment, the miR gene product is selected from the group consisting of miR-182, miR-181, miR-30, miR-15a, miR-16-1, miR-15b, miR-16-2, miR-195 and combinations thereof. In a certain embodiment, the miR gene product is not miR-15a or miR-16-1. Suitable cells for these methods include, but are not limited to, cancer cells and other cells that express Bcl2 protein.

Embodiments of the invention additionally provide a method of diagnosing a BCL2-associated cancer in a subject, comprising determining the level of at least one miR gene product in a sample from the subject, relative to the level of a corresponding miR gene product in a control sample, wherein the miR gene product comprises a nucleotide sequence that is complementary to a nucleotide sequence in a BCL2 gene transcript. In a particular embodiment, the miR gene product comprises a nucleotide sequence that is complementary to nucleotides 3741-3749 of SEQ ID NO:55. In a further embodiment, the at least one miR gene product is miR-15a or miR-16-1. In yet another embodiment, the at least one miR gene product is selected from the group consisting of miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186, and combinations thereof. In another embodiment, the miR gene product is selected from the group consisting of miR-182, miR-181, miR-30, miR-15a, miR-16-1, miR-15b, miR-16-2, miR-195 and combinations thereof. In a certain embodiment, the miR gene product is not miR-15a or miR-16-1.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A and 1B are schematic representations of the predicted secondary structure of the miR-15 [SEQ ID NO:1] and miR-16 [SEQ ID NO:2] precursor RNA, respectively. The RNA secondary structure prediction was performed using the "mfold" program, version 3.1 of Matthews, et al., *J. Mol. Biol.* 288:911-940 (1999), and manually refined to accommodate G/U wobble base pairs in the helical segments. The sequence of the processed miR-15 and miR-16 miRNA is underlined. Adapted from Lagos-Quintana, et al., *Science* 294:853-858 (2001).

Figures 2A, 2B, 2C, 2D:
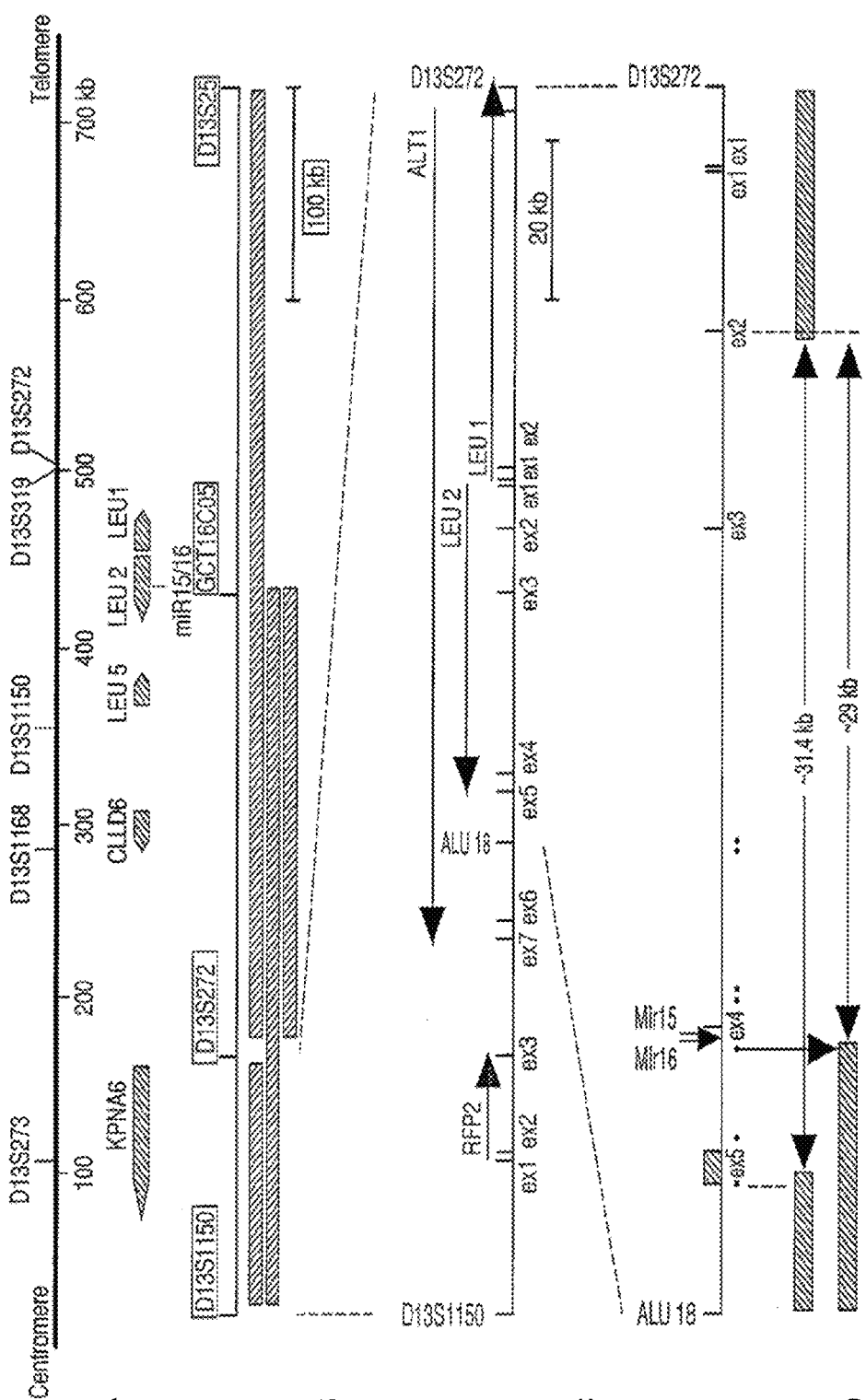
FIG. 2A is a map of genes within the 13q14 tumor suppressor locus in CLL showing the localization of the miR15/16 gene cluster. The position of genetic markers and the position of genes on the map are shown.
FIG. 2B is a map of previously reported 13q14 deletions, marked by horizontally striped boxes.
FIG. 2C is a map of the locus between the D13S1150 and D13S272 markers. The orientation of each gene in this locus is marked by an arrow under the gene name, and vertical bars mark the position of corresponding exons for each gene.
FIG. 2D is a map of the locus between the Alu 18 and D13S272 markers. Bars and boxes mark the position of exons for LEU2/ALT1 and LEU1. The short vertical arrows mark the position of miR15 and miR16 genes. Circles mark the position of PCR primers used to screen somatic cell hybrid clones derived from a fusion of two independent leukemia cases (CLL-A and CLL-B). Hatched boxes represent portions of chromosome 13 present in the hybrids. "←~31.4 kb→" indicates an approximately 31.4 kb deleted region in clone CLL-A, which was derived from a patient with CLL carrying a t(2;13)(q12;q13) translocation, bilateral retinoblastoma, and ulcerative colitis. The long vertical arrow represents the position of the breakpoint in clone CLL-B carrying a t(2;13)(q32;q14) translocation, and "←~29 kb→" indicates an approximately 29 kb deleted region from this CLL clone.

The foregoing and other objects, features and advantages of the invention will be apparent from the following more particular description of the invention.

DETAILED DESCRIPTION OF THE INVENTION

While this invention has been particularly shown and described with references to preferred embodiments thereof, it will be understood by those skilled in the art that various changes in form and details may be made therein without departing from the scope of the invention encompassed by the appended claims.

As used herein interchangeably, a "miR gene product," "microRNA," "miR," or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor.

The sequences of a large number of miR gene products are provided in Table 1. All nucleic acid sequences herein are given in the 5' to 3' direction.

TABLE 1

Human miR Gene Product Sequences

| Name | Precursor Sequence (5' to 3')* | SEQ ID NO: |
|---|---|---|
| let-7a-1-prec | CACTGTGGGATGAGGTAGTAGGTTGTATAGTTTTAGGGTCACACCCACCACTGGGAGATAACTATACAATCTACTGTCTTTCCTAACGTG | 63 |
| let-7a-2-prec | AGGTTGAGGTAGTAGGTTGTATAGTTTAGAATTACATCAAGGGAGATAACTGTACAGCCTCCTAGCTTTCCT | 64 |
| let-7a-3-prec | GGGTGAGGTAGTAGGTTGTATAGTTTGGGGCTCTGCCCTGCTATGGGATAACTATACAATCTACTGTCTTTCCT | 65 |

TABLE 1 -continued

Human miR Gene Product Sequences

| Name | Precursor Sequence (5' to 3')* | SEQ ID NO: |
|---|---|---|
| let-7a-4-prec | GTGACTGCATGCTCCCAGGTTGAGGTAGTAGGTTGTATAG TTTAGAATTACACAAGGGAGATAACTGTACAGCCTCCTAG CTTTCCTTGGGTCTTGCACTAAACAAC | 66 |
| let-7b-prec | GGCGGGGTGAGGTAGTAGGTTGTGTGGTTTCAGGGCAGTG ATGTTGCCCCTCGGAAGATAACTATACAACCTACTGCCTT CCCTG | 67 |
| let-7c-prec | GCATCCGGGTTGAGGTAGTAGGTTGTATGGTTTAGAGTTA CACCCTGGGAGTTAACTGTACAACCTTCTAGCTTTCCTTGG AGC | 68 |
| let-7d-prec | CCTAGGAAGAGGTAGTAGGTTGCATAGTTTTAGGGCAGGG ATTTTGCCCACAAGGAGGTAACTATACGACCTGCTGCCTT TCTTAGG | 69 |
| let-7d-v1-prec | CTAGGAAGAGGTAGTAGTTTGCATAGTTTTAGGGCAAAGA TTTTGCCCACAAGTAGTTAGCTATACGACCTGCAGCCTTTT GTAG | 70 |
| let-7d-v2-prec | CTGGCTGAGGTAGTAGTTTGTGCTGTTGGTCGGGTTGTGA CATTGCCCGCTGTGGAGATAACTGCGCAAGCTACTGCCTT GCTAG | 71 |
| let-7e-prec | CCCGGGCTGAGGTAGGAGGTTGTATAGTTGAGGAGGACA CCCAAGGAGATCACTATACGGCCTCCTAGCTTTCCCCAGG | 72 |
| let-7f-1-prec | TCAGAGTGAGGTAGTAGATTGTATAGTTGTGGGGTAGTGA TTTTACCCTGTTCAGGAGATAACTATACAATCTATTGCCTT CCCTGA | 73 |
| let-7f-2-prec-1 | CTGTGGGATGAGGTAGTAGATTGTATAGTTGTGGGGTAGT GATTTTACCCTGTTCAGGAGATAACTATACAATCTATTGCC TTCCCTGA | 74 |
| let-7f-2-prec-2 | CTGTGGGATGAGGTAGTAGATTGTATAGTTTTAGGGTCAT ACCCCATCTTGGAGATAACTATACAGTCTACTGTCTTTCCC ACGG | 75 |
| let-7g-prec | TTGCCTGATTCCAGGCTGAGGTAGTAGTTTGTACAGTTTGA GGGTCTATGATACCACCCGGTACAGGAGATAACTGTACAG GCCACTGCCTTGCCAGGAACAGCGCGC | 76 |
| let-7i-prec | CTGGCTGAGGTAGTAGTTTGTGCTGTTGGTCGGGTTGTGA CATTGCCCGCTGTGGAGATAACTGCGCAAGCTACTGCCTT GCTAG | 77 |
| mir-001b-1-prec-1 | ACCTACTCAGAGTACATACTTCTTTATGTACCCATATGAAC ATACAATGCTATGGAATGTAAAGAAGTATGTATTTTTGGT AGGC | 78 |
| mir-001b-1-prec-2 | CAGCTAACAACTTAGTAATACCTACTCAGAGTACATACTT CTTTATGTACCCATATGAACATACAATGCTATGGAATGTA AAGAAGTATGTATTTTTGGTAGGCAATA | 79 |
| mir-001b-2-prec | GCCTGCTTGGGAAACATACTTCTTTATATGCCCATATGGAC CTGCTAAGCTATGGAATGTAAAGAAGTATGTATCTCAGGC CGGG | 80 |
| mir-001b-prec | TGGGAAACATACTTCTTTATATGCCCATATGGACCTGCTA AGCTATGGAATGTAAAGAAGTATGTATCTCA | 81 |
| mir-001d-prec | ACCTACTCAGAGTACATACTTCTTTATGTACCCATATGAAC ATACAATGCTATGGAATGTAAAGAAGTATGTATTTTTGGT AGGC | 82 |
| mir-007-1 | TGGATGTTGGCCTAGTTCTGTGTGGAAGACTAGTGATTTTG TTGTTTTTAGATAACTAAATCGACAACAAATCACAGTCTG CCATATGGCACAGGCCATGCCTCTACA | 83 |
| mir-007-1-prec | TTGGATGTTGGCCTAGTTCTGTGTGGAAGACTAGTGATTTT GTTGTTTTTAGATAACTAAATCGACAACAAATCACAGTCT GCCATATGGCACAGGCCATGCCTCTACAG | 84 |

TABLE 1 -continued

Human miR Gene Product Sequences

| Name | Precursor Sequence (5' to 3')* | SEQ ID NO: |
|---|---|---|
| mir-007-2-prec | CTGGATACAGAGTGGACCGGCTGGCCCCATCTGGAAGACT AGTGATTTTGTTGTTGTCTTACTGCGCTCAACAACAAATCC CAGTCTACCTAATGGTGCCAGCCATCGCA | 85 |
| mir-007-3-prec | AGATTAGAGTGGCTGTGGTCTAGTGCTGTGTGGAAGACTA GTGATTTTGTTGTTCTGATGTACTACGACAACAAGTCACA GCCGGCCTCATAGCGCAGACTCCCTTCGAC | 86 |
| mir-009-1 | CGGGGTTGGTTGTTATCTTTGGTTATCTAGCTGTATGAGTG GTGTGGAGTCTTCATAAAGCTAGATAACCGAAAGTAAAAA TAACCCCA | 87 |
| mir-009-2 | GGAAGCGAGTTGTTATCTTTGGTTATCTAGCTGTATGAGTG TATTGGTCTTCATAAAGCTAGATAACCGAAAGTAAAAACT CCTTCA | 88 |
| mir-009-3 | GGAGGCCCGTTTCTCTCTTTGGTTATCTAGCTGTATGAGTG CCACAGAGCCGTCATAAAGCTAGATAACCGAAAGTAGAA ATGATTCTCA | 89 |
| mir-010a-prec | GATCTGTCTGTCTTCTGTATATACCCTGTAGATCCGAATTT GTGTAAGGAATTTTGTGGTCACAAATTCGTATCTAGGGGA ATATGTAGTTGACATAAACACTCCGCTCT | 90 |
| mir-010b-prec | CCAGAGGTTGTAACGTTGTCTATATATACCCTGTAGAACC GAATTTGTGTGGTATCCGTATAGTCACAGATTCGATTCTAG GGGAATATATGGTCGATGCAAAAACTTCA | 91 |
| mir-015a-2-prec | GCGCGAATGTGTGTTTAAAAAAAATAAAACCTTGGAGTAA AGTAGCAGCACATAATGGTTTGTGGATTTTGAAAAGGTGC AGGCCATATTGTGCTGCCTCAAAAATAC | 92 |
| mir-015a-prec | CCTTGGAGTAAAGTAGCAGCACATAATGGTTTGTGGATTT TGAAAAGGTGCAGGCCATATTGTGCTGCCTCAAAAATACA AGG | 93 |
| mir-015b-prec-1 | CTGTAGCAGCACATCATGGTTTACATGCTACAGTCAAGAT GCGAATCATTATTTGCTGCTCTAG | 94 |
| mir-015b-prec-2 | TTGAGGCCTTAAAGTACTGTAGCAGCACATCATGGTTTAC ATGCTACAGTCAAGATGCGAATCATTATTTGCTGCTCTAG AAATTTAAGGAAATTCAT | 95 |
| mir-016a-chr13 | GTCAGCAGTGCCTTAGCAGCACGTAAATATTGGCGTTAAG ATTCTAAAATTATCTCCAGTATTAACTGTGCTGCTGAAGTA AGGTTGAC | 96 |
| mir-016b-chr3 | GTTCCACTCTAGCAGCACGTAAATATTGGCGTAGTGAAAT ATATATTAAACACCAATATTACTGTGCTGCTTTAGTGTGAC | 97 |
| mir-016-prec-13 | GCAGTGCCTTAGCAGCACGTAAATATTGGCGTTAAGATTC TAAAATTATCTCCAGTATTAACTGTGCTGCTGAAGTAAGG T | 98 |
| mir-017-prec | GTCAGAATAATGTCAAAGTGCTTACAGTGCAGGTAGTGAT ATGTGCATCTACTGCAGTGAAGGCACTTGTAGCATTATGG TGAC | 99 |
| mir-018-prec | TGTTCTAAGGTGCATCTAGTGCAGATAGTGAAGTAGATTA GCATCTACTGCCCTAAGTGCTCCTTCTGGCA | 100 |
| mir-018-prec-13 | TTTTTGTTCTAAGGTGCATCTAGTGCAGATAGTGAAGTAG ATTAGCATCTACTGCCCTAAGTGCTCCTTCTGGCATAAGA A | 101 |
| mir-019a-prec | GCAGTCCTCTGTTAGTTTTGCATAGTTGCACTACAAGAAG AATGTAGTTTGTGCAAATCTATGCAAAACTGATGGTGGCCT GC | 102 |
| mir-019a-prec-13 | CAGTCCTCTGTTAGTTTTGCATAGTTGCACTACAAGAAGA ATGTAGTTTGTGCAAATCTATGCAAAACTGATGGTGGCCTG | 103 |
| mir-019b-1-prec | CACTGTTCTATGGTTAGTTTTGCAGGTTTGCATCCAGCTGT GTGATATTCTGCTGTGCAAATCCATGCAAAACTGACTGTG GTAGTG | 104 |

TABLE 1 -continued

Human miR Gene Product Sequences

| Name | Precursor Sequence (5' to 3')* | SEQ ID NO: |
|---|---|---|
| mir-019b-2-prec | ACATTGCTACTTACAATTAGTTTTGCAGGTTTGCATTTCAG CGTATATATGTATATGTGGC<u>TGTGCAAATCCATGCAAAAC TGA</u>TTGTGATAATGT | 105 |
| mir-019b-prec-13 | TTCTATGGTTAGTTTTGCAGGTTTGCATCCAGCTGTGTGAT ATTC<u>TGCTGTGCAAATCCATGCAAAACTGA</u>CTGTGGTAG | 106 |
| mir-019b-prec-X | TTACAATTAGTTTTGCAGGTTTGCATTTCAGCGTATATATG TATATG<u>TGGCTGTGCAAATCCATGCAAAACTGA</u>TTGTGAT | 107 |
| mir-020-prec | GTAGCAC<u>TAAAGTGCTTATAGTGCAGGTA</u>GTGTTTAGTTA TCTACTGCATTATGAGCACTTAAAGTACTGC | 108 |
| mir-021-prec | TGTCGGG<u>TAGCTTATCAGACTGATGTTGA</u>CTGTTGAATCTC ATGGCAACACCAGTCGATGGGCTGTCTGACA | 109 |
| mir-021-prec-17 | ACCTTGTCGGG<u>TAGCTTATCAGACTGATGTTGA</u>CTGTTGA ATCTCATGGCAACACCAGTCGATGGGCTGTCTGACATTTT G | 110 |
| mir-022-prec | GGCTGAGCCGCAGTAGTTCTTCAGTGGCAAGCTTTATGTC CTGACCCAGCTA<u>AAGCTGCCAGTTGAAGAACTGT</u>TGCCCT CTGCC | 111 |
| mir-023a-prec | GGCCGGCTGGGGTTCCTGGGGATGGGATTTGCTTCCTGTC ACAA<u>ATCACATTGCCAGGGATTTCC</u>AACCGACC | 112 |
| mir-023b-prec | CTCAGGTGCTCTGGCTGCTTGGGTTCCTGGCATGCTGATTT GTGACTTAAGATTAAA<u>ATCACATTGCCAGGGATTAC</u>CACG CAACCACGACCTTGGC | 113 |
| mir-023-prec-19 | CCACGGCCGGCTGGGGTTCCTGGGGATGGGATTTGCTTCC TGTCACAA<u>ATCACATTGCCAGGGATTTCC</u>AACCGACCCTG A | 114 |
| mir-024-1-prec | CTCCGGTGCCTACTGAGCTGATATCAGTTCTCATTTTACAC AC<u>TGGCTCAGTTCAGCAGGAACAG</u>GAG | 115 |
| mir-024-2-prec | CTCTGCCTCCCGTGCCTACTGAGCTGAAACACAGTTGGTTT GTGTACAC<u>TGGCTCAGTTCAGCAGGAACAG</u>GG | 116 |
| mir-024-prec-19 | CCCTGGGCTCTGCCTCCCGTGCCTACTGAGCTGAAACACA GTTGGTTTGTGTACAC<u>TGGCTCAGTTCAGCAGGAACAG</u>GG G | 117 |
| mir-024-prec-9 | CCCTCCGGTGCCTACTGAGCTGATATCAGTTCTCATTTTAC ACAC<u>TGGCTCAGTTCAGCAGGAACAG</u>CATC | 118 |
| mir-025-prec | GGCCAGTGTTGAGAGGCGGAGACTTGGGCAATTGCTGGAC GCTGCCCTGGG<u>CATTGCACTTGTCTCGGTCTGA</u>CAGTGCC GGCC | 119 |
| mir-026a-prec | AGGCCGTGGCCTCG<u>TTCAAGTAATCCAGGATAGG</u>CTGTGC AGGTCCCAATGGCCTATCTTGGTTACTTGCACGGGGACGC GGGCCT | 120 |
| mir-026b-prec | CCGGGACCCAG<u>TTCAAGTAATTCAGGATAGG</u>TTGTGTGCT GTCCAGCCTGTTCTCCATTACTTGGCTCGGGGACCGG | 121 |
| mir-027a-prec | CTGAGGAGCAGGGCTTAGCTGCTTGTGAGCAGGGTCCACA CCAAGTCGTG<u>TTCACAGTGGCTAAGTTCCGCC</u>CCCCAG | 122 |
| mir-027b-prec-1 | AGGTGCAGAGCTTAGCTGATTGGTGAACAGTGATTGGTTT CCGCTTTG<u>TTCACAGTGGCTAAGTTCTGC</u>ACCT | 123 |
| mir-027b-prec-2 | ACCTCTCTAACAAGGTGCAGAGCTTAGCTGATTGGTGAAC AGTGATTGGTTTCCGCTTTG<u>TTCACAGTGGCTAAGTTCTGC</u> ACCTGAAGAGAAGGTG | 124 |
| mir-027-prec-19 | CCTGAGGAGCAGGGCTTAGCTGCTTGTGAGCAGGGTCCAC ACCAAGTCGTG<u>TTCACAGTGGCTAAGTTCCG</u>CCCCCCAGG | 125 |

TABLE 1 -continued

Human miR Gene Product Sequences

| Name | Precursor Sequence (5' to 3')* | SEQ ID NO: |
|---|---|---|
| mir-028-prec | GGTCCTTGCCCTCAAGGAGCTCACAGTCTATTGAGTTACCTTTCTGACTTTCCCACTAGATTGTGAGCTCCTGGAGGGCAGGCACT | 126 |
| mir-029a-2 | CCTTCTGTGACCCCTTAGAGGATGACTGATTTCTTTTGGTGTTCAGAGTCAATATAATTTTCTAGCACCATCTGAAATCGGTTATAATGATTGGGGAAGAGCACCATG | 127 |
| mir-029a-prec | ATGACTGATTTCTTTTGGTGTTCAGAGTCAATATAATTTTCTAGCACCATCTGAAATCGGTTAT | 128 |
| mir-029c-prec | ACCACTGGCCCATCTCTTACACAGGCTGACCGATTTCTCCTGGTGTTCAGAGTCTGTTTTTGTCTAGCACCATTTGAAATCGGTTATGATGTAGGGGGAAAAGCAGCAGC | 129 |
| mir-030a-prec | GCGACTGTAAACATCCTCGACTGGAAGCTGTGAAGCCACAGATGGGCTTTCAGTCGGATGTTTGCAGCTGC | 130 |
| mir-030b-prec-1 | ATGTAAACATCCTACACTCAGCTGTAATACATGGATTGGCTGGGAGGTGGATGTTTACGT | 131 |
| mir-030b-prec-2 | ACCAAGTTTCAGTTCATGTAAACATCCTACACTCAGCTGTAATACATGGATTGGCTGGGAGGTGGATGTTTACTTCAGCTGACTTGGA | 132 |
| mir-030c-prec | AGATACTGTAAACATCCTACACTCTCAGCTGTGGAAAGTAAGAAAGCTGGGAGAAGGCTGTTTACTCTTTCT | 133 |
| mir-030d-prec | GTTGTTGTAAACATCCCCGACTGGAAGCTGTAAGACACAGCTAAGCTTTCAGTCAGATGTTTGCTGCTAC | 134 |
| mir-031-prec | GGAGAGGAGGCAAGATGCTGGCATAGCTGTTGAACTGGGAACCTGCTATGCCAACATATTGCCATCTTTCC | 135 |
| mir-032-prec | GGAGATATTGCACATTACTAAGTTGCATGTTGTCACGGCCTCAATGCAATTTAGTGTGTGTGATATTTTC | 136 |
| mir-033b-prec | GGGGGCCGAGAGAGGCGGGCGGCCCCGCGGTGCATTGCTGTTGCATTGCACGTGTGTGAGGCGGGTGCAGTGCCTCGGCAGTGCAGCCCGGAGCCGGCCCCTGGCACCAC | 137 |
| mir-033-prec | CTGTGGTGCATTGTAGTTGCATTGCATGTTCTGGTGGTACCCATGCAATGTTTCCACAGTGCATCACAG | 138 |
| mir-034-prec | GGCCAGCTGTGAGTGTTTCTTTGGCAGTGTCTTAGCTGGTTGTTGTGAGCAATAGTAAGGAAGCAATCAGCAAGTATACTGCCCTAGAAGTGCTGCACGTTGTGGGGCCC | 139 |
| mir-091-prec-13 | TCAGAATAATGTCAAAGTGCTTACAGTGCAGGTAGTGATATGTGCATCTACTGCAGTGAAGGCACTTGTAGCATTATGGTGA | 140 |
| mir-092-prec-13 = 092-1 | CTTTCTACACAGGTTGGGATCGGTTGCAATGCTGTGTTTCTGTATGGTATTGCACTTGTCCCGGCCTGTTGAGTTTGG | 141 |
| mir-092-prec-X = 092-2 | TCATCCCTGGGTGGGGATTTGTTGCATTACTTGTGTTCTATATAAAGTATTGCACTTGTCCCGGCCTGTGGAAGA | 142 |
| mir-093-prec-7.1 = 093-1 (mir-093-prec-7.2 = 093-2) | CTGGGGGCTCCAAAGTGCTGTTCGTGCAGGTAGTGTGATTACCCAACCTACTGCTGAGCTAGCACTTCCCGAGCCCCCGG | 143 |
| mir-095-prec-4 | AACACAGTGGGCACTCAATAAATGTCTGTTGAATTGAAATGCGTTACATTCAACGGGTATTTATTGAGCACCCACTCTGTG | 144 |
| mir-096-prec-7 | TGGCCGATTTTGGCACTAGCACATTTTTGCTTGTGTCTCTCCGCTCTGAGCAATCATGTGCAGTGCCAATATGGGAAA | 145 |
| mir-098-prec-X | GTGAGGTAGTAAGTTGTATTGTTGTGGGGTAGGGATATTAGGCCCCAATTAGAAGATAACTATACAACTTACTACTTTCC | 146 |
| mir-099b-prec-19 | GGCACCCACCCCGTAGAACCGACCTTGCGGGGCCTTCGCCGCACACAAGCTCGTGTCTGTGGGTCCGTGTC | 147 |

TABLE 1 -continued

Human miR Gene Product Sequences

| Name | Precursor Sequence (5' to 3')* | SEQ ID NO: |
|---|---|---|
| mir-099-prec-21 | CCCATTGGCATAAACCCGTAGATCCGATCTTGTGGTGAAGTGGACCGCACAAGCTCGCTTCTATGGGTCTGTGTCAGTGTG | 148 |
| mir-100-1/2-prec | AAGAGAGAAGATATTGAGGCCTGTTGCCACAAACCCGTAGATCCGAACTTGTGGTATTAGTCCGCACAAGCTTGTATCTATAGGTATGTGTCTGTTAGGCAATCTCAC | 149 |
| mir-100-prec-11 | CCTGTTGCCACAAACCCGTAGATCCGAACTTGTGGTATTAGTCCGCACAAGCTTGTATCTATAGGTATGTGTCTGTTAGG | 150 |
| mir-101-1 /2-prec | AGGCTGCCCTGGCTCAGTTATCACAGTGCTGATGCTGTCTATTCTAAAGGTACAGTACTGTGATAACTGAAGGATGGCAGCCATCTTACCTTCCATCAGAGGAGCCTCAC | 151 |
| mir-101-prec | TCAGTTATCACAGTGCTGATGCTGTCCATTCTAAAGGTACAGTACTGTGATAACTGA | 152 |
| mir-101-prec-1 | TGCCCTGGCTCAGTTATCACAGTGCTGATGCTGTCTATTCTAAAGGTACAGTACTGTGATAACTGAAGGATGGCA | 153 |
| mir-101-prec-9 | TGTCCTTTTTCGGTTATCATGGTACCGATGCTGTATATCTGAAAGGTACAGTACTGTGATAACTGAAGAATGGTG | 154 |
| mir-102-prec-1 | CTTCTGGAAGCTGGTTTCACATGGTGGCTTAGATTTTTCCATCTTTTGTATCTAGCACCATTTGAAATCAGTGTTTTAGGAG | 155 |
| mir-102-prec-7.1 (mir-102-prec-7.2) | CTTCAGGAAGCTGGTTTCATATGGTGGTTTAGATTTAAATAGTGATTGTCTAGCACCATTTGAAATCAGTGTTCTTGGGGG | 156 |
| mir-103-2-prec (mir-103-prec-20) | TTGTGCTTTCAGCTTCTTTACAGTGCTGCCTTGTAGCATTCAGGTCAAGCAACATTGTACAGGGCTATGAAAGAACCA | 157 |
| mir-103-prec-5 = 103-1 | TACTGCCCTCGGCTTCTTTACAGTGCTGCCTTGTTGCATATGGATCAAGCAGCATTGTACAGGGCTATGAAGGCATTG | 158 |
| mir-104-prec-17 | AAATGTCAGACAGCCCATCGACTGGTGTTGCCATGAGATTCAACAGTCAACATCAGTCTGATAAGCTACCCGACAAGG | 159 |
| mir-105-prec-X.1 (mir-105-1; mir-105-prec-X.2; mir-105-2) | TGTGCATCGTGGTCAAATGCTCAGACTCCTGTGGTGGCTGCTCATGCACCACGGATGTTTGAGCATGTGCTACGGTGTCTA | 160 |
| mir-106-prec-X | CCTTGGCCATGTAAAAGTGCTTACAGTGCAGGTAGCTTTTTGAGATCTACTGCAATGTAAGCACTTCTTACATTACCATGG | 161 |
| mir-107-prec-10 | CTCTCTGCTTTCAGCTTCTTTACAGTGTTGCCTTGTGGCATGGAGTTCAAGCAGCATTGTACAGGGCTATCAAAGCACAGA | 162 |
| mir-122a-prec-1 | CCTTAGCAGAGCTGTGGAGTGTGACAATGGTGTTTGTGTCTAAACTATCAAACGCCATTATCACACTAAATAGCTACTGCTAGGC | 163 |
| mir-122a-prec-2 | AGCTGTGGAGTGTGACAATGGTGTTTGTGTCCAAACTATCAAACGCCATTATCACACTAAATAGCT | 164 |
| mir-123-prec | ACATTATTACTTTTGGTACGCGCTGTGACACTTCAAACTCGTACCGTGAGTAATAATGCGC | 165 |
| mir-124a-1-prec-1 | tccttcctCAGGAGAAAGGCCTCTCTCTCCGTGTTCACAGCGGACCTTGATTTAAATGTCCATACAATTAAGGCACGCGGTGAATGCCAAGAATGGGCT | 166 |
| mir-124a-1-prec-2 | AGGCCTCTCTCTCCGTGTTCACAGCGGACCTTGATTTAAATGTCCATACAATTAAGGCACGCGGTGAATGCCAAGAATGGGGCTG | 167 |
| mir-124a-2-prec | ATCAAGATTAGAGGCTCTGCTCTCCGTGTTCACAGCGGACCTTGATTTAATGTCATACAATTAAGGCACGCGGTGAATGCCAAGAGCGGAGCCTACGGCTGCACTTGAAG | 168 |

TABLE 1 -continued

Human miR Gene Product Sequences

| Name | Precursor Sequence (5' to 3')* | SEQ ID NO: |
|---|---|---|
| mir-124a-3-prec-1 | CCCGCCCCAGCCCTGAGGGCCCCTCTGCGTGTTCACAGCG GACCTTGATTTAATGTCTATACAATTAAGGCACGCGGTGA ATGCCAAGAGAGGCGCCTCCGCCGCTCCTT | 169 |
| mir-124a-3-prec-2 | TGAGGGCCCCTCTGCGTGTTCACAGCGGACCTTGATTTAA TGTCTATACAATTAAGGCACGCGGTGAATGCCAAGAGAGG CGCCTCC | 170 |
| mir-124a-prec | CTCTGCGTGTTCACAGCGGACCTTGATTTAATGTCTATACA ATTAAGGCACGCGGTGAATGCCAAGAG | 171 |
| mir-124b-prec | CTCTCCGTGTTCACAGCGGACCTTGATTTAATGTCATACAA TTAAGGCACGCGGTGAATGCCAAGAG | 172 |
| mir-125a-prec-1 | TGCCAGTCTCTAGGTCCCTGAGACCCTTTAACCTGTGAGG ACATCCAGGGTCACAGGTGAGGTTCTTGGGAGCCTGGCGT CTGGCC | 173 |
| mir-125a-prec-2 | GGTCCCTGAGACCCTTTAACCTGTGAGGACATCCAGGGTC ACAGGTGAGGTTCTTGGGAGCCTGG | 174 |
| mir-125b-1-1 | ACATTGTTGCGCTCCTCTCAGTCCCTGAGACCCTAACTTGT GATGTTTACCGTTTAAATCCACGGGTTAGGCTCTTGGGAG CTGCGAGTCGTGCTTTTGCATCCTGGA | 175 |
| mir-125b-1-2 | TGCGCTCCTCTCAGTCCCTGAGACCCTAACTTGTGATGTTT ACCGTTTAAATCCACGGGTTAGGCTCTTGGGAGCTGCGAG TCGTGCT | 176 |
| mir-125b-2-prec-1 | ACCAGACTTTTCCTAGTCCCTGAGACCCTAACTTGTGAGGT ATTTTAGTAACATCACAAGTCAGGCTCTTGGGACCTAGGC GGAGGGGA | 177 |
| mir-125b-2-prec-2 | CCTAGTCCCTGAGACCCTAACTTGTGAGGTATTTTAGTAAC ATCACAAGTCAGGCTCTTGGGACCTAGGC | 178 |
| mir-126-prec-1 | CGCTGGCGACGGGACATTATTACTTTTGGTACGCGCTGTG ACACTTCAAACTCGTACCGTGAGTAATAATGCGCCGTCCA CGGCA | 179 |
| mir-126-prec-2 | ACATTATTACTTTTGGTACGCGCTGTGACACTTCAAACTCG TACCGTGAGTAATAATGCGC | 180 |
| mir-127-prec-1 | TGTGATCACTGTCTCCAGCCTGCTGAAGCTCAGAGGGCTC TGATTCAGAAAGATCATCGGATCCGTCTGAGCTTGGCTGG TCGGAAGTCTCATCATC | 181 |
| mir-127-prec-2 | CCAGCCTGCTGAAGCTCAGAGGGCTCTGATTCAGAAAGAT CATCGGATCCGTCTGAGCTTGGCTGGTCGG | 182 |
| mir-128a-prec | TGAGCTGTTGGATTCGGGGCCGTAGCACTGTCTGAGAGGT TTACATTTCTCACAGTGAACCGGTCTCTTTTTCAGCTGCTT C | 183 |
| mir-128b-prec | GCCCGGCAGCCACTGTGCAGTGGGAAGGGGGGCCGATAC ACTGTACGAGAGTGAGTAGCAGGTCTCACAGTGAACCGGT CTCTTTCCCTACTGTGTCACACTCCTAATGG | 184 |
| mir-128-prec | GTTGGATTCGGGGCCGTAGCACTGTCTGAGAGGTTTACAT TTCTCACAGTGAACCGGTCTCTTTTTCAGC | 185 |
| mir-129-prec | TGGATCTTTTTGCGGTCTGGGCTTGCTGTTCCTCTCAACAG TAGTCAGGAAGCCCTTACCCCAAAAAGTATCTA | 186 |
| mir-130a-prec | TGCTGCTGGCCAGAGCTCTTTTCACATTGTGCTACTGTCTG CACCTGTCACTAGCAGTGCAATGTTAAAAGGGCATTGGCC GTGTAGTG | 187 |
| mir-131-1-prec | gccaggaggcggGGTTGGTTGTTATCTTTGGTTATCTAGCTGTAT GAGTGGTGTGGAGTCTTCATAAAGCTAGATAACCGAAAGT AAAAATAACCCCATACACTGCGCAG | 188 |
| mir-131-3-prec | CACGGCGCGGCAGCGGCACTGGCTAAGGGAGGCCCGTTTC TCTCTTTGGTTATCTAGCTGTATGAGTGCCACAGAGCCGTC ATAAAGCTAGATAACCGAAAGTAGAAATG | 189 |

TABLE 1 -continued

Human miR Gene Product Sequences

| Name | Precursor Sequence (5' to 3')* | SEQ ID NO: |
|---|---|---|
| mir-131-prec | GTTGTTATCTTTGGTTATCTAGCTGTATGAGTGTATTGGTC TTCA<u>TAAAGCTAGATAACCGAAAGT</u>AAAAAC | 190 |
| mir-132-prec-1 | CCGCCCCCGCGTCTCCAGGGCAACCGTGGCTTTCGATTGTT ACTGTGGGAACTGGAGG<u>TAACAGTCTACAGCCATGGTCGC</u> CCCGCAGCACGCCCACGCGC | 191 |
| mir-132-prec-2 | GGGCAACCGTGGCTTTCGATTGTTACTGTGGGAACTGGAG G<u>TAACAGTCTACAGCCATGGT</u>CGCCC | 192 |
| mir-133a-1 | ACAATGCTTTGCTAGAGCTGGTAAAATGGAACCAAATCGC CTCTTCAATGGAT<u>TTGGTCCCCTTCAACCAGCTGT</u>AGCTAT GCATTGA | 193 |
| mir-133a-2 | GGGAGCCAAATGCTTTGCTAGAGCTGGTAAAATGGAACCA AATCGACTGTCCAATGGAT<u>TTGGTCCCCTTCAACCAGCTGT</u> AGCTGTGCATTGATGGCGCCG | 194 |
| mir-133-prec | GCTAGAGCTGGTAAAATGGAACCAAATCGCCTCTTCAATG GAT<u>TTGGTCCCCTTCAACCAGCTGT</u>AGC | 195 |
| mir-134-prec-1 | CAGGGTG<u>TGTGACTGGTTGACCAGAGGGG</u>CATGCACTGTG TTCACCCTGTGGGCCACCTAGTCACCAACCCTC | 196 |
| mir-134-prec-2 | AGGGTG<u>TGTGACTGGTTGACCAGAGGGG</u>CATGCACTGTGT TCACCCTGTGGGCCACCTAGTCACCAACCCT | 197 |
| mir-135-1-prec | AGGCCTCGCTGTTCTC<u>TATGGCTTTTTATTCCTATGTGATT</u> CTACTGCTCACTCATATAGGGATTGGAGCCGTGGCGCACG GCGGGGACA | 198 |
| mir-135-2-prec | AGATAAATTCACTCTAGTGCTT<u>TATGGCTTTTTATTCCTAT GTGA</u>TAGTAATAAAGTCTCATGTAGGGATGGAAGCCATGA AATACATTGTGAAAAATCA | 199 |
| mir-135-prec | C<u>TATGGCTTTTTATTCCTATGTGATT</u>CTACTGCTCACTCAT ATAGGGATTGGAGCCGTGG | 200 |
| mir-136-prec-1 | TGAGCCCTCGGAGG<u>ACTCCATTTGTTTTGATGATGG</u>ATTCT TATGCTCCATCATCGTCTCAAATGAGTCTTCAGAGGGTTCT | 201 |
| mir-136-prec-2 | GAGG<u>ACTCCATTTGTTTTGATGATGG</u>ATTCTTATGCTCCAT CATCGTCTCAAATGAGTCTTC | 202 |
| mir-137-prec | CTTCGGTGACGGGTATTCTTGGGTGGATAATACGGATTAC GTTGT<u>TATTGCTTAAGAATACGCGTAGT</u>CGAGG | 203 |
| mir-138-1-prec | CCCTGGCATGGTGTGGTGGGGG<u>CAGCTGGTGTTGTGAATCA</u> GGCCGTTGCCAATCAGAGAACGGCTACTTCACAACACCAG GGCCACACCACACTACAGG | 204 |
| mir-138-2-prec | CGTTGCTGC<u>AGCTGGTGTTGTGAATCA</u>GGCCGACGAGCAG CGCATCCTCTTACCCGGCTATTTCACGACACCAGGGTTGC ATCA | 205 |
| mir-138-prec | C<u>AGCTGGTGTTGTGAATCA</u>GGCCGACGAGCAGCGCATCCT CTTACCCGGCTATTTCACGACACCAGGGTTG | 206 |
| mir-139-prec | GTGTAT<u>TCTACAGTGCACGTGTCT</u>CCAGTGTGGCTCGGAG GCTGGAGACGCGGCCCTGTTGGAGTAAC | 207 |
| mir-140 | TGTGTCTCTCTCTGTGTCCTGCCAGTGGTTTTACCCTATGG TAGGTTACGTCATGCTGTTC<u>TACCACAGGGTAGAACCACG GA</u>CAGGATACCGGGGCACC | 208 |
| mir-140as-prec | TCCTGCCAGTGGTTTTACCCTATGGTAGGTTACGTCATGCT GTTC<u>TACCACAGGGTAGAACCACGGA</u>CAGGA | 209 |
| mir-140s-prec | CCTGCCAGTGGTTTTACCCTATGGTAGGTTACGTCATGCTG TTC<u>TACCACAGGGTAGAACCACGGA</u>CAGG | 210 |
| mir-141-prec-1 | CGGCCGGCCCTGGGTCCATCTTCCAGTACAGTGTTGGATG GTCTAATTGTGAAGCTCCT<u>AACACTGTCTGGTAAAGATGG</u> CTCCCGGGTGGGTTC | 211 |

TABLE 1-continued

Human miR Gene Product Sequences

| Name | Precursor Sequence (5' to 3')* | SEQ ID NO: |
|---|---|---|
| mir-141-prec-2 | GGGTCCATCTTCCAGTACAGTGTTGGATGGTCTAATTGTG AAGCTCCT<u>AACACTGTCTGGTAAAGATGG</u>CCC | 212 |
| mir-142as-prec (mir-142s-prec) | ACCC<u>CATAAAGTAGAAAGCACTAC</u>TAACAGCACTGGAGGG TGTAGTGTTTCCTACTTTATGGATG | 213 |
| mir-142s-pres | ACCC<u>CATAAAGTAGAAAGCACTAC</u>TAACAGCACTGGAGGG TGTAGTGTTTCCTACTTTATGGATG | 214 |
| mir-143-prec-1 | GCGCAGCGCCCTGTCTCCCAGCCTGAGGTGCAGTGCTGCA TCTCTGGTCAGTTGGGAGTC<u>TGAGATGAAGCACTGTAGCT CA</u>GGAAGAGAGAAGTTGTTCTGCAGC | 215 |
| mir-143-prec-2 | CCTGAGGTGCAGTGCTGCATCTCTGGTCAGTTGGGAGTC<u>T GAGATGAAGCACTGTAGCTCAGG</u> | 216 |
| mir-144-prec-1 | TGGGGCCCTGGCTGGGATATCATCATATACTGTAAGTTTG CGATGAGACAC<u>TACAGTATAGATGATGTACTAGT</u>CCGGGC ACCCCC | 217 |
| mir-144-prec-2 | GGCTGGGATATCATCATATACTGTAAGTTTGCGATGAGAC AC<u>TACAGTATAGATGATGTACTAGT</u>C | 218 |
| mir-145-prec-1 | CACCTTGTCCTCACG<u>GTCCAGTTTTCCCAGGAATCCCTTAG</u> ATGCTAAGATGGGGATTCCTGGAAATACTGTTCTTGAGGT CATGGTT | 219 |
| mir-145-prec-2 | CTCACG<u>GTCCAGTTTTCCCAGGAATCCCTT</u>AGATGCTAAG ATGGGGATTCCTGGAAATACTGTTCTTGAG | 220 |
| mir-146-prec-1 | CCGATGTGTATCCTCAGCTTT<u>GAGAACTGAATTCCATGGG TT</u>GTGTCAGTGTCAGACCTCTGAAATTCAGTTCTTCAGCTG GGATATCTCTGTCATCGT | 221 |
| mir-146-prec-2 | AGCTT<u>TGAGAACTGAATTCCATGGGTT</u>GTGTCAGTGTCAG ACCTGTGAAATTCAGTTCTTCAGCT | 222 |
| mir-147-prec | AATCTAAAGACAACATTTCTGCACACACACCAGACTATGG AAGCCA<u>GTGTGTGGAAATGCTTCTGC</u>TAGATT | 223 |
| mir-148-prec | GAGGCAAAGTTCTGAGACACTCCGACTCTGAGTATGATAG AAGT<u>CAGTGCACTACAGAACTTTGT</u>CTC | 224 |
| mir-149-prec-1 | GCCGGCGCCCGAGC<u>TCTGGCTCCGTGTCTTCACTCCC</u>GTGC TTGTCCGAGGAGGGAGGGAGGGACGGGGGCTGTGCTGGG GCAGCTGGA | 225 |
| mir-149-prec-2 | GCT<u>CTGGCTCCGTGTCTTCACTCCC</u>GTGCTTGTCCGAGGAG GGAGGGAGGGAC | 226 |
| mir-150-prec-1 | CTCCCCATGGCCCTG<u>TCTCCCAACCCTTGTACCAGTGCTGG</u> GCTCAGACCCTGGTACAGGCCTGGGGGACAGGGACCTGG GGAC | 227 |
| mir-150-prec-2 | CCCTG<u>TCTCCCAACCCTTGTACCAGTGC</u>TGGGCTCAGACCC TGGTACAGGCCTGGGGGACAGGG | 228 |
| mir-151-prec | CCTGCCCTCGAGGAGCTCACAGTCTAGTATGTCTCATCCCC TAC<u>TAGACTGAAGCTCCTTGAGG</u>ACAGG | 229 |
| mir-152-prec-1 | TGTCCCCCCGGCCCAGGTTCTGTGATACACTCCGACTCG GGCTCTGGAGCAGT<u>CAGTGCATGACAGAACTTGGG</u>CCCGG AAGGACC | 230 |
| mir-152-prec-2 | GGCCCAGGTTCTGTGATACACTCCGACTCGGGCTCTGGAG CAGT<u>CAGTGCATGACAGAACTTGGG</u>CCCCGG | 231 |
| mir-153-1-prec-1 | CTCACAGCTGCCAGTGTCATTTTTGTGATCTGCAGCTAGTA TTCTCACTCCAG<u>TTGCATAGTCACAAAAGTGATCATTGGC</u> AGGTGTGGC | 232 |
| mir-153-1-prec-2 | tctctctctccctcACAGCTGCCAGTGTCA<u>TTGTCACAAAAGTGAT</u> CATTGGCAGGTGTGGCTGCTGCATG | 233 |

TABLE 1-continued

Human miR Gene Product Sequences

| Name | Precursor Sequence (5' to 3')* | SEQ ID NO: |
|---|---|---|
| mir-153-2-prec-1 | AGCGGTGGCCAGTGTCATTTTTGTGATGTTGCAGCTAGTA ATATGAGCCCAGTTGCATAGTCACAAAAGTGATCATTGGA AACTGTG | 234 |
| mir-153-2-prec-2 | CAGTGTCATTTTTGTGATGTTGCAGCTAGTAATATGAGCCC AGTTGCATAGTCACAAAAGTGATCATTG | 235 |
| mir-154-prec-1 | GTGGTACTTGAAGATAGGTTATCCGTGTTGCCTTCGCTTTA TTTGTGACGAATCATACACGGTTGACCTATTTTTCAGTACC AA | 236 |
| mir-154-prec-2 | GAAGATAGGTTATCCGTGTTGCCTTCGCTTTATTTGTGACG AATCATACACGGTTGACCTATTTTT | 237 |
| mir-155-prec | CTGTTAATGCTAATCGTGATAGGGGTTTTTGCCTCCAACTG ACTCCTACATATTAGCATTAACAG | 238 |
| mir-16-2-prec | CAATGTCAGCAGTGCCTTAGCAGCACGTAAATATTGGCGT TAAGATTCTAAAATTATCTCCAGTATTAACTGTGCTGCTGA AGTAAGGTTGACCATACTCTACAGTTG | 239 |
| mir-181a-prec | AGAAGGGCTATCAGGCCAGCCTTCAGAGGACTCCAAGGA ACATTCAACGCTGTCGGTGAGTTTGGGATTTGAAAAAACC ACTGACCGTTGACTGTACCTTGGGGTCCTTA | 240 |
| mir-181b-prec | TGAGTTTTGAGGTTGCTTCAGTGAACATTCAACGCTGTCG GTGAGTTTGGAATTAAAATCAAAACCATCGACCGTTGATT GTACCCTATGGCTAACCATCATCTACTCCA | 241 |
| mir-181c-prec | CGGAAAATTTGCCAAGGGTTTGGGGGAACATTCAACCTGT CGGTGAGTTTGGGCAGCTCAGGCAAACCATCGACCGTTGA GTGGACCCTGAGGCCTGGAATTGCCATCCT | 242 |
| mir-182-as-prec | GAGCTGCTTGCCTCCCCCCGTTTTTGGCAATGGTAGAACTC ACACTGGTGAGGTAACAGGATCCGGTGGTTCTAGACTTGC CAACTATGGGGCGAGGACTCAGCCGGCAC | 243 |
| mir-182-prec | TTTTTGGCAATGGTAGAACTCACACTGGTGAGGTAACAGG ATCCGGTGGTTCTAGACTTGCCAACTATGG | 244 |
| mir-183-prec | CCGCAGAGTGTGACTCCTGTTCTGTGTATGGCACTGGTAG AATTCACTGTGAACAGTCTCAGTCAGTGAATTACCGAAGG GCCATAAACAGAGCAGAGACAGATCCACGA | 245 |
| mir-184-prec-1 | CCAGTCACGTCCCCTTATCACTTTTCCAGCCCAGCTTTGTG ACTGTAAGTGTTGGACGGAGAACTGATAAGGGTAGGTGAT TGA | 246 |
| mir-184-prec-2 | CCTTATCACTTTTCCAGCCCAGCTTTGTGACTGTAAGTGTT GGACGGAGAACTGATAAGGGTAGG | 247 |
| mir-185-prec-1 | AGGGGGCGAGGGATTGGAGAGAAAGGCAGTTCCTGATGG TCCCCTCCCCAGGGGCTGGCTTTCCTCTGGTCCTTCCCTCC CA | 248 |
| mir-185-prec-2 | AGGGATTGGAGAGAAAGGCAGTTCCTGATGGTCCCCTCCC CAGGGGCTGGCTTTCCTCTGGTCCTT | 249 |
| mir-186-prec-1 | TGCTTGTAACTTTCCAAAGAATTCTCCTTTTGGGCTTTCTG GTTTTATTTTAAGCCCAAAGGTGAATTTTTTGGGAAGTTTG AGCT | 250 |
| mir-186-prec-2 | ACTTTCCAAAGAATTCTCCTTTTGGGCTTTCTGGTTTTATTT TAAGCCCAAAGGTGAATTTTTTGGGAAGT | 251 |
| mir-187-prec | GGTCGGGCTCACCATGACACAGTGTGAGACTCGGGCTACA ACACAGGACCCGGGGCGCTGCTCTGACCCCTCGTGTCTTG TGTTGCAGCCGGAGGGACGCAGGTCCGCA | 252 |
| mir-188-prec-1 | TGCTCCCTCTCTCACATCCCTTGCATGGTGGAGGGTGAGCT TTCTGAAAACCCCTCCCACATGCAGGGTTTGCAGGATGGC GAGCC | 253 |
| mir-188-prec-2 | TCTCACATCCCTTGCATGGTGGAGGGTGAGCTTTCTGAAA ACCCCTCCCACATGCAGGGTTTGCAGGA | 254 |

TABLE 1 -continued

Human miR Gene Product Sequences

| Name | Precursor Sequence (5' to 3')* | SEQ ID NO: |
|---|---|---|
| mir-189-prec-1 | CTGTCGATTGGACCCGCCCTCCG<u>GTGCCTACTGAGCTGAT</u><br><u>ATCAGT</u>TCTCATTTTACACACTGGCTCAGTTCAGCAGGAA<br>CAGGAGTCGAGCCCTTGAGCAA | 255 |
| mir-189-prec-2 | CTCCG<u>GTGCCTACTGAGCTGATATCAGT</u>TCTCATTTTACAC<br>ACTGGCTCAGTTCAGCAGGAACAGGAG | 256 |
| mir-190-prec-1 | TGCAGGCCTCTGTG<u>TGATATGTTTGATATATTAGGTTGTTA</u><br>TTTAATCCAACTATATATCAAACATATTCCTACAGTGTCTT<br>GCC | 257 |
| mir-190-prec-2 | CTGTG<u>TGATATGTTTGATATATTAGGTTGTT</u>ATTTAATCCA<br>ACTATATATCAAACATATTCCTACAG | 258 |
| mir-191-prec-1 | CGGCTGGACAGCGGG<u>CAACGGAATCCCAAAAGCAGCTGT</u><br>TGTCTCCAGAGCATTCCAGCTGCGCTTGGATTTCGTCCCCT<br>GCTCTCCTGCCT | 259 |
| mir-191-prec-2 | AGCGGG<u>CAACGGAATCCCAAAAGCAGCTGT</u>TGTCTCCAGA<br>GCATTCCAGCTGCGCTTGGATTTCGTCCCCTGCT | 260 |
| mir-192-2/3 | CCGAGACCGAGTGCACAGGGCT<u>CTGACCTATGAATTGACA</u><br><u>GCC</u>AGTGCTCTCGTCTCCCCTCTGGCTGCCAATTCCATAGG<br>TCACAGGTATGTTCGCCTCAATGCCAG | 261 |
| mir-192-prec | GCCGAGACCGAGTGCACAGGGCT<u>CTGACCTATGAATTGAC</u><br><u>AGCC</u>AGTGCTCTCGTCTCCCCTCTGGCTGCCAATTCCATAG<br>GTCACAGGTATGTTCGCCTCAATGCCAGC | 262 |
| mir-193-prec-1 | CGAGGATGGGAGCTGAGGGCTGGGTCTTTGCGGGCGAGA<br>TGAGGGTGTCGGATC<u>AACTGGCCTACAAAGTCCCAGT</u>TCT<br>CGGCCCCCG | 263 |
| mir-193-prec-2 | GCTGGGTCTTTGCGGGCGAGATGAGGGTGTCGGATC<u>AACT</u><br><u>GGCCTACAAAGTCCCAGT</u> | 264 |
| mir-194-prec-1 | ATGGTGTTATCAAG<u>TGTAACAGCAACTCCATGTGGA</u>CTGT<br>GTACCAATTTCCAGTGGAGATGCTGTTACTTTTGATGGTTA<br>CCAA | 265 |
| mir-194-prec-2 | <u>GTGTAACAGCAACTCCATGTGGA</u>CTGTGTACCAATTTCCA<br>GTGGAGATGCTGTTACTTTTGAT | 266 |
| mir-195-prec-1 | AGCTTCCCTGGCTC<u>TAGCAGCACAGAAATATTGGCACAGG</u><br>GAAGCGAGTCTGCCAATATTGGCTGTGCTGCTCCAGGCAG<br>GGTGGTG | 267 |
| mir-195-prec-2 | <u>TAGCAGCACAGAAATATTGGCACAGG</u>GAAGCGAGTCTGC<br>CAATATTGGCTGTGCTGCT | 268 |
| mir-196-1-prec | CTAGAGCTTGAATTGGAACTGCTGAGTGAAT<u>AGGTAGTT</u><u>TCATGTTGTTGGG</u>CCTGGGTTTCTGAACACAACAACATTA<br>AACCACCCGATTCACGGCAGTTACTGCTCC | 269 |
| mir-196-1-prec | GTGAAT<u>AGGTAGTTTCATGTTGTTGGG</u>CCTGGGTTTCTGA<br>ACACAACAACATTAAACCACCCGATTCAC | 270 |
| mir-196-2-prec | TGCTCGCTCAGCTGATCTGTGGCT<u>TAGGTAGTTTCATGTTG</u><u>TTGGG</u>ATTGAGTTTTGAACTCGGCAACAAGAAACTGCCTG<br>AGTTACATCAGTCGGTTTTCGTCGAGGGC | 271 |
| mir-196-prec | GTGAAT<u>AGGTAGTTTCATGTTGTTGGG</u>CCTGGGTTTCTGA<br>ACACAACAACATTAAACCACCCGATTCAC | 272 |
| mir-197-prec | GGCTGTGCCGGGTAGAGAGGGCAGTGGGAGGTAAGAGCT<br>CTTCACCC<u>TTCACCACCTTCTCCACCCAGC</u>ATGGCC | 273 |
| mir-198-prec | TCATT<u>GGTCCAGAGGGGAGATAGG</u>TTCCTGTGATTTTTCCT<br>TCTTCTCTATAGAATAAATGA | 274 |
| mir-199a-1-prec | GCCA<u>CCCAGTGTTCAGACTACCTGTT</u>CAGGAGGCTCTCA<br>ATGTGTACAGTAGTCTGCACATTGGTTAGGC | 275 |

TABLE 1 -continued

Human miR Gene Product Sequences

| Name | Precursor Sequence (5' to 3')* | SEQ ID NO: |
|---|---|---|
| mir-199a-2-prec | AGGAAGCTTCTGGAGATCCTGCTCCGTCGCCCCAGTGTTCAGACTACCTGTTCAGGACAATGCCGTTGTACAGTAGTCTGCACATTGGTTAGACTGGGCAAGGGAGAGCA | 276 |
| mir-199b-prec | CCAGAGGACACCTCCACTCCGTCTACCCAGTGTTTAGACTATCTGTTCAGGACTCCCAAATTGTACAGTAGTCTGCACATTGGTTAGGCTGGGCTGGGTTAGACCCTCGG | 277 |
| mir-199s-prec | GCCAACCCAGTGTTCAGACTACCTGTTCAGGAGGCTCTCAATGTGTACAGTAGTCTGCACATTGGTTAGGC | 278 |
| mir-200a-prec | GCCGTGGCCATCTTACTGGGCAGCATTGGATGGAGTCAGGTCTCTAATACTGCCTGGTAATGATGACGGC | 279 |
| mir-200b-prec | CCAGCTCGGGCAGCCGTGGCCATCTTACTGGGCAGCATTGGATGGAGTCAGGTCTCTAATACTGCCTGGTAATGATGACGGCGGAGCCCTGCACG | 280 |
| mir-202-prec | GTTCCTTTTTCCTATGCATATACTTCTTTGAGGATCTGGCCTAAAGAGGTATAGGGCATGGGAAGATGGAGC | 281 |
| mir-203-prec | GTGTTGGGGACTCGCGCGCTGGGTCCAGTGGTTCTTAACAGTTCAACAGTTCTGTAGCGCAATTGTGAAATGTTTAGGACCACTAGACCCGGCGGGCGCGGCGACAGCGA | 282 |
| mir-204-prec | GGCTACAGTCTTTCTTCATGTGACTCGTGGACTTCCCTTTGTCATCCTATGCCTGAGAATATATGAAGGAGGCTGGGAAGGCAAAGGGACGTTCAATTGTCATCACTGGC | 283 |
| mir-205-prec | AAAGATCCTCAGACAATCCATGTGCTTCTCTTGTCCTTCATTCCACCGGAGTCTGTCTCATACCCAACCAGATTTCAGTGGAGTGAAGTTCAGGAGGCATGGAGCTGACA | 284 |
| mir-206-prec-1 | TGCTTCCCGAGGCCACATGCTTCTTTATATCCCCATATGGATTACTTTGCTATGGAATGTAAGGAAGTGTGTGGTTTCGGCAAGTG | 285 |
| mir-206-prec-2 | AGGCCACATGCTTCTTTATATCCCCATATGGATTACTTTGCTATGGAATGTAAGGAAGTGTGTGGTTTT | 286 |
| mir-208-prec | TGACGGGCGAGCTTTTGGCCCGGGTTATACCTGATGCTCACGTATAAGACGAGCAAAAAGCTTGTTGGTCA | 287 |
| mir-210-prec | ACCCGGCAGTGCCTCCAGGCGCAGGGCAGCCCCTGCCCACCGCACACTGCGCTGCCCCAGACCCACTGTGCGTGTGACAGCGGCTGATCTGTGCCTGGGCAGCGCGACCC | 288 |
| mir-211-prec | TCACCTGGCCATGTGACTTGTGGGCTTCCCTTTGTCATCCTTCGCCTAGGGCTCTGAGCAGGGCAGGGACAGCAAAGGGGTGCTCAGTTGTCACTTCCCACAGCACGGAG | 289 |
| mir-212-prec | CGGGGCACCCCGCCCGGACAGCGCGCCGGCACCTTGGCTCTAGACTGCTTACTGCCCGGGCCGCCCTCAGTAACAGTCTCCAGTCACGGCCACCGACGCCTGGCCCCGCC | 290 |
| mir-213-prec | CCTGTGCAGAGATTATTTTTTAAAAGGTCACAATCAACATTCATTGCTGTCGGTGGGTTGAACTGTGTGGACAAGCTCACTGAACAATGAATGCAACTGTGGCCCCGCTT | 291 |
| mir-213-prec-LIM | GAGTTTTGAGGTTGCTTCAGTGAACATTCAACGCTGTCGGTGAGTTTGGAATTAAAATCAAAACCATCGACCGTTGATTGTACCCTATGGCTAACCATCATCTACTCC | 292 |
| mir-214-prec | GGCCTGGCTGGACAGAGTTGTCATGTGTCTGCCTGTCTACACTTGCTGTGCAGAACATCCGCTCACCTGTACAGCAGGCACAGACAGGCAGTCACATGACAACCCAGCCT | 293 |
| mir-215-prec | ATCATTCAGAAATGGTATACAGGAAAATGACCTATGAATTGACAGACAATATAGCTGAGTTTGTCTGTCATTTCTTTAGGCCAATATTCTGTATGACTGTGCTACTTCAA | 294 |
| mir-216-prec | GATGGCTGTGAGTTGGCTTAATCTCAGCTGGCAACTGTGAGATGTTCATACAATCCCTCACAGTGGTCTCTGGGATTATGCTAAACAGAGCAATTTCCTAGCCCTCACGA | 295 |

TABLE 1 -continued

Human miR Gene Product Sequences

| Name | Precursor Sequence (5' to 3')* | SEQ ID NO: |
|---|---|---|
| mir-217-prec | AGTATAATTATTACATAGTTTTTGATGTCGCAGA<u>TACTGCA</u><br><u>TCAGGAACTGATTGGAT</u>AAGAATCAGTCACCATCAGTTCC<br>TAATGCATTGCCTTCAGCATCTAAACAAG | 296 |
| mir-218-1-prec | GTGATAATGTAGCGAGATTTTCTG<u>TTGTGCTTGATCTAACC</u><br><u>ATGT</u>GGTTGCGAGGTATGAGTAAAACATGGTTCCGTCAAG<br>CACCATGGAACGTCACGCAGCTTTCTACA | 297 |
| mir-218-2-prec | GACCAGTCGCTGCGGGGCTTTCCT<u>TTGTGCTTGATCTAACC</u><br><u>ATGT</u>GGTGGAACGATGGAAACGGAACATGGTTCTGTCAAG<br>CACCGCGGAAAGCACCGTGCTCTCCTGCA | 298 |
| mir-219-prec | CCGCCCCGGGCCGCGGCTCCTGA<u>TTGTCCAAACGCAATTC</u><br><u>T</u>CGAGTCTATGGCTCCGGCCGAGAGTTGAGTCTGGACGTC<br>CCGAGCCGCCGCCCCCAAACCTCGAGCGGG | 299 |
| mir-220-prec | GACAGTGTGGCATTGTAGGGCT<u>CCACACCGTATCTGACAC</u><br><u>TTT</u>GGGCGAGGGCACCATGCTGAAGGTGTTCATGATGCGG<br>TCTGGGAACTCCTCACGGATCTTACTGATG | 300 |
| mir-221-prec | TGAACATCCAGGTCTGGGGCATGAACCTGGCATACAATGT<br>AGATTTCTGTGTTCGTTAGGCAAC<u>AGCTACATTGTCTGCTG</u><br><u>GGTTTC</u>AGGCTACCTGGAAACATGTTCTC | 301 |
| mir-222-prec | GCTGCTGGAAGGTGTAGGTACCCTCAATGGCTCAGTAGCC<br>AGTGTAGATCCTGTCTTTCGTAATCAG<u>AGCTACATCTGGC</u><br><u>TACTGGGTCTC</u>TGATGGCATCTTCTAGCT | 302 |
| mir-223-prec | CCTGGCCTCCTGCAGTGCCACGCTCCGTGTATTTGACAAG<br>CTGAGTTGGACACTCCATGTGGTAGAG<u>TGTCAGTTTGTCA</u><br><u>AATACCCC</u>AAGTGCGGCACATGCTTACCAG | 303 |
| mir-224-prec | GGGCTTT<u>CAAGTCACTAGTGGTTCCGTTTA</u>GTAGATGATTG<br>TGCATTGTTTCAAAATGGTGCCCTAGTGACTACAAAGCCC | 304 |
| mir-29b-1 =<br>102-prec1 | CTTCTGGAAGCTGGTTTCACATGGTGGCTTAGATTTTTCCA<br>TCTTTGTATC<u>TAGCACCATTTGAAATCAGT</u>GTTTTAGGAG | 305 |
| mir-29b-2<br>(miR-29b-3) =<br>102prec7.1 = 7.2 | CTTCAGGAAGCTGGTTTCATATGGTGGTTTAGATTTAAATA<br>GTGATTGTC<u>TAGCACCATTTGAAATCAGT</u>GTTCTTGGGGG | 306 |
| mir-30* =<br>mir-097-prec-6 | GTGAGCGAC<u>TGTAAACATCCTCGACTGGAAGC</u>TGTGAAGC<br>CACAGATGGGCTTTCAGTCGGATGTTTGCAGCTGCCTACT | 307 |
| mir-033b | ACCAAGTTTCAGTTCA<u>TGTAAACATCCTACACTCAGCTGT</u><br>AATACATGGATTGGCTGGGAGGTGGATGTTTACTTCAGCT<br>GACTTGGA | 308 |
| mir-101-<br>precursor-9<br>(mir-101-3) | TGCCCTGGCTCAGTTATCACAGTGCTGATGCTGTCTATTCT<br>AAAGG<u>TACAGTACTGTGATAACTGAAGG</u>ATGGCA | 309 |
| mir-108-1-small | ACACTGCAAGAACAATAAGGATTTTTAGGGGCATTATGAC<br>TGAGTCAGAAAACACAGCTGCCCCTGAAAGTCCCTCATTT<br>TTCTTGCTGT | 310 |
| mir-108-2-small | ACTGCAAGAGCAATAAGGATTTTTAGGGGCATTATGATAG<br>TGGAATGGAAACACATCTGCCCCCAAAAGTCCCTCATTTT | 311 |
| mir-123-prec-1<br>(mir-126-prec-1) | CGCTGGCGACGGGACATTATTACTTTTGGTACGCGCTGTG<br>ACACTTCAAAC<u>TCGTACCGTGAGTAATAATGCG</u>CCGTCCA<br>CGGCA | 312 |
| mir-123-prec-2<br>(mir-126-prec-2) | A<u>CATTATTACTTTTGGTACGCG</u>CTGTGACACTTCAAACTCG<br>TACCGTGAGTAATAATGCGC | 313 |
| mir-129-1-prec | TGGATC<u>TTTTTGCGGTCTGGGCTTGC</u>TGTTCCTCTCAACAG<br>TAGTCAGGAAGCCCTTACCCCAAAAAGTATCTA | 314 |
| mir-129-2 | TGCCCTTCGCGAATCTTTTTGCGGTCTGGGCTTGCTGTACA<br>TAACTCAATAGCCGGAAGCCCTTACCCCAAAAAGCATTTG<br>CGGAGGGCG | 315 |

TABLE 1 -continued

Human miR Gene Product Sequences

| Name | Precursor Sequence (5' to 3')* | SEQ ID NO: |
|---|---|---|
| mir-133b-small | GCCCCCTGCTCTGGCTGGTCAAACGGAACCAAGTCCGTCT TCCTGAGAGGTTTGGTCCCCTTCAACCAGCTACAGCAGGG | 316 |
| mir-135-small-2 | AGATAAATTCACTCTAGTGCTT<u>TATGGCTTTTTATTCCTAT GTGAT</u>AGTAATAAAGTCTCATGTAGGGATGGAAGCCATGA AATACATTGTGAAAAATCA | 317 |
| mir-148b-small | AAGCACGATTAGCATTTGAGGTGAAGTTCTGTTATACACT CAGGCTGTGGCTCTCTGAAAGTCAGTGCAT | 318 |
| mir-151-prec | CCTGTCCTCAAGGAGCTTCAGTCTAGTAGGGGATGAGACA TACTAGACTGTGAGCTCCTCGAGGGCAGG | 319 |
| mir-155-prec(BIC) | CTGT<u>TAATGCTAATCGTGATAGGGG</u>TTTTTGCCTCCAACTG ACTCCTACATATTAGCATTAACAG | 320 |
| mir-156 = mir-157 = overlap mir-141 | CCTAACACTGTCTGGTAAAGATGGCTCCCGGGTGGGTTCT CTCGGCAGTAACCTTCAGGGAGCCCTGAAGACCATGGAGG AC | 321 |
| mir-158-small = mir-192 | GCCGAGACCGAGTGCACAGGGCT<u>CTGACCTATGAATTGAC</u> AGCCAGTGCTCTCGTCTCCCCTCTGGCTGCCAATTCCATAG GTCACAGGTATGTTCGCCTCAATGCCAGC | 322 |
| mir-159-1-small | TCCCGCCCCCTGTAACAGCAACTCCATGTGGAAGTGCCCA CTGGTTCCAGTGGGGCTGCTGTTATCTGGGGCGAGGGCCA | 323 |
| mir-161-small | AAAGCTGGGTTGAGAGGGCGAAAAAGGATGAGGTGACTG GTCTGGGCTACGCTATGCTGCGGCGCTCGGG | 324 |
| mir-163-1b-small | CATTGGCCTCCTAAGCCAGGGATTGTGGGTTCGAGTCCCA CCCGGGGTAAAGAAAGGCCGAATT | 325 |
| mir-163-3-small | CCTAAGCCAGGGATTGTGGGTTCGAGTCCCACCTGGGGTA GAGGTGAAAGTTCCTTTTACGGAATTTTTT | 326 |
| mir-175-small = mir-224 | GGGCTTTCAAGTCACTAGTGGTTCCGTTTAGTAGATGATTG TGCATTGTTTCAAAATGGTGCCCTAGTGACTACAAAGCCC | 327 |
| mir-177-small | ACGCAAGTGTCCTAAGGTGAGCTCAGGGAGCACAGAAAC CTCCAGTGGAACAGAAGGGCAAAAGCTCATT | 328 |
| mir-180-small | CATGTGTCACTTTCAGGTGGAGTTTCAAGAGTCCCTTCCTG GTTCACCGTCTCCTTTGCTCTTCCACAAC | 329 |
| mir-187-prec | GGTCGGGCTCACCATGACACAGTGTGAGACTCGGGCTACA ACACAGGACCCGGGGCGCTGCTCTGACCCC<u>TCGTGTCTTG TGTTGCAGCCGG</u>AGGGACGCAGGTCCGCA | 330 |
| mir-188-prec | TGCTCCCTCTCTCACAT<u>CCCTTGCATGGTGGAGGGT</u>GAGCT TTCTGAAAACCCCTCCCACATGCAGGGTTTGCAGGATGGC GAGCC | 331 |
| mir-190-prec | TGCAGGCCTCTGT<u>GTGATATGTTTGATATATTAGGTTGTTA</u> TTTAATCCAACTATATATCAAACATATTCCTACAGTGTCTT GCC | 332 |
| mir-197-2 | GTGCATGTGTATGTATGTGTGCATGTGCATGTGTATGTGTA TGAGTGCATGCGTGTGTGC | 333 |
| mir-197-prec | GGCTGTGCCGGGTAGAGAGGGCAGTGGGAGGTAAGAGCT CTTCACCCT<u>TCACCACCTTCTCCACCCAGC</u>ATGGCC | 334 |
| mir-202-prec | GTTCCTTTTTCCTATGCATATACTTCTTTGAGGATCTGGCC TAA<u>AGAGGTATAGGGCATGGGAAGA</u>TGGAGC | 335 |
| mir-294-1 (chr16) | CAATCTTCCTTTATCATGGTATTGATTTTTCAGTGCTTCCCT TTTGTGTGAGAGAAGATA | 336 |
| mir-hes1 | ATGGAGCTGCTCACCCTGTGGGCCTCAAATGTGGAGGAAC TATTCTGATGTCCAAGTGGAAAGTGCTGCGACATTTGAGC GTCACCGGTGACGCCCATATCA | 337 |

TABLE 1 -continued

Human miR Gene Product Sequences

| Name | Precursor Sequence (5' to 3')* | SEQ ID NO: |
|---|---|---|
| mir-hes2 | GCATCCCCTCAGCCTGTGGCACTCAAACTGTGGGGGCACT TTCTGCTCTCTGGTGAAAGTGCCGCCATCTTTTGAGTGTTA CCGCTTGAGAAGACTCAACC | 338 |
| mir-hes3 | CGAGGAGCTCATACTGGGATACTCAAAATGGGGCGCTTT CCTTTTTGTCTGTTACTGGGAAGTGCTTCGATTTTGGGGTG TCCCTGTTTGAGTAGGGCATC | 339 |
| mir-29b-1 | CTTCAGGAAGCTGGTTTCATATGGTGGTTTAGATTTAAATA GTGATTGTCTAGCACCATTTGAAATCAGTGTTCTTGGGGG | 340 |

*An underlined sequence within a precursor sequence represents a processed miR transcript (mature microRNA). All sequences are human.

Methods of Diagnosis and Prognosis

BCL2-associated cancers can be diagnosed or prognosticated by detecting a reduction in the amount of miR gene product in a sample relative to a control sample, a reduction in miR gene copy number, or by detecting mutations in one or more copies of a miR gene, wherein the miR gene comprises a nucleotide sequence that is complementary to the nucleotide sequence in a BCL2 gene transcript (e.g., as described herein). A reduction in miR gene copy number of a miR gene that comprises a nucleotide sequence that is complementary to the nucleotide sequence in a BCL2 gene transcript, from diploid to haploid, or to no copies, is diagnostic or prognostic of BCL2-associated cancers. Likewise, a mutation in one or both copies of a miR gene that comprises a nucleotide sequence that is complementary to the nucleotide sequence in a BCL2 gene transcript implies a loss of gene function, and is diagnostic or prognostic of BCL2-associated cancers.

As used herein, a "CLL cell" can be a lymphocyte from a subject who has, or is suspected of having, CLL, wherein the lymphocyte has a "CLL Score" of at least 4, as determined according to the scoring system of Matutes et al., *Leukemia* 8(10):1640-1645 (1994), the entire disclosure of which is herein incorporated by reference. As used herein, a "prostate cancer cell" can be a neoplastic or tumorigenic cell of prostate origin, whether or not located in the prostate. Other BCL2-associated cancer cells are known in those of skill in the art and/or are described herein.

The nucleic acid sequences of the miR15 and miR16 genes are contained within clone 317g11, the nucleotide sequence of which is given in GenBank Accession No.: AC069475. The entire disclosure of GenBank Accession No.: AC069475 is incorporated herein by reference. A deletion or mutation in a miR gene that comprises a nucleotide sequence that is complementary to the nucleotide sequence in a BCL2 gene transcript can be detected by determining the structure or sequence of the gene in tissue from a subject suspected of having a BCL2-associated cancer (e.g., CLL, acute myeloid leukemia, multiple myeloma, melanoma, follicular lymphoma, large cell lymphoma, non-Hodgkin's lymphoma, non-small cell lung carcinoma, hematologic malignancies, solid tumors, colorectal cancer, brain carcinoma, breast carcinoma, prostate carcinoma, Epstein-Barr virus-associated lymphoproliferative disease, renal carcinoma, hepatocellular carcinoma and gastric carcinoma), and comparing this with the structure or sequence of these genes in a sample of unaffected tissue from the subject, or in a sample of tissue from a normal control. Such a comparison can be made by any suitable technique (e.g., as described herein).

In one embodiment, to diagnose a BCL2-associated cancer, a tissue sample is derived from a subject. The sample is then prepared for determination of miR gene product expression or deletion or mutation of one or more miR genes. Suitable tissue samples include, but are not limited to, a biopsy of interest, as well as a blood and/or fluid sample.

As used herein, a "BCL2-associated cancer" is a cancer that is associated with overexpression of a BCL2 gene or gene product, which can be any cancer that is characterized by cells that express a higher level of one or more BCL2 gene products, relative to suitable control cells. Suitable control cells can be cells from an individual who is not affected with a Bcl2 over-expressing cancer, or they may be non-cancerous cells from either the subject in need, or they may be non-cancerous cells from another individual who is affected with a Bcl2 over-expressing cancer.

The presence of miR gene deletions or mutations can be detected by Southern blot hybridization of the genomic DNA from a subject, using probes for miR genes, e.g., as described herein. For example, a sample of tissue can be removed from a subject suspected of having a BCL2-associated cancer by conventional biopsy techniques. Alternatively, a blood sample can be removed from a subject suspected of having a BCL2-associated cancer, and white blood cells isolated for DNA extraction. The blood or tissue sample can be obtained from the patient prior to initiation of radiotherapy or chemotherapy. A corresponding tissue or blood sample can be obtained from unaffected tissues of the subject, or from a normal human individual, for use as a control.

Southern blot hybridization techniques are within the skill in the art. For example, genomic DNA isolated from a tissue or fluid (e.g., blood) from a subject suspected of having a BCL2-associated cancer can be digested with restriction endonucleases. This digestion generates restriction fragments of the genomic DNA, which can be separated by electrophoresis, for example, on an agarose gel. The restriction fragments are then blotted onto a hybridization membrane (e.g., nitrocellulose, nylon), and hybridized with labeled probes specific for one or more miR genes (e.g., a miR gene that comprises a nucleotide sequence that is complementary to the nucleotide sequence in a BCL2 gene transcript). A deletion or mutation of the one or more genes is indicated by an alteration of the restriction fragment patterns on the hybridization membrane, as compared to a control DNA sample that has been treated identically to the DNA sample from the subject. Probe labeling and hybridization conditions suitable for detecting the gene copy number of a miR gene or mutations within a miR gene can be readily determined by one of ordinary skill in the art. The term "deletion," as used herein, refers to partial deletion of a gene or to deletion of the entire gene.

For example, miR-15a and miR-16-1 nucleic acid probes for Southern blot hybridization can be designed based upon the published sequence of the miR-15a and miR-16-1 microRNAs, as described in Lagos-Quintana et al., *Science* 294: 853-858 (2001), the entire disclosure of which is incorporated herein by reference. The nucleotide sequence of the miR-15a microRNA is uagcagcacauaauggguuugug (SEQ ID NO:3). The nucleotide sequence of the miR-16-1 microRNA is uagcagcacguaaauauuggcg (SEQ ID NO:4). Suitable probes for detecting miR-15a and miR-16-1 DNA are, respectively:

```
                                    (SEQ ID NO: 5)
          CACAAACCATTATGTGCTTGCTA (SEQ ID NO: 6)
          GCCAATATTTACGTGCTGCTA
```

The complements of SEQ ID NO:5 and SEQ ID NO:6 can also be used to probe for miR-15a or miR-16-1 DNA. Other suitable probes for detecting miR-15a, miR-16-1 or other miR genes (e.g., miR genes that comprise a nucleotide sequence that is complementary to the nucleotide sequence in a BCL2 gene transcript) can easily be determined by one of skill in the art.

Methods for preparation of labeled DNA and RNA probes, and the conditions for hybridization thereof to target nucleotide sequences, are described in *Molecular Cloning: A Laboratory Manual*, J. Sambrook et al., eds., 2nd edition, Cold Spring Harbor Laboratory Press, 1989, Chapters 10 and 11, the disclosures of which are herein incorporated by reference.

For example, the nucleic acid probe can be labeled with, e.g., a radionuclide, such as $^3$H, $^{32}$P, $^{33}$P, $^{14}$C, or $^{35}$S; a heavy metal; or a ligand capable of functioning as a specific binding pair member for a labeled ligand (e.g., biotin, avidin or an antibody), a fluorescent molecule, a chemiluminescent molecule, an enzyme or the like.

Probes can be labeled to high specific activity by either the nick translation method of Rigby et al., *J. Mol. Biol.* 113:237-251 (1977) or by the random priming method of Fienberg et al., *Anal. Biochem.* 132:6-13 (1983), the entire disclosures of both of which are herein incorporated by reference. The latter is the method of choice for synthesizing $^{32}$P-labeled probes of high specific activity from single-stranded DNA or from RNA templates. For example, by replacing preexisting nucleotides with highly radioactive nucleotides according to the nick translation method, it is possible to prepare $^{32}$P-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR15 or miR16 gene copy number. Alternatively, miR15 or miR16 gene copy number can be quantified by computerized imaging systems, such as the Molecular Dynamics 400-B 2D Phosphorimager that is available from Amersham Biosciences, Piscataway, N.J.

Where radionuclide labeling of DNA or RNA probes is not practical, the random-primer method can be used to incorporate a nucleotide analogue (e.g., the dTTP analogue, 5-(N—(N-biotinyl-epsilon-aminocaproyl)-3-aminoallyl)deoxyuridine triphosphate) into the probe molecule. The biotinylated probe oligonucleotide can be detected by reaction with biotin-binding proteins, such as avidin, streptavidin, or anti-biotin antibodies, coupled to fluorescent dyes or enzymes that produce color reactions.

Deletions or mutations of miR genes can also be detected by amplifying a fragment of these genes by polymerase chain reaction (PCR), and analyzing the amplified fragment by sequencing or by electrophoresis to determine if the sequence and/or length of the amplified fragment from a subject's DNA sample is different from that of a control DNA sample. Suitable reaction and cycling conditions for PCR amplification of DNA fragments can be readily determined by one of ordinary skill in the art. Exemplary PCR reaction and cycling conditions are provided in the methods described in the Examples below.

Diagnosis of a BCL2-associated cancer can be performed by detecting deletions of miR genes (e.g., miR genes that comprises a nucleotide sequence that is complementary to the nucleotide sequence in a BCL2 gene transcript). For example, detection of miRs between various chromosome markers, such as the markers indicated in FIGS. 2A-2D. For example, a deletion in the region of 13q14 between microsatellite markers D13S272 and D13S273 comprising miR-15a and miR-16-1, can indicate the presence of a BCL2-associated cancer. In addition, when the deletion in 13q14 is between microsatellite markers D13S1150 and D13S272 or between locus Alu18 and microsatellite marker D13S272, where miR15 or miR16 are deleted, the presence of a BCL2-associated cancer can be indicated.

An alternative method of determining the copy number of a miR gene that comprises a nucleotide sequence complementary to the nucleotide sequence in a BCL2 gene transcript (for example, miR-15a or miR-16-1 genes) per diploid genome in a sample of tissue relies on the fact that the miR-15a/miR-16-1 gene cluster is located in 13q14, and is linked to the markers D13S272 and D13S273. The loss of a copy of the miR-15a or miR-16-1 genes in an individual who is heterozygous at a locus linked to the D13S272 and D13S273 markers can be inferred from the loss of heterozygosity in these markers. Methods for determining loss of heterozygosity of chromosomal markers are within the skill in the art. An exemplary loss of heterozygosity study is described in Example 3 below.

Another technique for determining whether one or more miR genes in a subject suspected of having a BCL2-associated cancer is mutated is single strand conformational polymorphism (SSCP), for example, as described in Orita, et al., *Genomics* 5: 874-879 (1989) and Hayashi, *PCR Methods and Applic.* 1: 34-38 (1991), the entire disclosures of which are herein incorporated by reference. The SSCP technique consists of amplifying a fragment of the gene of interest (e.g., a miR gene) by PCR; denaturing the fragment and electrophoresing the two denatured single strands under non-denaturing conditions. The single strands assume a complex sequence-dependent intrastrand secondary structure that affects the strands electrophoretic mobility.

A deletion or mutation in one or more miR genes can also cause a reduction in expression of those miR genes. Thus, a BCL2-associated cancer can also be diagnosed by detecting expression levels of the RNA produced from one or more miR genes (e.g., a miR gene that comprises a nucleotide sequence that is complementary to the nucleotide sequence in a BCL2 gene transcript), where a reduction in miR gene expression is diagnostic of a BCL2-associated cancer.

miR genes are transcribed to produce a precursor RNA which forms a stem-loop structure. The precursor RNA is not translated into a protein, but is rather processed into a "micro RNA" or "miRNA," which is believed to be the functional gene product.

As used herein, a "miR gene product" means the processed or unprocessed RNA transcripts from a miR gene, as described more fully below. The terms "RNA," RNA transcripts," and "gene product," are used interchangeably herein in the context of miR gene expression.

For example, the miR-15a and miR-16-1 precursor RNAs are described in Lagos-Quintana, et al., *Science* 294, 853-858 (2001). The sequences of the miR-15a and miR-16-1 precursor RNAs are given as SEQ ID NO:1 and SEQ ID NO:2. The predicted stem-loop structures of SEQ ID NO:1 and SEQ ID NO:2, are shown in FIGS. 1A and 1B, respectively.

```
[SEQ ID NO: 1]:
ccuuggaguaaaguagcagcacauaaugguuugugga uuuugaaaaggugcaggccauauugugcugccucaaa aauacaagg

[SEQ ID NO: 2]:
gucagcagugccuuagcagcacguaaauauuggcguu aagauucuaaaauuaucuccaguauuaacugugcugc ugaaguaagguugac
```

Without wishing to be bound by any theory, it is believed that the miR-15a and miR16-1 precursor RNAs are co-expressed from the miR-15a/miR-16-1 gene cluster, and are processed by the Dicer/Argonaute complex into the functional miRNA products. See, e.g., Lee et al., *Science* 294: 862 (2001). Both functional miRNA products from these genes are single-stranded RNA molecules of 22 nucleotides in length which have a 5' terminal monophosphate and a 3' terminal hydroxyl group. The nucleotide sequence of the processed miR-15a microRNA is uagcagcacauaaugguuugug (SEQ ID NO:3). The nucleotide sequence of the processed miR-16-1 microRNA is uagcagcacguaaauauuggcg (SEQ ID NO:4). In the practice of embodiments of the invention, the 60-70 nt RNA precursor molecules produced from the miR-15a or miR-16-1 genes can be detected. Alternatively, the shorter miR-15a and miR-16-1 microRNA gene products, which are produced through processing of the precursor RNAs by the Dicer and Argonaute proteins, can be detected.

Methods for determining RNA expression levels are within the level of skill in the art. For example, a sample of tissue or blood from a subject suspected of having a BCL2-associated cancer is obtained as described herein. As a control, a corresponding tissue or blood sample can be obtained from unaffected tissues of the subject, or from a normal human individual, as described herein. The control tissue or blood sample is then processed along with the sample from the subject. The levels of miR gene expression (e.g., a miR gene that comprises a nucleotide sequence that is complementary to the nucleotide sequence in a BCL2 gene transcript) in the subject can then be compared to those from unaffected tissue from the subject, or to the miR expression level in tissue or blood from the normal control. For example, the relative miR expression level in BCL2-associated cancer cells are conveniently determined with respect to one or more standards. The standards may comprise, for example, a zero expression level on the one hand and the expression level of the gene in normal tissue of the same patient, or the expression level in the tissue of a normal control group on the other hand. The standard may also comprise the miR expression level in a standard cell line. In one embodiment, the magnitude of the decrement in miR expression, as compared to normal expression levels, is indicative of the future clinical outcome following treatment.

Alternatively, the levels of miR gene expression (e.g., a miR gene that comprises a nucleotide sequence that is complementary to the nucleotide sequence in a BCL2 gene transcript) in a subject suspected of having a BCL2-associated cancer can be compared to average levels of miR gene expression previously obtained for a population of normal human controls.

Suitable techniques for determining the level of RNA transcripts of a particular gene in cells are well known to those skilled in the art. According to one such method, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters, e.g., using the so-called "Northern" blotting technique. The RNA is then immobilized on the filters by heating. Detection and quantification of specific RNA is accomplished using appropriately labeled DNA or RNA probes complementary to the RNA in question. See, for example, *Molecular Cloning: A Laboratory Manual*, J. Sambrook et al., eds., 2nd edition, Cold Spring Harbor Laboratory Press, 1989, Chapter 7, the entire disclosure of which is incorporated by reference. Suitable probes for Northern blot hybridization of miR-15a or miR-16-1 RNA include, e.g., SEQ ID NO:5 and SEQ ID NO:6.

Autoradiographic detection of probe hybridization to miR RNA can be performed by exposing hybridized filters to photographic film. Densitometric scanning of the photographic films exposed by the hybridized filters provides an accurate measurement of RNA transcript levels. Alternatively, RNA transcript levels can be quantified by computerized imaging of the hybridization blot, for example, with the Molecular Dynamics 400-B 2D Phosphorimager that is available from Amersham Biosciences, Piscataway, N.J.

In addition to Northern and other RNA blotting hybridization techniques, the levels of RNA transcripts can be carried out according to the technique of in situ hybridization. This technique requires fewer cells than the Northern blotting technique, and involves depositing whole cells onto a microscope cover slip and probing the nucleic acid content of the cell with a solution containing radioactive or otherwise labeled oligonucleotide (e.g., cDNA or cRNA) probes. This technique is particularly well-suited for analyzing tissue biopsy samples from subjects suspected of having a BCL2-associated cancer (e.g., CLL, prostate cancer). The practice of the in situ hybridization technique is described in more detail in U.S. Pat. No. 5,427,916, the entire disclosure of which is incorporated herein by reference. Suitable probes for in situ hybridization of miR-15a or miR-16-1 RNA include, e.g., SEQ ID NO:5 and SEQ ID NO:6.

The relative number of a particular miR transcript can also be determined by reverse transcription of the miR transcript, followed by amplification in a polymerase chain reaction (RT-PCR). The levels of a miR transcript can be by comparing with an internal standard, for example, levels of mRNA from a "housekeeping" gene present in the same sample. Suitable "housekeeping" genes for use as an internal standard include, e.g., myosin and glyceraldehyde-3-phosphate dehydrogenase (G3PDH). The methods for quantitative RT-PCR and variations thereof are well known to those of skill in the art.

Other techniques for measuring expression of a miR gene transcript are also known to those of skill in the art and include various techniques for measuring the rates of RNA transcription and degradation.

Methods of Treatment

A BCL2-associated cancer can be treated by administering the isolated gene product of one or more miR genes (e.g., a miR gene that comprises a nucleotide sequence that is complementary to the nucleotide sequence in a BCL2 gene transcript), either alone or in combination, to a BCL2-associated cancer cell. Without wishing to be bound by any theory, it is believed that the miR gene products suppress the neoplastic or tumorigenic growth of such cancer cells.

In particular, a BCL2-associated cancer can be treated by administering the isolated gene product of one or more miR genes, either alone or in combination, to a cancer cell.

As used herein, a "BCL2-associated cancer cell" is a tumorigenic or neoplastic cell, which can be isolated from a subject suffering from a BCL2-associated cancer. A BCL2-associated cancer cell can be identified by detecting an increase in the expression level of a BCL2 gene product in a cell, relative to a normal control cell, or by detecting a cancerous or neoplastic phenotype in the cell. One skilled in the art can readily identify cells with a cancerous or neoplastic phenotype. For example, such cells are insensitive to contact-induced growth inhibition in culture, and will form foci when cultured for extended periods. Cancerous or neoplastic cells also exhibit characteristic morphological changes, disorganized patterns of colony growth and acquisition of anchorage-independent growth. Cancerous or neoplastic cells also have the ability to form invasive tumors in susceptible animals, which can be evaluated by injecting the cells, for example, into athymic mice using techniques within the skill in the art.

As used herein, an "isolated" gene product is one which is altered or removed from the natural state through human intervention. For example, an RNA naturally present in a living animal is not "isolated." A synthetic RNA, or an RNA partially or completely separated from the coexisting materials of its natural state, is "isolated." An isolated RNA can exist in substantially purified form, or can exist in a cell into which the RNA has been delivered. Thus, a miR gene product that is deliberately delivered to, or expressed in, a cell, (e.g., a BCL2-associated cancer cell) is considered an "isolated" gene product.

miR gene products can be obtained using a number of standard techniques. For example, the gene products can be chemically synthesized or recombinantly produced using methods known in the art. In one embodiment, the RNA products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, one or more miR gene products can be expressed from recombinant circular or linear DNA plasmids using any suitable promoter. Suitable promoters for expressing RNA from a plasmid include the U6 or H1 RNA pol III promoter sequences, or the cytomegalovirus (CMV) promoters. Selection of other suitable promoters is within the skill in the art. Such recombinant plasmids can also comprise inducible or regulatable promoters for expression of one or more miR gene products in cells (e.g., BCL2-associated cancer cells (e.g., CLL cells, prostate cancer cells, other cancer cells)).

miR gene products that are expressed from recombinant plasmids can be isolated from cultured cell expression systems by standard techniques. miR gene products that are expressed from recombinant plasmids can also be delivered to, and expressed directly in, cancer cells (e.g., BCL2-associated cancer cells (e.g., CLL cells, prostate cancer cells, other cancer cells)). The use of recombinant plasmids to deliver the miR gene products to cancer cells is discussed in more detail below.

Multiple miR gene products can be expressed from a separate recombinant plasmid, or can be expressed from the same recombinant plasmid. In one embodiment, the one or more miR gene products are expressed as the RNA precursor molecules from a single plasmid, and the precursor molecules are processed into functional miRNA molecules by a suitable processing system. Suitable processing systems include, e.g., the in vitro *Drosophila* cell lysate system described in U.S. Published Application No.: 2002/0086356, by Tuschl et al., the entire disclosure of which is herein incorporated by reference.

Selection of plasmids suitable for expressing a miR gene product, methods for inserting nucleic acid sequences that express a miR gene product into a plasmid, and methods of delivering a recombinant plasmid to the cells of interest are within the skill in the art. See, for example, Zeng, et al., *Molecular Cell* 9:1327-1333 (2002); Tuschl, *Nat. Biotechnol,* 20:446-448 (2002); Brummelkamp, et al., *Science* 296: 550-553 (2002); Miyagishi, et al., *Nat. Biotechnol.* 20:497-500 (2002); Paddison, et al., *Genes Dev.* 16:948-958 (2002); Lee, et al., *Nat. Biotechnol.* 20:500-505 (2002); and Paul, et al., *Nat. Biotechnol.* 20: 505-508 (2002), the entire disclosures of which are herein incorporated by reference.

In a particular embodiment, a plasmid expressing a miR gene product(s) comprises a sequence encoding the miR precursor RNA under the control of the cytomegalovirus (CMV) intermediate-early promoter. As used herein, "under the control" of a promoter means that the nucleic acid sequences encoding the miRNA product are located 3' of the promoter, so that the promoter can initiate transcription of the miRNA coding sequences.

miR gene products can also be expressed from recombinant viral vectors. It is contemplated that the miR gene product(s) can be expressed from two separate recombinant viral vectors, or from the same viral vector. The RNA expressed from the recombinant viral vectors can either be isolated from cultured cell expression systems by standard techniques, or can be expressed directly in BCL2-associated cancer cells. The use of recombinant viral vectors to deliver the miR gene product(s) to BCL2-associated cancer cells is discussed in more detail below.

The recombinant viral vectors comprise sequences encoding the one or more miR gene products and any suitable promoter for expressing the RNA sequences. As described herein, suitable promoters include, for example, the U6 or H1 RNA pol III promoter sequences, or the cytomegalovirus promoters. Selection of other suitable promoters is within the skill in the art. The recombinant viral vectors can also comprise inducible or regulatable promoters for expression of the one or more miR gene products in a BCL2-associated cancer cell.

Any viral vector capable of accepting a nucleotide sequence encoding a miR gene product can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector can be utilized in embodiments of the invention; it can be pseudotyped with surface proteins from vesicular stomatitis virus (VSV), rabies, Ebola, Mokola, and the like. Selection of suitable recombinant viral vectors, methods for inserting nucleic acid sequences for expressing RNA into the vector, methods of delivering the viral vector to the cells of interest, and recovery of the expressed RNA products are all within the skill in the art. See, for example, Dornburg, *Gene Therap.* 2:301-310 (1995); Eglitis, *Biotechniques* 6:608-614 (1988); Miller, *Hum. Gene Therap.* 1:5-14 (1990); and Anderson, *Nature* 392:25-30 (1998), the entire disclosures of which are herein incorporated by reference.

For some embodiments, preferred viral vectors are those derived from AV and AAV. A suitable AV vector for expressing the miRNA, a method for constructing the recombinant AV vector, and a method for delivering the vector into target cells, are described in Xia, et al., *Nat. Biotech.* 20:1006-1010 (2002), the entire disclosure of which is herein incorporated by reference. Suitable AAV vectors for expressing the miRNA, methods for constructing the recombinant AAV vector, and methods for delivering the vectors into target cells are described in Samulski, et al., *J. Virol.* 61:3096-3101 (1987); Fisher, et al., *J. Virol.*, 70:520-532 (1996); Samulski, et al., *J. Virol.* 63:3822-3826 (1989); U.S. Pat. No. 5,252,479; U.S. Pat. No. 5,139,941; International Patent Application No.: WO 94/13788; and International Patent Application No.: WO 93/24641, the entire disclosures of which are herein incorporated by reference. In a particular embodiment, one or more miR gene products are expressed from a single recombinant AAV vector comprising the CMV intermediate early promoter.

In one embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In particular embodiments, one or more miR gene products are used to inhibit the neoplastic or tumorigenic growth of BCL2-associated cancer cells (e.g., CLL cells, prostate cancer cells, other cancer cells). Without wishing to be bound by any one theory, it is believed that the processed miRNAs bind to complementary sequences in one or more target mRNAs that are necessary to initiate and/or maintain neoplastic or tumorigenic growth in these cells. Thus, embodiments of the invention provide a method of treating a BCL2-associated cancer, for example, CLL, acute myeloid leukemia, multiple myeloma, melanoma, follicular lymphoma, large cell lymphoma, non-Hodgkin's lymphoma, non-small cell lung carcinoma, hematologic malignancies, solid tumors, colorectal cancer, brain carcinoma, breast carcinoma, prostate carcinoma, Epstein-Barr virus-associated lymphoproliferative disease, renal carcinoma, hepatocellular carcinoma and gastric carcinoma, in a subject in need of such treatment. The method comprises administering an effective amount of one or more miR gene products to the subject, such that proliferation of BCL2-associated cancer cells is inhibited. In one embodiment, one or more miR gene products comprise a nucleotide sequence that is complementary to a nucleotide sequence within a BCL2 transcript.

For example, the expression of one or more miR genes may be reduced or absent in primary or metastatic tumor or neoplastic cells from cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia, chronic myelocytic leukemia, CLL).

Expression of the one or more miR genes may also be reduced or absent in cancers having their origin in at least the following organs or tissues, regardless of histologic subtype: breast; tissues of the male and female urogenital system (e.g. ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye.

Expression of the one or more miR genes may also be reduced or absent in cancers or tumors in any prognostic stage of development, for example, as measured by the "Overall Stage Groupings" (also called "Roman Numeral") or the "Tumor, Nodes, and Metastases" (TNM) staging systems. Appropriate prognostic staging systems and stage descriptions for a given cancer are known in the art, for example, as described in the National Cancer Institute's "CancerNet" Internet website.

A subject in need of treatment for a BCL2-associated cancer can be identified by obtaining a sample of tumor or neoplastic cells (or cells suspected of being tumor or neoplastic) from the subject, and determining whether the expression of one or more miR genes (e.g., miR genes that comprise a nucleotide sequence that is complementary to a nucleotide sequence within a BCL2 transcript) is reduced or absent in at least a portion of the cells, as compared to cells from normal tissue obtained from the subject (e.g., control cells). Methods for detecting miR gene expression levels in cells are within the skill in the art and are described herein. Alternatively, the expression of one or more miR gene products in cells obtained from a subject can be compared to average expression levels of these genes in cells obtained from a population of normal subjects. A subject in need of treatment for a BCL2-associated cancer can be readily identified by a physician using standard diagnostic techniques. See, e.g., "Chronic lymphocytic leukemia: recommendations for diagnosis, staging, and response criteria. International Workshop on Chronic Lymphocytic Leukemia," (1989) *Annals of Internal Medicine* 110(3):236-238, the entire disclosure of which is incorporated herein by reference. For example, subjects with CLL exhibit circulating CLL cells, lymphocytosis (i.e., lymphocyte counts in the blood equal to or higher than 10,000 cells per cubic millimeter), and a progressive accumulation of CLL cells in the bone marrow and lymphatic tissues.

The identity of BCL2-associated cancer cells in a subject's blood or other tissue can be confirmed by direct visual observation of a blood sample, and/or, in the case of CLL, by determining the "CLL Score" of lymphocytes. The CLL Score indicates the presence or absence of five lymphocyte surface markers characteristic of CLL cells: CD5+, CD23+, FMC7−, and weak expression (+/−) of surface immunoglobulin (SmIg) and CD22. This scoring system gives a value of 1 or 0 for each of these five markers according to whether it is typical or atypical for CLL. CLL cells have a CLL Score of 4 or 5, while lymphocytes from other leukemias have a CLL Score of <1 to 3. See Matutes, et al., *Leukemia* 8(10):1640-1645 (1994) and Moreau, et al., *American Journal of Clinical Pathology*, 108:378-82 (1997), the entire disclosures of which are herein incorporated by reference. CLL cells also have relatively low levels of surface-membrane immunoglobulin as compared with normal peripheral blood B cells. Surface-membrane immunoglobulin levels on lymphocytes can be readily detected according to standard techniques; see, e.g., Rozman, et al., *New England Journal of Medicine* 333:1052-1057 1995), the entire disclosure of which is herein incorporated by reference.

As used herein, an "effective amount" of a miR gene product is an amount sufficient to inhibit proliferation of a BCL2-associated cancer cell in a subject suffering from a BCL2-associated cancer. As used herein, "to inhibit the proliferation of a BCL2-associated cancer cell" means to kill the cell, or permanently or temporarily arrest the growth of the cell. Inhibition of a BCL2-associated cancer cell can be inferred if the number of such cells in the subject remains constant or decreases after administration of a miR gene product. An inhibition of BCL2-associated cancer cell proliferation can also be inferred if the absolute number of such cells increases, but the rate of tumor growth decreases.

The number of BCL2-associated cancer cells in a subject's body can be determined by direct measurement, or by estimation from the size of primary or metastatic tumor masses.

For example, the number of BCL2-associated cancer cells in a subject can be readily determined using a whole blood or white blood cell count. The number of BCL2-associated cancer cells can also be readily determined by immunohistological methods, flow cytometry, or other techniques designed to detect the characteristic surface markers of BCL2-associated cancer cells.

The size of a tumor mass can be ascertained by direct visual observation, or by diagnostic imaging methods, such as X-ray, magnetic resonance imaging (MRI), ultrasound, and scintigraphy. Diagnostic imaging methods used to ascertain the size of a tumor mass can be employed with or without contrast agents, as is known in the art. The size of a tumor mass can also be ascertained by physical means, such as palpation of the tissue mass or measurement of the tissue mass with a measuring instrument, such as a caliper.

One skilled in the art can readily determine an effective amount of the one or more miR gene products to be administered to a given subject, by taking into account factors, such as the size and weight of the subject; the extent of disease penetration; the age, health and sex of the subject; the route of administration; and whether the administration is regional or systemic.

For example, an effective amount of a miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the one or more miR gene products, based on the weight of a tumor mass, can be at least about 10 micrograms/gram of tumor mass, and can be between about 10-500 micrograms/gram of tumor mass. In addition, the effective amount can be at least about 60 micrograms/gram of tumor mass or at least about 100 micrograms/gram of tumor mass. In a particular embodiment, an effective amount, based on the weight of the tumor mass, is injected directly into the tumor.

An effective amount of the one or more miR gene products can also be based on the approximate or estimated body weight of a subject to be treated. In one embodiment, such effective amounts are administered parenterally or enterally, as described herein. For example, an effective amount of the one or more miR gene products administered to a subject can range from about 5-3000 micrograms/kg of body weight, and can be between about 700-1000 micrograms/kg of body weight, and also can be greater than about 1000 micrograms/kg of body weight.

One skilled in the art can also readily determine an appropriate dosage regimen for the administration of one or more miR gene products to a given subject. For example, one or more miR gene products can be administered to the subject once (e.g., as a single injection or deposition). Alternatively, the one or more miR gene products can be administered once or twice daily to a subject for a period of from about three to about twenty-eight days, more preferably from about seven to about ten days. In a particular dosage regimen, the one or more miR gene products are administered once a day for seven days. Where a dosage regimen comprises multiple administrations, it is understood that the effective amount of the one or more miR gene products administered to the subject can comprise the total amount of gene product administered over the entire dosage regimen.

One or more miR gene products can be administered to a subject by any means suitable for delivering the gene products to cells of the subject, such as hematopoietic stem cells (HSCs) and/or BCL2-associated cancer cells (e.g., CLL cells, prostate cancer cells, other cancer cells)). For example, one or more miR gene products can be administered by methods suitable to transfect cells of the subject with a miR gene product, or with a nucleic acid comprising a sequence encoding a miR gene product. The cells can be transfected directly with one or more miR gene products (as these are nucleic acids), or can be transfected with nucleic acids comprising sequences encoding the one or more miR gene products. In one embodiment, the cells are transfected with a plasmid or viral vector comprising sequences encoding the one or more miR gene products, as described herein.

Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of many embodiments of the invention; acceptable results may be achieved with 0.1-100 micrograms of nucleic acid/ $10^5$ cells. For example, a ratio of about 0.5 micrograms of plasmid vector in 3 micrograms of DOTAP per $10^5$ cells can be used.

In one embodiment, BCL2-associated cancer cells, for example, CLL or prostate cancer cells, are isolated from the subject, transfected with a nucleic acid encoding a miR gene product, and reintroduced into the subject. In a particular embodiment, the transfected and reimplanted cells are CLL cells. In another embodiment, the transfected and reimplanted cells are HSCs from a subject who has been diagnosed with a BCL2-associated cancer.

Techniques for isolating BCL2-associated cancer cells (e.g., CLL cells) from a subject are within the skill in the art, for example, as described in the Examples below. Techniques for isolating, identifying, separating, and culturing HSCs from a subject are also within the skill in the art, for example, as disclosed in U.S. Pat. Nos. 5,635,387 and 5,643,741, and Campana, et al., *Blood* 85:1416-1434 (1995), the entire disclosures of which are incorporated herein by reference. In one embodiment, harvested bone marrow is purged of tumorigenic or neoplastic cells prior to transfection of the HSCs. Suitable purging techniques include, for example, leukopheresis of mobilized peripheral blood cells, immunoaffinity-based selection or killing of tumor cells, or the use of cytotoxic or photosensitizing agents to selectively kill tumor cells, as are known in the art. See, for example, Bone Marrow Processing and Purging, Part 5 (A. Gee, ed.), CRC Press, Boca Raton, Fla., 1991; Lydaki, et al., *J. Photochem. and Photobiol.* 32:27-32 (1996); and Gazitt, et al., *Blood* 86:381-389 (1995), the entire disclosures of which are herein incorporated by reference.

The isolated cells (e.g., HSC cells, BCL2-associated cancer cells (e.g., CLL cells, prostate cancer cells, other cancer cells)) can be transfected by any suitable technique, as discussed herein. After transfection, a portion of the cells can be examined to confirm the presence of appropriate expression levels of the gene products. Once appropriate expression of a miR gene product has been confirmed, the remaining transfected cells can then be reintroduced into the subject. Transfected cells can be reintroduced into the subject by parenteral methods, including intravenous infusion or direct injection into the bone marrow. The transfected cells are preferably reintroduced into the subject in a saline solution or other pharmaceutically acceptable carrier. A suitable number of transfected cells for reintroduction is from about $10^5$ to about $10^8$ cells per kilogram of subject body weight. The number of transfected cells available for re-introduction can be increased by expanding the cells in culture prior to transfection.

In one embodiment, the genome of the cell (e.g., HSC cells, BCL2-associated cancer cells (e.g., CLL cells, prostate cancer cells, other cancer cells)) is transfected with a nucleic acid comprising a sequence that encodes a miR gene product, e.g., a plasmid expression vector, that stably integrates into the genome of the cell to provide long-term expression of the miR. Stable integration and expression can be confirmed by techniques known in the art, such as Southern blot analysis of genomic DNA using a miR gene cDNA (or fragments thereof) as a probe. Expression of a miR gene product can also be detected by standard Northern blot techniques. The cells that are stably transfected with a sequence encoding the miR gene product continue to express the miR gene product once they are re-implanted into the subject. An exemplary method of isolating HSC from a subject, transfecting them with plasmids expressing one or more miR gene products, and reimplanting the transfected HSC into the subject is described in the Examples below.

A miR gene product can also be administered to a subject by any suitable enteral or parenteral administration route. Suitable enteral administration routes for the present methods include oral, rectal, or intranasal delivery. Suitable parenteral administration routes include intravascular administration (e.g. intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition including subcutaneous infusion (such as by osmotic pumps); direct application to the tissue of interest, for example, by a catheter or other placement device (e.g., a retinal pellet or a suppository or an implant comprising a porous, non-porous, or gelatinous material); and inhalation. In one embodiment, a miR gene product is administered by injection or infusion. For the treatment of BCL2-associated cancers that involve solid tumors, a miR gene product can be administered by direct injection into the tumor.

In the present methods, a miR gene product can be administered to the subject either as naked RNA, in conjunction with a delivery reagent, or as a nucleic acid (e.g., a recombinant plasmid or viral vector) comprising a sequence that expresses the gene product. Suitable delivery reagents for administration of the miR gene product include, e.g., the Mirus Transit TKO lipophilic reagent; lipofectin; lipofectamine; cellfectin; polycations (e.g., polylysine); and liposomes.

Recombinant plasmids comprising sequences that express a miR gene product are discussed herein. Recombinant viral vectors comprising sequences that express a miR gene product are also discussed herein, and methods for delivering such vectors to cells (e.g., HSC cells, BCL2-associated cancer cells (e.g., CLL cells, prostate cancer cells, other cancer cells)) of a subject are within the skill in the art.

In a particular embodiment, liposomes are used to deliver a miR gene product, or a nucleic acid comprising a sequence encoding a miR gene product, to a subject. Liposomes can also increase the blood half-life of a miR gene product or nucleic acid. In the practice of this embodiment of the invention, a miR gene product, or nucleic acid comprising a sequence encoding a miR gene product, is encapsulated in liposomes prior to administration to the subject.

Liposomes suitable for use in embodiments of the invention can be formed from standard vesicle-forming lipids, which generally include neutral or negatively charged phospholipids, and a sterol, such as cholesterol. The selection of lipids is generally guided by consideration of factors, such as the desired liposome size and half-life of the liposomes in the blood stream. A variety of methods are known for preparing liposomes, for example, as described in Szoka, et al., *Ann. Rev. Biophys. Bioeng.* 9:467 (1980); and U.S. Pat. Nos. 4,235,871, 4,501,728, 4,837,028, and 5,019,369, the entire disclosures of which are herein incorporated by reference.

The liposomes encapsulating a miR gene product, or a nucleic acid comprising a sequence encoding a miR gene product, can comprise a ligand molecule that targets the liposome to a BCL2-associated cancer cell (e.g., a CLL cell, an HSC cell, a prostate cancer cell, another cancer cell). In one embodiment, a ligand that binds to a receptor that is prevalent in such cancer cells (e.g., a monoclonal antibody that binds to a tumor cell antigen or a cancer cell surface marker) is used.

The liposomes encapsulating a miR gene product, or a nucleic acid comprising a sequence encoding a miR gene product, can also be modified so as to avoid clearance by the mononuclear macrophage system ("MMS") and reticuloendothelial system ("RES"). Such modified liposomes can have opsonization-inhibition moieties on the surface or incorporated into the liposome structure. In one embodiment, a liposome for use in embodiments of the invention can comprise both opsonization-inhibition moieties and a ligand.

Opsonization-inhibiting moieties for use in preparing the liposomes are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In one embodiment, the opsonization-inhibiting moiety is a PEG, PPG, or a derivative thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio, at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al., *Proc. Natl. Acad. Sci., USA,* 18: 6949-53 (1988). In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products, or nucleic acids comprising sequences encoding the gene products, to tumor cells.

As described herein, in one embodiment, the invention is a method of preventing or treating a cancer associated with overexpression of a BCL2 gene or gene product (e.g., RNA, protein) in a subject in need of such treatment, comprising administering an effective amount of at least one miR gene product to the subject. The Bcl2 protein and members of the Bcl2 family, as well as their role in cancer, are described in Cory, S., and Adams, J. M., *Nature Reviews* 2: 647-656 (2002) and Sanchez-Beato, M., et al., *Blood* 101: 1220-1235 (2003), the contents of which are incorporated herein by reference. The nucleotide and amino acid sequences for a human BCL2 cDNA and protein are shown in Table 2.

TABLE 2

BCL2 cDNA and protein sequences.

| Name | Sequence | SEQ ID NO: |
|---|---|---|
| BCL2 cDNA (Genbank Ace. No. NM_0006 | TTTCTGTGAAGCAGAAGTCTGGGAATCGATCTGGAAATCCTCCTAATT TTTACTCCCTCTCCCCGCGACTCCTGATTCATTGGGAAGTTTCAAATC AGCTATAACTGGAGAGTGCTGAAGATTGATGGGATCGTTGCCTTATGC ATTTGTTTTGGTTTTACAAAAAGGAAACTTGACAGAGGATCATGCTGT ACTTAAAAAATACAACATCACAGAGGAAGTAGACTGATATTAACAATA CTTACTAATAATAACGTGCCTCATGAAATAAAGATCCGAAAGGAATTG GAATAAAAATTTCCTGCATCTCATGCCAAGGGGGAAACACCAGAATCA AGTGTTCCGCGTGATTGAAGACACCCCCTCGTCCAAGAATGCAAAGCA CATCCAATAAAATAGCTGGATTATAACTCCTCTTCTTTCTCTGGGGGC CGTGGGGTGGGAGCTGGGGCGAGAGGTGCCGTTGGCCCCCGTTGCTTT TCCTCTGGGAAGGATGGCGCACGCTGGGAGAACAGGGTACGATAACCG GGAGATAGTGATGAAGTACATCCATTATAAGCTGTCGCAGAGGGGCTA CGAGTGGGATGCGGGAGATGTGGGCGCCGCGCCCCGGGGCCGCCCC CGCACCGGGCATCTTCTCCTCCCAGCCCGGGCACACGCCCCATCCAGC CGCATCCCGGGACCCGGTCGCCAGGACCTCGCCGCTGCAGACCCCGGC TGCCCCCGGCGCCGCCGCGGGGCCTGCGCTCAGCCCGGTGCCACCTGT GGTCCACCTGACCCTCCGCCAGGCCGGCGACGACTTCTCCCGCCGCTA CCGCCGCGACTTCGCCGAGATGTCCAGCCAGCTGCACCTGACGCCCTT CACCGCGCGGGGACGCTTTGCCACGGTGGTGGAGGAGCTCTTCAGGGA CGGGGTGAACTGGGGGAGGATTGTGGCCTTCTTTGAGTTCGGTGGGGT CATGTGTGTGGAGAGCGTCAACCGGGAGATGTCGCCCCTGGTGGACAA | 55 |

TABLE 2-continued

BCL2 cDNA and protein sequences.

| Name | Sequence | SEQ ID NO: |
|---|---|---|
| | CATCGCCCTGTGGATGACTGAGTACCTGAACCGGCACCTGCACACCTG | |
| | GATCCAGGATAACGGAGGCTGGGATGCCTTTGTGGAACTGTACGGCCC | |
| | CAGCATGCGGCCTCTGTTTGATTTCTCCTGGCTGTCTCTGAAGACTCT | |
| | GCTCAGTTTGGCCCTGGTGGGAGCTTGCATCACCCTGGGTGCCTATCT | |
| | GGGCCACAAGTGAAGTCAACATGCCTGCCCCAAACAAATATGCAAAAG | |
| | GTTCACTAAAGCAGTAGAAATAATATGCATTGTCAGTGATGTACCATG | |
| | AAACAAAGCTGCAGGCTGTTTAAGAAAAAATAACACACATATAAACAT | |
| | CACACACACAGACAGACACACACACACAACAATTAACAGTCTTCAG | |
| | GCAAAACGTCGAATCAGCTATTTACTGCCAAAGGGAAATATCATTTAT | |
| | TTTTTACATTATTAAGAAAAAAGATTTATTTATTTAAGACAGTCCCA | |
| | TCAAAACTCCTGTCTTTGGAAATCCGACCACTAATTGCCAAGCACCGC | |
| | TTCGTGTGGCTCCACCTGGATGTTCTGTGCCTGTAAACATAGATTCGC | |
| | TTTCCATGTTGTTGGCCGGATCACCATCTGAAGAGCAGACGGATGGAA | |
| | AAAGGACCTGATCATTGGGGAAGCTGGCTTTCTGGCTGCTGGAGGCTG | |
| | GGGAGAAGGTGTTCATTCACTTGCATTTCTTTGCCCTGGGGCTGTGA | |
| | TATTAACAGAGGGAGGGTTCCTGTGGGGGAAGTCCATGCCTCCCTGG | |
| | CCTGAAGAAGAGACTCTTTGCATATGACTCACATGATGCATACCTGGT | |
| | GGGAGGAAAAGAGTTGGGAACTTCAGATGGACCTAGTACCCACTGAGA | |
| | TTTCCACGCCGAAGGACAGCGATGGGAAAAATGCCCTTAAATCATAGG | |
| | AAAGTATTTTTTTAAGCTACCAATTGTGCCGAGAAAAGCATTTTAGCA | |
| | ATTTATACAATATCATCCAGTACCTTAAGCCCTGATTGTGTATATTCA | |
| | TATATTTTGGATACGCACCCCCCAACTCCCAATACTGGCTCTGTCTGA | |
| | GTAAGAAACAGAATCCTCTGGAACTTGAGGAAGTGAACATTTCGGTGA | |
| | CTTCCGCATCAGGAAGGCTAGAGTTACCCAGAGCATCAGGCCGCCACA | |
| | AGTGCCTGCTTTTAGGAGACCGAAGTCCGCAGAACCTGCCTGTGTCCC | |
| | AGCTTGGAGGCCTGGTCCTGGAACTGAGCCGGGGCCCTCACTGGCCTC | |
| | CTCCAGGGATGATCAACAGGGCAGTGTGGTCTCCGAATGTCTGGAAGC | |
| | TGATGGAGCTCAGAATTCCACTGTCAAGAAAGAGCAGTAGAGGGGTGT | |
| | GGCTGGGCCTGTCACCCTGGGGCCCTCCAGGTAGGCCCGTTTTCACGT | |
| | GGAGCATGGGAGCCACGACCCTTCTTAAGACATGTATCACTGTAGAGG | |
| | GAAGGAACAGAGGCCCTGGGCCCTTCCTATCAGAAGGACATGGTGAAG | |
| | GCTGGGAACGTGAGGAGAGGCAATGGCCACGCCCATTTTGGCTGTAG | |
| | CACATGGCACGTTGGCTGTGTGGCTTGGCCCACCTGTGAGTTTAAAG | |
| | CAAGGCTTTAAATGACTTTGGAGAGGGTCACAAATCCTAAAAGAAGCA | |
| | TTGAAGTGAGGTGTCATGGATTAATTGACCCCTGTCTATGGAATTACA | |
| | TGTAAAACATTATCTTGTCACTGTAGTTTGGTTTTATTTGAAAACCTG | |
| | ACAAAAAAAAGTTCCAGGTGTGGAATATGGGGTTATCTGTACATCC | |
| | TGGGGCATTAAAAAAAAAATCAATGGTGGGGAACTATAAAGAAGTAAC | |
| | AAAAGAAGTGACATCTTCAGCAAATAAACTAGGAAATTTTTTTTCTT | |
| | CCAGTTTAGAATCAGCCTTGAAACATTGATGGAATAACTCTGTGGCAT | |
| | TATTGCATTATATACCATTTATCTGTATTAACTTTGGAATGTACTCTG | |
| | TTCAATGTTTAATGCTGTGGTTGATATTTCGAAAGCTGCTTTAAAAAA | |
| | ATACATGCATCTCAGCGTTTTTTTGTTTTAATTGTATTTAGTTATGG | |
| | CCTATACACTATTTGTGAGCAAAGGTGATCGTTTTCTGTTTGAGATTT | |
| | TTATCTCTTGATTCTTCAAAAGCATTCTGAGAAGGTGAGATAAGCCCT | |
| | GAGTCTCAGCTACCTAAGAAAAACCTGGATGTCACTGGCCACTGAGGA | |
| | GCTTTGTTTCAACCAAGTCATGTGCATTTCCACGTCAACAGAATTGTT | |
| | TATTGTGACAGTTATATCTGTTGTCCCTTTGACCTTGTTTCTTGAAGG | |
| | TTTCCTCGTCCCTGGGCAATTCCGCATTTAATTCATGGTATTCAGGAT | |
| | TACATGCATGTTTGGTTAAACCCATGAGATTCATTCAGTTAAAAATCC | |
| | AGATGGCAAATGACCAGCAGATTCAAATCTATGGTGGTTTGACCTTTA | |
| | GAGAGTTGCTTTACGTGGCCTGTTTCAACACAGACCCACCCAGAGCCC | |
| | TCCTGCCCTCCTTCCGCGGGGGCTTTCTCATGGCTGTCCTTCAGGGTC | |
| | TTCCTGAAATGCAGTGGTGCTTACGCTCCACCAAGAAAGCAGGAAACC | |
| | TGTGGTATGAAGCCAGACCTCCCCGGCGGGCCTCAGGGAACAGAATGA | |
| | TCAGACCTTTGAATGATTCTAATTTTTAAGCAAAATATTATTTTATGA | |
| | AAGGTTTACATTGTCAAAGTGATGAATATGGAATATCCAATCCTGTGC | |
| | TGCTATCCTGCCAAAATCATTTTAATGGAGTCAGTTTGCAGTATGCTC | |
| | CACGTGGTAAGATCCTCCAAGCTGCTTTAGAAGTAACAATGAAGAACG | |
| | TGGACGTTTTAATATAAAGCCTGTTTTGTCTTTTGTTGTTGTTCAAA | |
| | CGGGATTCACAGAGTATTTGAAAAATGTATATATATTAAGAGGTCACG | |
| | GGGGCTAATTGCTGGCTGGCTGCCTTTTGCTGTGGGGTTTTGTTACCT | |
| | GGTTTTAATAACAGTAAATGTGCCCAGCCTCTTGGCCCCAGAACTGTA | |
| | CAGTATTGTGGCTGCACTTGCTCTAAGAGTAGTTGATGTTGCATTTTC | |
| | CTTATTGTTAAAAACATGTTAGAAGCAATGAATGTATATAAAAGCCTC | |
| | AACTAGTCATTTTTTCTCCTCTTCTTTTTTTCATTATATCTAATTA | |
| | TTTTGCAGTTGGGCAACAGAGAACCATCCCTATTTTGTATTGAAGAGG | |
| | GATTCACATCTGCATCTTAACTGCTCTTTATGAATGAAAAACAGTCC | |
| | TCTGTATGTACTCCTCTTTACACTGGCCAGGGTCAGAGTTAAATAGAG | |
| | TATATGCACTTTCCAAATTGGGGACAAGGGCTCTAAAAAAAGCCCCAA | |
| | AAGGAGAAGAACATCTGAGAACCTCCTCGGCCCTCCCAGTCCCTCGCT | |
| | GCACAAATACTCCGCAAGAGAGGCCAGAATGACAGCTGACAGGGTCTA | |
| | TGGCCATCGGGTCGTCTCCGAAGATTTGGCAGGGGCAGAAAACTCTGG | |
| | CAGGCTTAAGATTTGGAATAAAGTCACAGAATTAAGGAAGCACCTCAA | |
| | TTTAGTTCAAACAAGACGCCAACATTCTCTCCACAGCTCACTTACCTC | |

TABLE 2-continued

BCL2 cDNA and protein sequences.

| Name | Sequence | SEQ ID NO: |
|---|---|---|
| | TCTGTGTTCAGATGTGGCCTTCCATTTATATGTGATCTTTGTTTTATT<br>AGTAAATGCTTATCATCTAAAGATGTAGCTCTGGCCCAGTGGGAAAAA<br>TTAGGAAGTGATTATAAATCGAGAGGAGTTATAATAATCAAGATTAAA<br>TGTAAATAATCAGGGCAATCCCAACACATGTCTAGCTTTCACCTCCAG<br>GATCTATTGAGTGAACAGAATTGCAAATAGTCTCTATTTGTAATTGAA<br>CTTATCCTAAAACAAATAGTTTATAAATGTGAACTTAAACTCTAATTA<br>ATTCCAACTGTACTTTTAAGGCAGTGGCTGTTTTTAGACTTTCTTATC<br>ACTTATAGTTAGTAATGTACACCTACTCTATCAGAGAAAAACAGGAAA<br>GGCTCGAAATACAAGCCATTCTAAGGAAATTAGGGAGTCAGTTGAAAT<br>TCTATTCTGATCTTATTCTGTGGTGTCTTTTGCAGCCCAGACAAATGT<br>GGTTACACACTTTTTAAGAAATACAATTCTACATTGTCAAGCTTATGA<br>AGGTTCCAATCAGATCTTTATTGTTATTCAATTTGGATCTTTCAGGGA<br>TTTTTTTTTTAAATTATTATGGGACAAAGGACATTTGTTGGAGGGGTG<br>GGAGGGAGGAAGAATTTTTAAATGTAAAACATTCCCAAGTTTGGATCA<br>GGGAGTTGGAAGTTTTCAGAATAACCAGAACTAAGGGTATGAAGGACC<br>TGTATTGGGGTCGATGTGATGCCTCTGCGAAGAACCTTGTGTGACAAA<br>TGAGAAACATTTTGAAGTTTGTGGTACGACCTTTAGATTCCAGAGACA<br>TCAGCATGGCTCAAAGTGCAGCTCCGTTTGGCAGTGCAATGGTATAAA<br>TTTCAAGCTGGATATGTCTAATGGGTATTTAAACAATAAATGTGCAGT<br>TTTAACTAACAGGATATTTAATGACAACCTTCTGGTTGGTAGGGACAT<br>CTGTTTCTAAATGTTTATTATGTACAATACAGAAAAAAATTTTATAAA<br>ATTAAGCAATGTGAAACTGAATTGGAGAGTGATAATACAAGTCCTTTA<br>GTCTTACCCAGTGAATCATTCTGTTCCATGTCTTTGGACAACCATGAC<br>CTTGGACAATCATGAAATATGCATCTCACTGGATGCAAAGAAAATCAG<br>ATGGAGCATGAATGGTACTGTACCGGTTCATCTGGACTGCCCCAGAAA<br>AATAACTTCAAGCAAACATCCTATCAACAACAAGGTTGTTCTGCATAC<br>CAAGCTGAGCACAGAAGATGGGAACACTGGTGGAGGATGGAAAGGCTC<br>GCTCAATCAAGAAAATTCTGAGACTATTAATAAATAAGACTGTAGTGT<br>AGATACTGAGTAAATCCATGCACCTAAACCTTTTGGAAAATCTGCCGT<br>GGGCCCTCCAGATAGCTCATTTCATTAAGTTTTTCCCTCCAAGGTAGA<br>ATTTGCAAGAGTGACAGTGGATTGCATTTCTTTTGGGGAAGCTTTCTT<br>TTGGTGGTTTTGTTTATTATACCTTCTTAAGTTTTCAACCAAGGTTTG<br>CTTTTGTTTTGAGTTACTGGGGTTATTTTTGTTTTAAATAAAAATAAG<br>TGTACAATAAGTGTTTTTGTATTGAAAGCTTTTGTTATCAAGATTTTC<br>ATACTTTTACCTTCCATGGCTCTTTTTAAGATTGATACTTTTAAGAGG<br>TGGCTGATATTCTGCAACACTGTACACATAAAAAATACGGTAAGGATA<br>CTTTACATGGTTAAGGTAAAGTAAGTCTCCAGTTGGCCACCATTAGCT<br>ATAATGGCACTTTGTTTGTGTTGTTGGAAAAAGTCACATTGCCATTAA<br>ACTTTCCTTGTCTGTCTAGTTAATATTGTGAAGAAAAATAAAGTACAG<br>TTGTGAGATACG | |
| Bcl2 Protein (Genbank Acc. No. NM_0006 24) | MAHAGRTGYDNREIVMKYIHYKLSQRGYEWDAGDVGAAPPGAAPAPGI<br>FSSQPGHTPHPAASRDPVARTSPLQTPAAPGAAAGPALSPVPPVVHLT<br>LRQAGDDFSRRYRRDFAEMSSQLHLTPFTARGRFATVVEELFRDGVNW<br>GRIVAFFEFGGVMCVESVNREMSPLVDNIALWMTEYLNRHLHTWIQDN<br>GGWDAFVELYGPSMRPLFDFSWLSLKTLLSLALVGACITLGAYLGHK | 56 |

Methods for detecting the expression level of a BCL2 gene product are well known in the art. For example, the expression level of a BCL2 gene transcript in a sample of cells can be detected using techniques already described herein (e.g., Northern blotting, in situ hybridization, RT-PCR). Detection of the expression level of a Bcl2 protein can be accomplished using commonly-applied techniques, for example, immunostaining or Western blotting, which is described in Current Protocols in Molecular Biology, F. Ausubel et al., eds., Vol. 2, John Wiley and Sons, Inc., 1998, Chapter 10.

Bcl2 over-expressing cancers are known to those of skill in the art and include, but are not limited to, leukemias, lymphomas and carcinomas (see Kim, R., et al., Cancer 101(11): 2491-2502 (2004); U.S. Pat. No. 5,789,389; and U.S. Pat. No. 6,800,639, the contents of which are incorporated herein by reference). Particular cancers known to be associated with overexpression of Bcl2 include CLL, acute myeloid leukemia, multiple myeloma, melanoma, follicular lymphoma, large cell lymphoma, non-Hodgkin's lymphoma, non-small cell lung carcinoma, hematologic malignancies, solid tumors, colorectal cancer, brain carcinoma, breast carcinoma, prostate carcinoma, Epstein-Barr virus-associated lymphoproliferative disease, renal carcinoma, hepatocellular carcinoma and gastric carcinoma, among others.

In a particular embodiment, the at least one miR gene product that is administered to the subject in need of treatment comprises a nucleotide sequence that is complementary to a nucleotide sequence in a BCL2 gene transcript.

As used herein, the term "complementary nucleotide sequence" means a polynucleotide sequence that is capable of forming base pairs via hydrogen bonds with another nucleotide sequence to which it is complementary. Such hydrogen bonds are formed between a purine and pyrimidine (e.g., between adenine and thymine or uracil, between guanine and cytosine) through standard Watson-Crick base pairs. As used herein, "Watson-Crick base pair" refers to a pair of hydrogen-bonded bases on opposite antiparallel strands of a nucleic acid. The rules of base pairing, which were first elaborated by Watson and Crick, are well known to those of skill in the art. For example, these rules require that adenine (A) pairs with thymine (T) or uracil (U), and guanine (G) pairs with cytosine (C), with the complementary strands anti-parallel to one another. As used herein, the term "Watson-Crick base pair" encompasses not only the standard AT, AU or GC base pairs, but also base pairs formed between non-standard or modified bases of nucleotide analogs capable of hydrogen bonding to a standard base or to another complementary non-standard base. One example of such non-standard Watson-Crick base pairing is the base pairing which involves the nucleotide analog inosine, wherein its hypoxanthine base can form two hydrogen bonds with adenine, cytosine or uracil.

In one embodiment, the at least one miR gene product comprises a nucleotide sequence that is 100% complementary (i.e., exactly complementary) to a nucleotide sequence in a BCL2 gene transcript. In other embodiments, the at least one miR gene product comprises a nucleotide sequence that is at least about 70%, at least about 80%, at least about 90%, at least about 95%, or at least about 99%, complementary to a nucleotide sequence in a BCL2 gene transcript. The region of complementarity can be from about 5 to about 25 nucleotides in length, from about 5 to about 15 nucleotides in length, or more particularly, from about 7 to about 12 nucleotides in length. Examples of miR gene products having complementary to a nucleotide sequence in a BCL2 gene transcript include, but are not limited to, miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, and miR-186 (see, e.g., Table 5). In one embodiment, the miR gene product comprises a nucleotide sequence that is complementary to nucleotides 3741-3749 of SEQ ID NO: 55. Examples of such miR gene products include, but are not limited to, miR-15a, miR-16-1, miR-15b and miR-16-2. In a particular embodiment, the miR gene product is not miR-15a or miR-16-1. Methods for administering a miR gene product to a subject, several of which are described herein, are well known in the art.

Embodiments of the invention also encompass a method for increasing the efficacy of an anti-cancer treatment in a subject having a cancer, comprising administering to the subject at least one miR gene product that comprises a nucleotide sequence that is complementary to a nucleotide sequence in a BCL2 gene transcript, and additionally administering at least one anti-cancer treatment to the subject. According to embodiments of the invention, the anti-cancer treatment can be any anti-cancer treatment known to those of skill in the art. Suitable anti-cancer treatments include, but are not limited to, chemotherapy, radiation therapy and combinations thereof (e.g., chemoradiation). Embodiments of the invention also contemplate methods of increasing the efficacy of non-conventional cancer therapies.

As used herein, chemotherapy refers to the administration of one or more chemical substances or drugs for the treatment of cancer. A suitable chemotherapeutic agent for use in embodiments of methods of the invention can be any chemical substance known to be useful for treating cancer, for example, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial or exotoxic agents.

Examples of particularly suitable agents for use in methods of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol and derivatives thereof, tamoxifen, dacarbazine, rituximab, daunorubicin, 1-β-D-arabinofuranosylcytosine, imatinib, fludarabine, docetaxel and FOLFOX4.

As used herein, radiation therapy refers to the use of high energy radiation for the treatment of cancer. High energy radiation for use in radiation therapy may be provided by X-rays, gamma ray and neutrons, among others. Different methods of radiation therapy are well known in the art and are suitable for use with the methods of the invention. These methods include, but are not limited to, external beam radiation, brachytherapy, intensity-modulated radiotherapy (IMRT), implant radiation, systemic radiation and stereotactic radiotherapy.

The terms "subject", "individual" and "patient" are defined herein to include animals such as mammals, including but not limited to, primates, cows, sheep, goats, horses, dogs, cats, rabbits, guinea pigs, rats, mice or other bovine, ovine, equine, canine, feline, rodent, or murine species. In a particular embodiment, the animal is a human. In one embodiment, the subject is a mammal (e.g., a human) afflicted with one or more BCL2-associated cancers. As described herein, suitable BCL2-associated cancers for treatment by methods of the invention include lymphomas, carcinomas and leukemias, among others. In a particular embodiment, the BCL2-associated cancer is a cancer that is characterized by increased expression (e.g., overexpression, up-regulation) of a BCL2 gene or gene product (e.g., RNA, protein). Examples of particularly suitable BCL2-associated cancers include CLL, acute myeloid leukemia, multiple myeloma, melanoma, follicular lymphoma, large cell lymphoma, non-Hodgkin's lymphoma, non-small cell lung carcinoma, hematologic malignancies, solid tumors, colorectal cancer, brain carcinoma, breast carcinoma, prostate carcinoma, Epstein-Barr virus-associated lymphoproliferative disease, renal carcinoma, hepatocellular carcinoma and gastric carcinoma, among others. In one embodiment, the cancer is CLL. In another embodiment the cancer is lymphoma. In yet another embodiment, the cancer is lung cancer. In still another embodiment, the cancer is prostate cancer.

According to the methods of one embodiment of the invention, the efficacy of a cancer treatment is increased by administering at least one miR gene product to a subject. The miR gene product may be co-administered (i.e., simultaneously) with a chemotherapeutic agent, or it may be administered separately. In one embodiment, the miR gene product is complementary to a nucleotide sequence in a BCL2 gene transcript. Examples of such miR gene products include, but are not limited to, miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, and miR-186 (see Table 5). In a further embodiment, the miR gene product comprises a nucleotide sequence that is complementary to nucleotides 3741 to 3749 of SEQ ID NO: 55, for example, miR-15a, miR-16-1, miR-15b and miR-16-2. In one embodiment, the miR gene product is not miR-15a or miR-16-1.

An increase in the efficacy of an anti-cancer treatment can be evidenced by increased remission of the cancer in the subject relative to a suitable control. Cancer remission can be determined according to accepted clinical standards, such as a decrease in the number of cancer cells in the subject and/or a decrease in tumor mass and/or size. The number of BCL2-associated cancer cells in a subject can be determined by direct measurement, or by estimation from the size of primary or metastatic tumor masses.

Embodiments of the invention also provide a method of increasing the sensitivity of a cancer cell to the cytotoxic effects of an anti-cancer agent, comprising providing at least one miR gene product comprising a nucleotide sequence that is complementary to a nucleotide sequence in a BCL2 gene transcript to the cell. By providing the at least one miR gene product to the cell, the sensitivity of the cell to the anti-cancer agent is increased.

In one embodiment, the invention is a method of increasing the sensitivity of a cancer cell to the cytotoxic effects of an anti-cancer agent, comprising providing at least one anti-cancer agent to a cancer cell and additionally providing at least one miR gene product to the cancer cell, wherein the at least one miR gene product comprises a nucleotide sequence that is complementary to a nucleotide sequence in a BCL2 gene transcript. The anti-cancer agent may be any agent known to be useful for treating cancer. Such agents include, but are not limited to chemotherapeutic agents and radiation. Examples of suitable chemotherapeutic agents are described hereinabove.

As used herein, the phrase "cytotoxic effects of an anti-cancer agent" refers to any cell damage and/or death that results from the administration of the agent. An increase in the sensitivity of a cancer cell to the cytotoxic effects of an anti-cancer agent can be evidenced by an increase in the severity of cell damage and/or an increase in the quantity or rate of cell death that results from administration of at least one anti-cancer agent and at least one miR gene product, relative to a control cell in which only an anti-cancer agent is provided. Techniques for assessing cytotoxicity (e.g., cell damage and/or death) are well known in the art and include, but are not limited to, assays that monitor cell proliferation, cell growth and cell death (e.g., apoptosis, necrosis).

Suitable cells for use in this embodiment of the invention include cancer cells. In a particular embodiment, the cancer cell overexpresses a BCL2 gene product (e.g., RNA, protein). In one embodiment, the cancer cell is an in vivo cell (e.g., a BCL2-associated cancer cell in a mammal (e.g., a human)). In other embodiments, the cancer cell is obtained from a patient sample (e.g., biopsy, blood) or it may be obtained from an established cancer cell line or a cell line derived from a cancer cell of a patient sample. In certain embodiments, the cancer cell is from a patient sample that was obtained from a subject who has a cancer associated with overexpression of Bcl2. Examples of such cancers include, among others, CLL, acute myeloid leukemia, multiple myeloma, melanoma, follicular lymphoma, large cell lymphoma, non-Hodgkin's lymphoma, non-small cell lung carcinoma, hematologic malignancies, solid tumors, colorectal cancer, brain carcinoma, breast carcinoma, prostate carcinoma, Epstein-Ban virus-associated lymphoproliferative disease, renal carcinoma, hepatocellular carcinoma and gastric carcinoma, among others. In one embodiment, the cancer is CLL. In another embodiment the cancer is lymphoma. In yet another embodiment, the cancer is lung cancer.

According to methods of the invention, the sensitivity of a cancer cell to the cytotoxic effects of a chemotherapeutic agent is increased by providing the cancer cell with at least one miR gene product. In a particular embodiment, the miR gene product is complementary to a nucleotide sequence in a BCL2 gene transcript. Examples of such miR gene products include, but are not limited to, miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, and miR-186 (see Table 5). In a further embodiment, the miR gene product comprises a nucleotide sequence that is complementary to nucleotides 3741 to 3749 of SEQ ID NO: 55, for example, miR-15a, miR-16-1, miR-15b and miR-16-2. In another embodiment, the miR gene product is not miR-15a or miR-16-1.

The miR gene products used in methods of the invention are preferably formulated as pharmaceutical compositions prior to administering to a subject, according to techniques known in the art. Accordingly, the present invention encompasses pharmaceutical compositions comprising at least one miR gene product. In one embodiment, the miR gene product is miR15 or miR16 (e.g., miR-15a or miR-16-1). In other embodiments, the miR gene product comprises a nucleotide sequence that is complementary to a nucleotide sequence in a BCL2 gene transcript. Examples of suitable miR gene products for embodiments of the methods of the present invention include, but are not limited to, miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, and miR-186 (see Table 5). In one embodiment, the miR gene product is not miR-15a or miR-16-1.

In a related embodiment, the compositions of embodiments of the invention further comprise at least one chemotherapeutic agent. Many chemotherapeutic agents that are useful for the treatment of cancer are well known in the art. Suitable chemotherapeutic agents for use in the compositions of the invention are described herein. In certain embodiments, the amount of chemotherapeutic agent administered per dose is from about 0.0001 to 1000 mg/kg, about 0.5 to 70 mg/kg or about 1 to 50 mg/kg.

Pharmaceutical compositions of the present invention are characterized as being sterile and pyrogen-free. As used herein, "pharmaceutical compositions" include compositions for human and veterinary use. Methods for preparing pharmaceutical compositions of the invention are within the skill in the art, for example, as described in *Remington's Pharmaceutical Science,* 17th ed., Mack Publishing Company, Easton, Pa. (1985), the entire disclosure of which is herein incorporated by reference.

In one embodiment, the present pharmaceutical compositions comprise the miR gene product, or a nucleic acid comprising a sequence encoding the gene product (e.g., 0.1 to 90% by weight), or a physiologically acceptable salt thereof, mixed with a pharmaceutically-acceptable carrier. The pharmaceutical compositions of the invention can also comprise the miR gene product, or nucleic acid comprising a sequence encoding the gene product, which are encapsulated by liposomes and a pharmaceutically-acceptable carrier.

Preferred pharmaceutically-acceptable carriers are water, buffered water, normal saline, 0.4% saline, 0.3% glycine, hyaluronic acid and the like.

In a particular embodiment, the pharmaceutical compositions of the invention can comprise a miR gene product that is resistant to degradation by nucleases. One skilled in the art can readily synthesize a miR gene product that is nuclease resistant, for example, by incorporating one or more ribonucleotides that are modified at the 2' position into the miR gene product. Suitable 2'-modified ribonucleotides include those modified at the 2'-position with fluoro, amino, alkyl, alkoxy, and O-allyl.

For example, the pharmaceutical compositions of embodiments of the invention comprise a miR gene product incorporating one or more 2'-modified ribonucleotides of the formulae 2'AR-nucleotide, wherein:

A is oxygen or a halogen (preferably fluorine, chlorine or bromine); and

R is hydrogen or straight or branched chain $C_{1-6}$ alkyl; provided that when A is a halogen, then R is omitted. A preferred modified 2-ribonucleotide is 2'-O methyl ribonucleotide. In one embodiment, pharmaceutical compositions of the invention comprise a miR gene product in which each ribonucleotide is a 2'-modified ribonucleotide.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), chelants (such as, e.g., DTPA or DTPA-bisamide) or calcium chelate complexes (e.g., calcium DTPA, CaNaDTPA-bisamide), or, optionally, additions of calcium or sodium salts (e.g., calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the miR gene product. A pharmaceutical composition for aerosol (inhalational) administration can comprise 0.01-20% by weight, preferably 1%-10% by weight, of the miR gene product encapsulated in a liposome, as described above, and a propellant. A carrier can also be included as desired, e.g., lecithin for intranasal delivery.

The invention also encompasses a method for determining the efficacy of a cancer therapy in a subject, comprising administering at least one test agent to the subject, and subsequently measuring the expression of a miR gene product in a sample from the subject. In one embodiment, the miR gene product is complementary to a nucleotide sequence in a BCL2 gene transcript. Examples of such miR gene products include, but are not limited to, miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, and miR-186 (see Table 5). In a further embodiment, the miR gene product comprises a nucleotide sequence that is complementary to nucleotides 3741 to 3749 of SEQ ID NO: 55, for example, miR-15a, miR-16-1, miR-15b and miR-16-2. In another embodiment, the miR gene product is not miR-15a or miR-16-1.

In a particular embodiment, an increase in the expression of a miR gene product that is complementary to a nucleotide sequence in a BCL2 gene transcript, following administration of the agent, is indicative of a favorable response to treatment. Methods for detecting the expression level of a miR gene product are well known in the art and include, but are not limited to, such techniques as those described hereinabove (e.g., Northern blotting, RT-PCR, in situ hybridization). Suitable agents to be tested include small organic molecules, peptides, and naturally-occurring biological macromolecules, among others. Particularly suitable subjects include individuals suffering from one or more cancers associated with Bcl2 overexpression.

The invention will now be illustrated by the following non-limiting examples.

EXAMPLES

The following techniques were used in the Examples 1-4:
Patient Samples and Cell Lines Patient samples were obtained after informed consent from patients diagnosed with CLL at the CLL Research Consortium institutions. Briefly, peripheral blood was obtained from CLL patients, and mononuclear cells were isolated through Ficoll-Hypaque gradient centrifugation (Amersham Pharmacia Biotech, Piscataway, N.J.) and then processed for RNA and DNA extraction according to standard protocols as described in Sambrook, J., et al. (1989), *Molecular Cloning: A Laboratory Manual* (Cold Spring Harbor Laboratory Press, Cold Spring Harbor, N.Y.), the entire disclosure of which is herein incorporated by reference. As normal controls for LOH studies, DNA from buccal mucosa from the corresponding patients was included on small (1-2 mm$^2$) pieces of paper.

Thirty human cell lines were obtained from the American Type Culture Collection (ATCC; Manassas, Va.) and maintained according to ATCC instructions. These cell lines were AS283, BL2, Bla, BJAB, CA46, Namalva, P3HRI, PAPB 682, PABm, Raji (Burkitt's lymphoma), Dell, SKDHL, ST486 (T-cell lymphoma), JM (immunoblastic B cell lymphoma), MC116 (undifferentiated lymphoma), Molt3, Supt 11 (T-ALL), U266 (multiple myeloma), A549, H1299 (lung carcinoma), TE2, TE10 (esophageal carcinoma), HeLa (cervical carcinoma), RC48 (kidney carcinoma) and 2220, 2221, 11609, 11611, LNCAP, TSUR (prostate carcinoma).

CD5+ B-Cell Separation

Tonsils were obtained from patients in the pediatric age group (3-9 years) undergoing routine tonsillectomies. Purified B cells were obtained by rosetting the mononuclear cells with neuraminidase treated sheep erythrocytes. The B cells were further fractionated by discontinuous Percoll gradients (Pharmacia Biotech, Uppsala, Sweden) as described in Dono, M., et al., *J. Immunol.* 164:5596-5604 (2000), the entire disclosure of which is herein incorporated by reference. The B cells collected from the 50% Percoll fraction were incubated with anti CD5 mAb followed by goat anti mouse Ig conjugated with magnetic microbeads. CD5+ B cells were obtained by positive selection by collecting the cells retained on the magnetic column MS using the Mini-MACS system (Miltenyi Biotec).

Somatic Cell Hybrids

Somatic cell hybrids were generated following conventional methods and selected in hypoxanthine-aminopterin-thymidine (HAT) medium as described in Negrini, M., et al., *Cancer Res.* 54:1818-1824 (1994), the entire disclosure of which is herein incorporated by reference. DNA derived from single cell clones and subclones was isolated with the DNeasy tissue kit (Qiagen) and screened by PCR for the presence or absence of chromosome 13 and chromosome 2 markers (see Table 3 below for primer sequences). Fifteen clones were isolated from fusion of a CLL case (CLL-B)

carrying a t(2;13)(q32; q14) translocation, and one clone was isolated from fusion of another CLL case (CLL-A) carrying a t(2;13)(q12; q13) translocation. Twelve CLL-B derived clones carried a full complement of both chromosomes 13 and 2, whereas three carried the del(13q) and a full complement of chromosome 2. The single clone from CLL-A carried a chromosome 13 with a small deletion at 13q14 and no part of chromosome 2.

Northern Blotting

Total RNA isolation was performed using the Tri-Reagent protocol (Molecular Research Center, Inc). RNA samples (30 μg each) were run on 15% acrylamide denaturing (urea) Criterion precast gels (Bio-Rad Laboratories, Hercules, Calif.) and then transferred onto Hybond-N+ membrane (Amersham Pharmacia Biotech). The hybridization with α-$^{32}$P ATP was performed at 42° C. in 7% SDS, 0.2M Na$_2$PO$_4$ pH 7.0 overnight. Membranes were washed at 42° C., twice in 2×SSPE, 0.1% SDS and twice with 0.5×SSPE, 0.1% SDS. The probes used to detect miR15 and miR16 RNA were, respectively:

```
                                         (SEQ ID NO: 5)
CACAAACCATTATGTGCTTGCTA;
and (SEQ ID NO: 6)
GCCAATATTTACGTGCTGCTA
```

Blots were stripped by boiling in 0.1% aqueous SDS/0.1× SSC for 10 minutes, and were reprobed several times. As a loading control, 5S rRNA stained with ethidium bromide was used.

Reverse Transcriptase Polymerase Chain Reaction (RT-PCR)

RT-PCR was performed to analyze the levels of gene expression in normal CD5+ cells and 23 B-CLL samples. One microliter of cDNA was used for each amplification reaction using the Advantage2 PCR kit (Clontech), with 10 pmol of each gene-specific primer for 35 cycles of 94° C. for 20 seconds, 65° C. for 30 seconds, 68° C. for 1 minute (for a list of primers used, see Table 3 below). To ensure that the RNA was of sufficient purity for RT-PCR, a PCR assay with primers specific for G3PDH cDNA (Clontech, Palo Alto, Calif.) was used. RT-PCR products were separated by agarose gel electrophoresis following standard procedures as described in Sambrook, J., et al. (1989), supra.

Western Blotting

SDS/PAGE gels of cell lysates from 9 B-CLL patients were probed with GST-SLUG Middle antibody (a gift from Dr. Thomas Look—Harvard, Mass.) and SNX2 (N17) antibody (Santa Cruz Biotechnology, CA). Detection was performed using an ECL Western Blotting detection kit (Amersham Pharmacia, UK) according to the manufacturer's instructions.

Database Analysis

Searches against the "nr" and "dbEST" databases, and a search for short, nearly exact matches were performed with the BLAST alignment tool accessed through the National Center for Biotechnology Information website, maintained by the National Institutes of Health and the National Library of Medicine. See also Altschul, et al., *J. Mol. Biol.* 215: 403-10 (1990) and Altschul, et al., *Nucleic Acids Res.* 25:3389-3402 (1997), the entire disclosures of which are herein incorporated by reference. Searches for homology of short sequences were also performed with the FASTA alignment tool provided by the Biology workBench website.

TABLE 3

Primers Used for Screening Somatic Cell Hybrids

| Name | Primer Sequence | SEQ ID NO: |
|---|---|---|
| D2S396L | ATA CAC CTC TAA ATA TCT GTT CCA G | 7 |
| D2S396R | AAG TAG GAC CAT TCT AAT AGC C | 8 |
| D2S112L | GAG TGG CGG TGA GAA GGT AT | 9 |
| D2S112R | AGC CAT TGC TAT CTT TGA GG | 10 |
| D2S2243L | TGG GAT ATG CTT CAG GGA C | 11 |
| D2S2243R | AGC TGA CCT TGG AAT CTG GTT | 12 |
| D13S260L | AGA TAT TGT CTC CGT TCC ATG A | 13 |
| D13S260R | CCC AGA TAT AAG1 GAC CTG GCT A | 14 |
| D13S263L | CCT GGC CTG TTA GTT TTT ATT GTT A | 15 |
| D13S263R | CCC AGT CTT GGG TAT GTT TTT A | 16 |
| D13S165L | GTT TCG CCA AGC CTG TT | 17 |
| D13S165R | GTT GAC AAT AAA ATA CGC CAC A | 18 |
| D13S273L | CTG NGG CAA AAA CAA CTC TT | 19 |
| D13S273R | ATC TGT ATG TCC TCC TTT CAA TG | 20 |
| D13S1168L | AAC CTC ATT TAA ATG TAA AGC ATC A | 21 |
| D13S1168R | GTA ATG TCA TTG CTT TTG ATT TGC | 22 |
| D13S1150L | CTC TTG AGG GAA AAA AAA AAT CA | 23 |

TABLE 3-continued

Primers Used for Screening Somatic Cell Hybrids

| Name | Primer Sequence | SEQ ID NO: |
|---|---|---|
| D13S1150R | CCA GGC AAC CAA CCA GTC | 24 |
| D13S272L | ATA CAG ACT TCC CAG TGG CT | 25 |
| D13S272R | AGC TAT TAA AGT TCC CTG GAT AAA T | 26 |
| GCT16C05L | AAG GAA TCA GAG AAA TGG GG | 27 |
| GCT16C05R | GCT GAG TCA GAG GGA TTT GA | 28 |
| D13S25FOR | AGA GGT AAA CAA ACC AAA CCC | 29 |
| D13S25REV | GCT GAC AAT CAA GAG AAG ATG | 30 |
| D13S284L | AAA ATC AGG TGG AAA CAG AAT | 31 |
| D13S284R | AAA GGC TAA CAT CGA AGG GA | 32 |
| 01ALU18 | CAG AAC CAG AGA AAC AGC | 33 |
| 02ALU18 | ATG GCA CAA CAG CTT AAC | 34 |
| AFMA301WB5 | GAA TGC AGG TGT ACC TAT CAA C | 35 |
| AFMA301WB5 | ACT GAG TGA CTG CTA CCC AG | 36 |
| D13S272L1 | AGC TAG CCC TAT CAG GGT | 37 |
| D13S272R1 | GTA AGT GGA GGT TAC CTG | 38 |
| 5279F | GAA TCA TTC GTG CTA AGT GGA T | 39 |
| 5451R | TGC CAA CTG CTT GAA GAA TCT C | 40 |
| 7130F | ACA CCT AAC TCC TGG GTT GTT C | 41 |
| 7371R | ACT AAA TGC CAG CGT TTG CAT G | 42 |
| 9530F | GGT CTT ACT CTG GTT AAA TCT | 43 |
| 9757R | CAT TGG TAG CTA AGG AAA CAC | 44 |
| 11521F | CCA TTC AAG CCT GGA CAA TCT T | 45 |
| 11802R | GAA ACT TGA GAC AAT AAG GAG C | 46 |
| 12440F | CAT GTA ACC AAG ATA AAT CCG T | 47 |
| 12558R | CTG GAA AAT GTA TGT GAT GAG G | 48 |
| 17261F | CTG TTG CTA TCT GTA ATA ACA C | 49 |
| 17494R | CTT GGA ATT TTC CAC TGA ATC | 50 |
| 18701R | TCA TCA GAA GAA ATC AAG GCA G | 51 |
| 18560F | CAG TGT TAG GAA TAC GCA TTC A | 52 |
| GSP2F4 | CCT TGC CAG TAC GCC CAC AAG CTG | 53 |
| GSP1R1 | CCC CAC CTA TGG TTG TAG TGA GCA TCC | 54 |

Example 1

A 30 kb Deletion Region in Somatic Cell Hybrids of CLL Patients

The minimal region of loss at 13q14 in CLL patients has been unclear. Previously, various and relatively large (between 130 to 550 kb) regions deleted in 13q14 have been described in CLL (see FIG. 2B). LOH and Southern blot analyses were used to identify the centromeric boundary of homozygous loss at the Alu18 locus (FIG. 2D), which is located between D13S1150 and D13S272 less than 65 kb centromeric to exon 5 of the LEU2 gene. However, no small or overlapping homozygous deletions were found that allowed a better localization of the target tumor suppressor.

To better define the region of loss in CLL, somatic cell hybrids of mouse LM-TK⁻ and CLL cells carrying 13q14 translocations and/or deletions were generated. PCR screening of resulting hybrid clones allowed the segregation of the two copies of chromosome 13 present in the tumors. In this manner, a 31.4 kb deletion was identified in one case, and the chromosomal breakpoint was precisely localized in the other (FIG. 2D). These results indicated that the 13q14 tumor suppressor genes lay within a 29 kb region between exons 2 and 5 of the LEU2 gene. The primers used to screen the somatic cell hybrids are given in Table 3.

As shown in FIG. 2, the region deleted in the somatic cell hybrids was consistent with all reported regions of loss, including a 10 kb region reported several years ago by Liu, et al., *Oncogene* 15:2463-2473 (1997). Exons 1 and 2 of LEU2 also lay within that region, and within the one defined here. However, LEU2 has been excluded as a likely candidate tumor suppressor gene for B-CLL (see Bullrich, et al., *Cancer Res.* 61:6640-6648 (2001); Migliazza, et al., *Blood* 97:2098-2104 (2001); Wolf, et al., *Hum. Mol. Genet.* 10:1275-1285 (2001); and Mertens, et al., *Blood* 99:4116-4121 (2002)).

Example 2

Figure 3A:
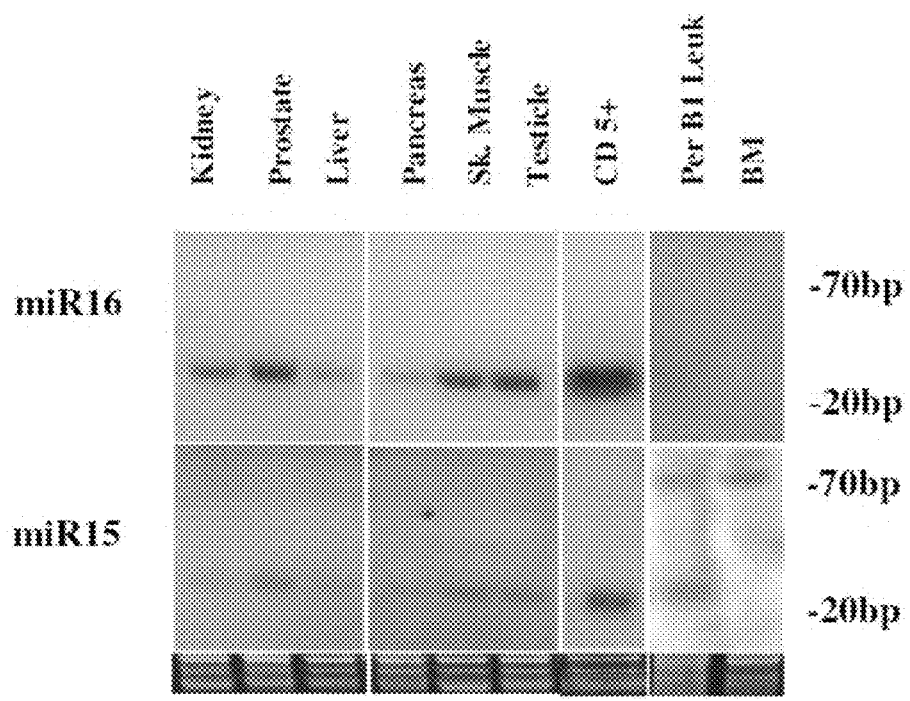
FIG. 3A is a Northern blot analysis of miR15 and miR16 gene expression in normal human kidney, prostate, liver, pancreas, skeletal muscle ("Sk muscle"), testicle, CD5+ B cells (CD5+), leukemia cells ("Per B1 Leuk"), and bone marrow ("BM").

The miR15 and miR16 Genes are Localized in the Minimally Deleted Region of Chromosome 13 and are Highly Expressed in CD5+ Cells Publicly available sequence information and databases were screened for new regulatory genes in the minimal region of loss at 13q14. A cluster of two recently cloned miRNA genes, miR15 and miR16, were located exactly in the deleted region (FIG. 2A). To evaluate the level of expression of miR15 and miR16 in normal tissues, Northern blot analysis of miR15 and miR16 RNA was performed on a panel of normal tissues, including CD5+ B cells isolated from tonsils of normal individuals (FIG. 3A). CD5+ B cells were used as controls, because B-CLL is characterized by a progressive accumulation of CD5+ B-lymphocytes. Ubiquitous expression of both miR15 and miR16 genes was found, with the highest level in normal CD5+ lymphocytes. In addition, miR16 was consistently expressed at higher levels than miR15 in normal tissues. These data indicated that the miR15 and miR16 genes play an important role in normal CD5+ B-cell homeostasis.

Example 3

The miR15 and miR16 Genes are Frequently Deleted or Downregulated in CLL Samples with Deletions at 13q14

To investigate whether the miR15 and miR16 genes were involved in CLL pathogenesis, 60 CLL samples and 30 human cancer cell lines were analyzed for miR15 and miR16 expression by Northern blotting (FIG. 3B). 68% of CLL patients (41/60), as well as 5 out of 6 analyzed prostate cancer cell lines, showed a significant reduction in expression when compared with their normal tissue counterparts. These findings demonstrated that the miR15 and miR16 genes are down-regulated in the majority of B-CLL and prostate cancer cases tested.

In addition, 23 out of 60 CLL samples (38%) presented a clearly identifiable band of about 70 nt representing the miR15 precursor RNA. The 70 nt miR15 band was not found in any normal tissue analyzed except for bone marrow (FIG. 3A), which indicated that miR15 precursor RNA could be inefficiently processed in CLL.

Figure 3B:
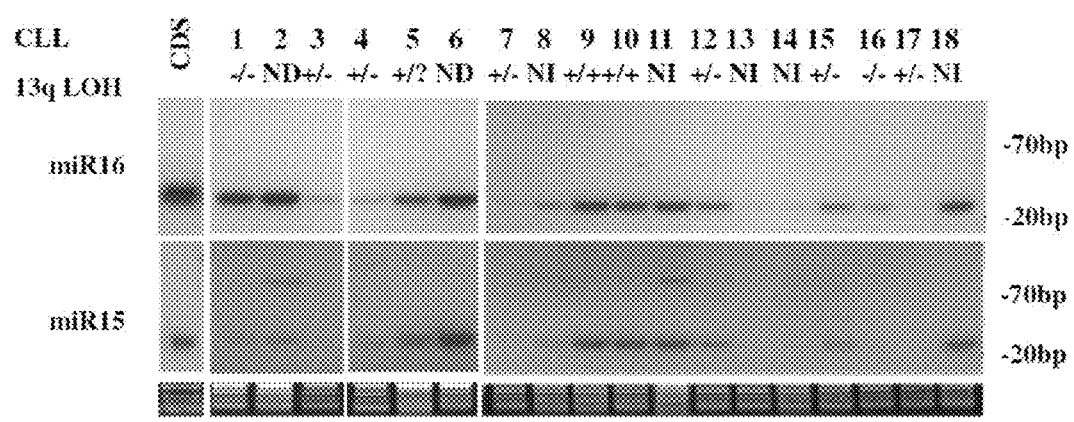
FIG. 3B is a loss of heterozygosity ("LOH") analysis of microsatellite makers D13S272 and D13S273 in 18 CLL patients. DNA from normal human CD5+ cells was used as a control. The LOH status for the samples is shown as "+/+," "+/−," "−/−," "NI" (not informative), "?" (not enough material) and "ND" (not done). Ethidium bromide-stained Northern gels were used as normalization controls.

To determine whether the observed down-regulation of expression correlated with allelic loss in CLL, LOH studies were performed with microsatellite makers D13S272 and D13S273 on 46 CLL patients from whom normal DNA was available (FIG. 3B). We found that 68% of informative samples displayed LOH in at least one marker (24 out of 35 cases). In all but four samples (75%), expression of the miR15/16 gene products was reduced. For 12 samples, reproducible results were not obtained due to the poor quality of the starting material. Additionally, expression levels were reduced in 6 out of 11 cases (55%) without apparent LOH. In these cases, deletions may have been too small to be detected with the markers analyzed.

Northern blot analysis indicated that both miR15 and miR16 gene products were expressed in cases with known large homozygous deletions at 13q14 and with less than 5% normal cells, pointing to the presence of other highly similar micro RNA genes in the genome. Indeed, a cluster very similar to miR15/miR16 gene cluster (but with different precursors) has been reported on chromosome 3q25-26.1 (see Lagos-Quintana, et al., *Curr. Biol.* 12:735-739 (2002)). To show that the variation in miR15/16 gene expression was strictly related to deletions on chromosome 13q, probes specific for miR16 precursor RNA on chromosome 13 and for the miRNA precursor RNA produced from the gene on chromosome 3 were designed and used to probe Northern blots.

While the miR16 precursor RNA from chromosome 13 was detected at low levels, no specific hybridization with the chromosome 3 probe was found in the same samples. In addition, an LOH study was performed with two microsatellite markers spanning a region of 2 Mb located immediately centromeric to this cluster. Four of 17 informative samples showed LOH in at least one marker, and no correlation with the levels of expression of miR15/16 was found. These data clearly demonstrated that down-regulation of miR15 and miR16 gene expression in CLL correlates with allelic loss at 13q14, and provide evidence of a role for miR15 and miR16 gene products in CLL pathogenesis.

Example 4 miR15 and miR16 are Also Involved in CLL Pathogenesis in Mice

To further investigate whether the miR15 and miR16 genes were involved in CLL pathogenesis, studies were extended to Eµ-TCL1 transgenic mice, which develop CLL (Bichi, et al., *Proc. Natl. Acad. Sci. USA* 99(10):6955-6960 (2002)). Cytogenetic and genetic alterations were examined in Eµ-TCL1 transgenic mice. Northern blot analyses were performed as described above (see Examples—"Northern blotting," and Example 3).

In approximately 80% of the transgenic mice, there was a decrease in expression of the mouse homologues of miR15 and miR16 in CLL cells, as compared to normal mouse spleen lymphocytes. These results are similar to those described in Example 3 for miR15 and miR16 expression in human CLL and normal samples.

Comparisons were made between mouse chromosome 15 and human chromosome 12. Comparative gene hybridization (CGH) of the transgenic mouse leukemias showed that approximately 35% had an amplification of a region of mouse chromosome 15, which corresponds to a region of human chromosome 12. Cytogenetic analyses of these mouse leukemias also showed trisomies or tetrasomies of mouse chromosome 15. Trisomies of chromosome 12 are known to occur in approximately 25% of human CLLs.

Comparative gene hybridization also showed a loss of a region of mouse chromosome 14 (51.6-78.5 Mb), which corresponds to region 13q14 in humans.

The results of the studies indicate that the CLL mouse model recapitulates events occurring in the pathogenesis of human CLL.

Taken together, the data presented in Examples 1-4 provide evidence of a role for miR15 and miR16 in CLL pathogenesis in mammals.

The following techniques were used in Examples 5-8:

Patient Samples

Twenty-six CLL samples were obtained, after informed consent, from patients diagnosed with CLL at the CLL Research Consortium institutions. Briefly, blood was obtained from CLL patients, and mononuclear cells were isolated through Ficoll/Hypaque gradient centrifugation (Amersham Pharmacia Biotech) and processed for RNA extraction according to described protocols (Sambrook J., et al. Molecular Cloning: A Laboratory Manual (Cold Spring Harbor Lab, Press, Plainview, N.Y. (1989). Two normal pools containing CD5 positive cells from each of two different normal individuals were used as controls. CD5+ B cells were prepared from tonsillar lymphocytes. Briefly, tonsils were obtained from patients in the pediatric age group (less than 18 years old), who were undergoing routine tonsillectomies, after informed consent. Purified B cell populations were prepared by rosetting T cells from mononuclear cells (MNCs) with neuraminidase-treated sheep erythrocytes (SRBCs). In order to obtain CD5+ B cells, purified B cells were incubated with anti-CD5 monoclonal antibodies (mAb), followed by goat anti mouse Ig conjugated with magnetic microbeads (Miltenyi Biotec, Auburn, Calif.), as described. CD5+ B cells were positively selected by collecting the cells retained on the magnetic column MS by Mini MACS system (Miltenyi Biotec, Auburn, Calif.). The degree of purification of the cell preparations was greater than 95%, as assessed by flow cytometry.

Western Blotting for BCL2

The levels of BCL2 protein were quantified using a mouse monoclonal anti-BCL2 antibody (Dako) and confirmed by using a second mouse monoclonal anti-BCL2 antibody (Santa Cruz Biotechnology, Santa Cruz, Calif.) using standard procedures for Western blotting (Sambrook, J., et al. Molecular Cloning: A Laboratory Manual (Cold Spring Harbor Lab, Press, Plainview, N.Y. (1989)). Normalization was performed with mouse monoclonal anti-Actin antibody (Sigma). The band intensities were quantified using ImageQuantTL (Nonlinear Dynamics Ltd.).

RNA Extraction, Northern Blots, and miRNACHIP Experiments

Procedures were performed as described (Calin, G. A., et al. *Proc. Natl. Acad. Sci. U.S.A.* 99: 15524-15529 (2002); Liu, C. G., et al., *Proc Natl. Acad. Sci. U.S.A.* 101:9740-9744 (2004); Calin, G. A., et al. *Proc. Natl. Acad. Sci. U.S.A.* 101: 11755-11760 (2004)). Briefly, labeled targets from 5 µg of total RNA were used for hybridization on each miRNACHIP microarray chip containing 368 probes in triplicate, corresponding to 245 human and mouse miRNA genes. Raw data were normalized and analyzed in GeneSpring® software version 7.2 (Silicon Genetics, Redwood City, Calif.). Expression data were median centered using both GeneSpring® normalization option or Global Median normalization of the Bioconductor package without any substantial difference. Statistical comparisons were performed using both GeneSpring® ANOVA tool and SAM software (Significance Analysis of Microarray). The microarray data were confirmed by Northern blottings for mir-16-1 and mir-15a, as reported in Calin, G. A., et al., *Proc. Natl. Acad. Sci. USA* 101: 11755-11760 (2004).

mir-16-1/mir-15a Expression Vectors

Wild-type (mir-16-1-WT) and mutant (mir-16-1-MUT) mir-16-1/mir-15a expression vectors were constructed by ligating the relevant open reading frame in a sense orientation into the mammalian expression vector, pSR-GFP-Neo (OligoEngine, Seattle, Wash.). Each construct contained an 832 bp genomic sequence that included both mir-16-1 and mir-15a. The mutant construct contained a C to T substitution at +7 base pairs in the 3' region of mir-16-1. After confirmation by sequencing, each construct was transfected into 293 cells using Lipofectamine-2000, according to the manufacturer's instructions (Invitrogen, Carlsbad, Calif.). The expression of both constructs was assessed by Northern blot analysis, as described in Example 5. Western blot analysis of GFP levels was used to show that both wild-type and mutant pRS-neo-GFP constructs were transfected with equal efficiency.

Transfection Assays

Human megakaryocytic cells (MEG-01) were grown in 10% FBS in RPMI-1640 medium, supplemented with 1× non-essential amino acid and 1 mmol sodium pyruvate, at 37° C. in a humidified atmosphere containing 5% $CO_2$. The cells were cotransfected in 12-well plates using siPORT neoFX (Ambion), according to the manufacturer's instructions, using 0.4 µg of the firefly luciferase reporter vector (Promega) and 0.08 µg of control vector containing *Renilla* luciferase, pRLTK (Promega). For each well, 10 nM of mir-16-1-sense (5'-uagcagcacguaaauauuggcg-3'; SEQ ID NO:341) and/or mir-15a-sense (5'-uagcagcacauaaugguuu-gug-3'; SEQ ID NO:342) (Dharmacon), or miR-15a-antisense and/or miR-16-1 anti-sense precursor miRNA inhibitor (Ambion) were used. Firefly and *Renilla* luciferase activities were measured, consecutively, using a Dual-luciferase assay (Promega), 24 hr after transfection.

Luciferase Reporter Experiments

To generate luciferase reporter constructs, a 546 base pair segment of the 3' UTR of the BCL2 gene was amplified from human genomic DNA by PCR and inserted into the pGL3 control vector (Promega), using the XbaI site immediately downstream from the stop codon of luciferase. The following primer set was used to generate specific fragments:

```
BCL2-UTRF2
                                        (SEQ ID NO: 343)
5'-CTAGTCTAGAGCCTCAGGGAACAGAATGATCAG-3';
and

BCL2-UTRR2
(5'-CTAGTCTAGAAAGCGTCCACGTTCTTCATTG-3';
SEQ ID NO: 344).
```

Two BCL2 inserts with deletions of 5 bp and 9 bp from the site of complementarity with miR-15a and miR-16-1, respectively (see FIG. 4A), were also generated using the QuikChange XL Site-Directed Mutagenesis Kit (Stratagene). Wild-type and mutant inserts were confirmed by sequencing.

Figures 4A, 4B:
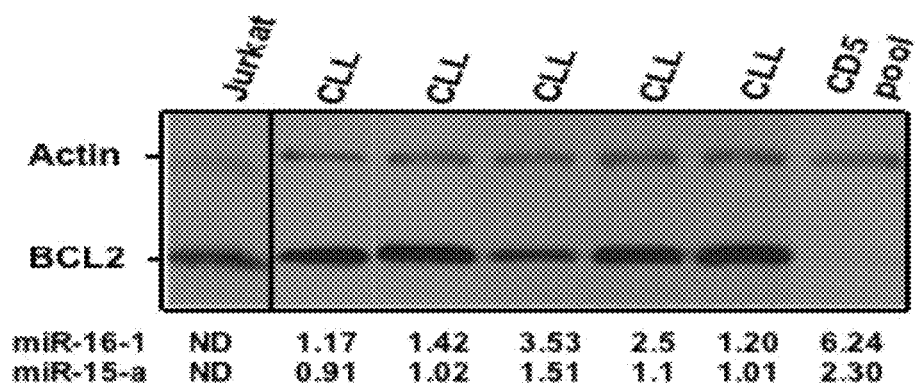
FIG. 4A depicts the regions of miR::mRNA complementarity (red nucleotides) between human miRNAs, miR-15a (Hsa_miR-15; SEQ ID NO:58) or miR-16-1 (Hsa_miR-16; SEQ ID NO:59), and human BCL2 cDNA (Hsa_BCL2; SEQ ID NO:57), as well as mouse miRNAs, miR-15a (Mmu_miR-15; SEQ ID NO:61) or miR-16-1 (Mmu_miR-16; SEQ ID NO:62), and mouse BCL2 cDNA (Mmu_BCL2; SEQ ID NO:60). The sites of targeted deletions in miR-15a and miR-16-1 are indicated for two different 3'UTR mutant constructs: 3'M1, which lacks all 9 bp responsible for the miRNA::mRNA interaction, and 3'M2, which lacks the first 5 bp in the region of complementarity.
FIG. 4B is a Western blot depicting levels of Bcl2 protein in each of 5 different CLL samples (CLL), as well as a pooled sample of CD5 positive B-lymphocytes from normal patients (CD5 pool). Jurkat cells (T-cell leukemia cell line) were used as a control for Bcl2 protein expression. β-actin (Actin) levels were used for normalization. The relative expression of miR-16-1 and miR-15a microRNAs in each sample, as determined by microarray signal intensity, is shown below the corresponding lane under the blot.

Example 5 miR-15a and miR-16-1 Display Complementarity to a Region of the BCL2 Transcript and Show Expression Patterns that are Inversely Correlated with Those of BCL2 Protein Two microRNAs, mir-16-1 and mir-15a, were identified as having homology to the BCL2 mRNA sequence by homology searching. Specifically, the first 9 nucleotides at the 5'-end of both miRNAs were found to be complementary to bases 3741 to 3749 of a human Bcl2 cDNA clone, NM_000633 (FIG. 4A). This region of nucleotides in the BCL2 transcript is conserved in mice (FIG. 4A). miR-15b and miR-16-2, both members of a second cluster from chromosome 3q26, were also identified as having complementarity to the same region of Bcl2 transcripts.

To evaluate whether mir-16-1 and/or mir-15a miRNAs interact with BCL2 transcript, we first determined whether a correlation exists between the expression levels of miR-15a/miR-16-1 and Bcl2 protein levels in both CLL cells and normal CD5 positive lymphocytes. In normal CD5 positive B lymphocytes, the cluster from chromosome 13q14 is highly expressed, while the miR-15b and miR-16-2 precursors are barely detectable by Northern blot analysis (Calin, G. A., et al., *Proc. Natl. Acad. Sci. USA* 99: 15524-15529 (2002)). By miRNACHIP analysis and Western blotting, a set of 30 samples was analyzed, comprising 26 CLL samples and 4 normal CD5 positive lymphocytes from tonsils of unaffected individuals. In normal CD5 positive lymphoid cells, the levels of both miR-15a and miR-16-1 miRNAs were high. In contrast, Bcl2 protein was expressed at low levels. However, in the majority of leukemic cells, both miR-15a and miR-16-1 were expressed at low levels, while Bcl2 protein was overexpressed (FIG. 4B and Table 4). Moreover, in all leukemia samples that were analyzed, we found an inverse correlation between the expression levels of miR-15a/miR-16-1 and those of Bcl2 (Table 4). Thus, in CLL samples, a downregulation of miR-15a and miR-16-1 expression and an overexpression of Bcl2 protein was generally observed.

TABLE 4

Normalized values of BCL2 protein expression by Western blot and miR-15a and miR-16-1 expression by miRNACHIP in a set of 26 CLL samples and two pools of normal CD5 cells*.

| Sa name | Bcl2/ACT | mir-16-1 chip | mir-15a chip | mir16/Bcl2/ACT | mir15/Bcl2/ACT |
|---|---|---|---|---|---|
| N1 + N2 | 0.06 | 9 | 3.5 | 142.08 | 55.25 |
| N1 + N2 | 0.05 | 9 | 3.5 | 169.27 | 65.83 |
| N3 + N4 | 0.07 | 6.24 | 2.3 | 83.58 | 30.81 |
| CLL1 | 0.61 | 4.28 | 1.11 | 7.04 | 1.82 |
| CLL2 | 1.02 | 2.65 | 1.17 | 2.61 | 1.15 |
| CLL3 | 0.17 | 3.08 | 1.12 | 18.40 | 6.69 |
| CLL4 | 0.67 | 2.65 | 1.17 | 3.96 | 1.75 |
| CLL5 | 0.67 | 3.27 | 1.3 | 4.88 | 1.94 |
| CLL6 | 2.95 | 1.42 | 1.02 | 0.48 | 0.35 |
| CLL7 | 1.92 | 3.53 | 1.51 | 1.84 | 0.79 |
| CLL8 | 1.27 | 4.34 | 1.24 | 3.43 | 0.98 |
| CLL8 | 1.50 | 4.3 | 1.26 | 2.86 | 0.84 |
| CLL9 | 2.26 | 2.5 | 1.1 | 1.11 | 0.49 |
| CLL10 | 3.53 | 1.17 | 0.91 | 0.33 | 0.26 |
| CLL11 | 2.50 | 1.2 | 1.01 | 0.48 | 0.40 |
| CLL12 | 10.26 | 1.57 | 1.16 | 0.15 | 0.11 |
| CLL13 | 7.85 | 1.8 | 1.17 | 0.23 | 0.15 |
| CLL14 | 2.86 | 3.28 | 0.99 | 1.15 | 0.35 |
| CLL15 | 1.28 | 9.1 | 2.62 | 7.09 | 2.04 |
| CLL16 | 14.60 | 2.2 | 1.15 | 0.15 | 0.08 |
| CLL17 | 0.99 | 1.54 | 1.08 | 1.55 | 1.09 |
| CLL18 | 7.00 | 1.46 | 1.07 | 0.21 | 0.15 |
| CLL19 | 1.97 | 2.71 | 1.22 | 1.37 | 0.62 |
| CLL20 | 0.56 | 3.08 | 1.12 | 5.50 | 2.00 |
| CLL21 | 0.65 | 2.43 | 1.26 | 3.71 | 1.93 |
| CLL22 | 0.79 | 3.08 | 1.13 | 3.92 | 1.44 |
| CLL23 | 1.30 | 2.2 | 1.15 | 1.69 | 0.88 |
| CLL24 | 1.88 | 0.92 | 0.87 | 0.49 | 0.46 |
| CLL25 | 8.48 | 5.03 | 1.66 | 0.59 | 0.20 |
| CLL26 | 0.17 | 7.64 | 1.69 | 43.70 | 9.67 |

*N1, N2, N3 and N4 = normal CD5 samples; CLL1-CLL26 = chronic lymphocytic leukemia samples. Data are presented as arbitrary units. Two samples, e.g., one normal pool and sample CLL 8, were tested in duplicate to assess data reproducibility. The Western blot (WB) band intensities were quantified using ImageQuantTL (Nonlinear Dynamics Ltd.). Expression data were median-centered using both the GeneSpring normalization option and Global Median normalization of the Bioconductor package without any substantial difference.

Example 6

Figure 5A:
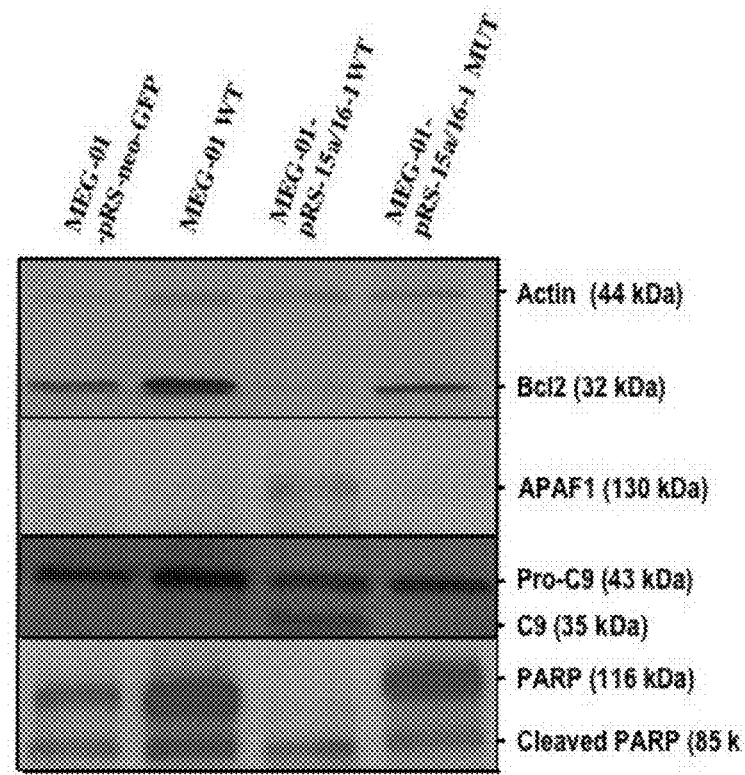
FIG. 5A are Western blots depicting levels of Bcl2 protein, as well as full-length and cleaved forms of various apoptosis activators (e.g., APAF1, Pro-C9, C9, PARP and cleaved PARP), in untransfected MEG-01 cells (MEG-01 WT), as well as MEG-01 cells transfected with empty vector (MEG-01-pRS-neo-GFP), MEG-01 cells transfected with a vector containing the mir-15a/miR-16-1 cluster (MEG-01-pRS-15a/16-1 WT), or MEG-01 cells transfected with a vector containing the mir-15a/miR-16-1 cluster having a +7 (C to T) substitution in the 3' region of the miR-16a precursor (MEG-01-pRS-15a/16-1 MUT). Data were confirmed in duplicate experiments. The pRS-15a/16-1 WT transfected cells showed cleavage of APAF1 (apoptotic protease-activating factor 1, a cytochrome c interactor), pro-caspase 9 (intrinsic apoptosis pathway) and poly (ADP-ribose) polymerase (PARP, a final effector of various apoptotic pathways). Actin was monitored as a loading control.

Expression of microRNAs, miR-15a and miR-16-1, Reduces Expression of BCL2 Protein in Transfected MEG-01 Cells To investigate the effects of expressing the full cluster containing miR-15a/miR-16-1 on Bcl2 expression, MEG-01 cells, an acute leukemia-derived cell line that expresses high levels of Bcl2 but does not express either miR-15a or miR-16-1 due to a deletion of one allele and alteration of the other allele of the miR-15a/16-1 locus, were used. MEG-01 cells that were transiently transfected with the pSR-miR-15/16-WT vector displayed highly reduced levels of Bcl2 (about 7% of normalized expression), relative to wild-type MEG-01 cells (MEG-01 WT) and MEG-01 cells that were transfected with the empty vector (MEG-01-pRS-neo-GFP) (FIG. 5A). To confirm this effect, the same expression vector containing a +7(C to T) germline substitution in miR-16-1 (pSR-miR-15/16-MUT), which was detected in a case of familial CLL (Calin, G. C., et al., *N. Engl. J. Med.*, in press) and strongly reduces the expression of both miRNAs, was transfected. As expected, Bcl2 levels were comparable (75% normalized expression) with those in WT cells or control cells that were transfected with empty vector (FIG. 5A). Furthermore, the cells transfected with pSR-miR-15a/16-1WT showed activation of an intrinsic apoptosis pathway (as determined by activation of the APAF1-caspase 9-PARP pathway). None of the control samples, including the sample of cells transfected with the mutant construct (pSR-miR-15/16-MUT), showed changes in the levels of these pro-apoptotic proteins (FIG. 5A).

Figure 5B:
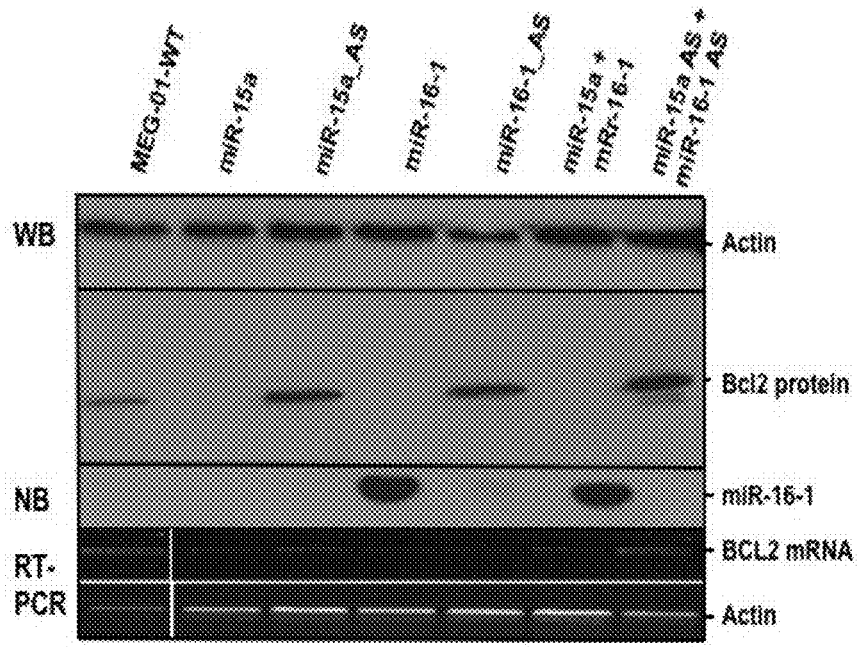
FIG. 5B are Western blots (WB) depicting levels of Bcl2 protein in MEG-01 cells transfected with miR-15a and/or miR-16-1 sense (miR-15a, miR16-1), or miR-15a and/or miR-16-1 antisense (miR-15a_AS, miR16-1_AS) RNA oligonucleotides. Untransfected cells were used as a control (MEG-0'-WT). Normalization was performed using beta-actin (Actin) levels. Northern blots (NB) were performed to assess the transfection efficiency of miR-15-sense and miR-16-sense oligonucleotides. RT-PCR products represent mRNA levels of BCL2 transcripts in the same cells, which are normalized against beta-actin (Actin) mRNA levels (RT-PCR).

To determine if both miR-15a and miR-16-1 miRNAs affect Bcl2 protein expression, we transiently transfected miR-15a and miR-16-1 sense or antisense oligonucleotide RNAs into the MEG-01 cells. As shown in FIG. 5B, separate transfections of miR-15a-sense and miR-16-1-sense oligonucleotides completely abolished Bcl2 expression, while transfection of antisense RNAs for both miRNAs did not affect Bcl2 expression. Similar results were obtained when both sense RNAs or both antisense RNAs were cotransfected (FIG. 5B), confirming that both miR-15a and miR-16-1 miRNAs influence Bcl2 protein expression.

Example 7

Figure 6A:
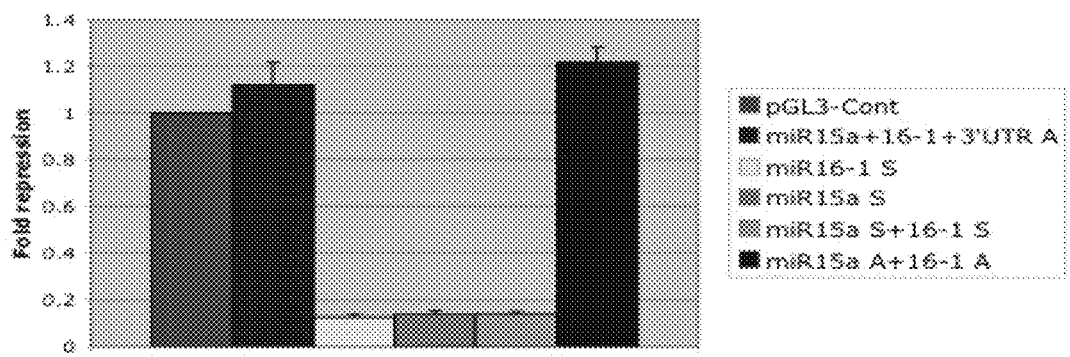
FIG. 6A is a bar graph depicting relative repression (Fold repression) of firefly luciferase expression, standardized to the expression of a *renilla* luciferase transfection control, in cells transfected with either miR-15-a and/or miR-16-1 sense RNA oligonucleotides (miR15a S and miR-16-1 S, respectively), or miR-15-a and/or miR-16-1 antisense RNA oligonucleotides (miR15a A and miR-16-1 A, respectively). Cells were transfected with empty control vector (pGL-3-Cont) or miR-15-a and/or miR-16-1 sense or antisense RNA oligonucleotides. All the experiments were performed twice in triplicate (n=6).
Figure 6B:
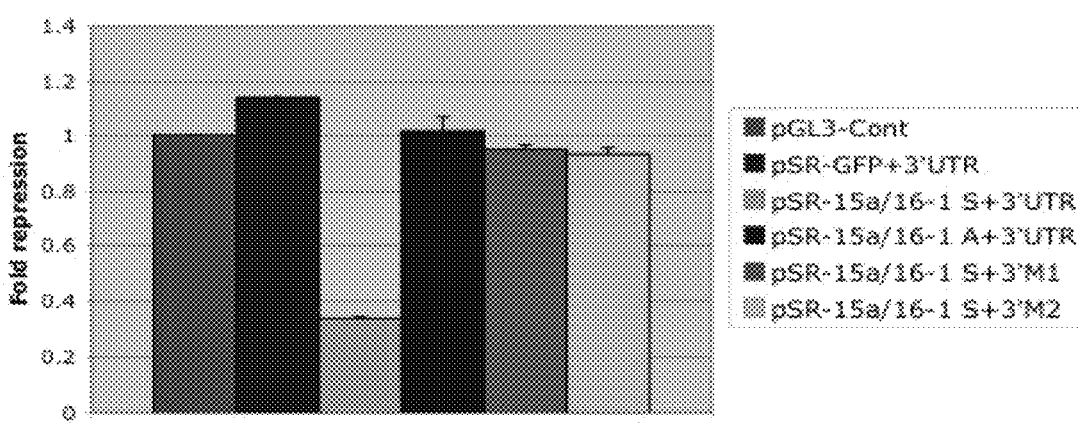
FIG. 6B is a bar graph depicting relative repression of firefly luciferase expression, standardized to a *renilla* luciferase transfection control. Cells were transfected with empty control vector (pGL-3-Cont), miR-15-a and miR-16-1 sense RNA oligonucleotides (pSR-15a/16-1 S+3'UTR) or miR-15-a and miR-16-1 antisense RNA oligonucleotides (pSR-15a/16-1 A +3'UTR) RNA oligonucleotides. 3'UTR represents the luciferase reporter gene fused to a wild-type BCL2 3'UTR sequence. Two different 3'UTR mutants also were transfected, one lacking all 9 bp of the miRNA::mRNA region of complementarity in miR-15-a and miR-16-1 (pSR-15a/16-1 S+3'M1), and the other lacking the first 5 bp in the same complementarity region (pSR-15a/16-1 S+3'M2). All of the experiments were performed twice in triplicate (n=6).

Evidence for a Direct Interaction Between microRNAs, miR-15a and miR-16-1, and the 3' UTR of BCL2 Transcripts Downregulation of Bcl2 protein levels following expression of miR-15a and miR-16-1 could be explained by a direct effect (i.e., hybridization of the miRNAs directly to the Bcl2 transcript via miRNA::mRNA complementarity), or by an indirect interaction (i.e., interaction of miR-15a and miR-16-1 with another target(s), thereby resulting in downregulation of Bcl2 levels). To distinguish between these possibilities, a 536 bp sequence from the 3'UTR of human Bcl2 (nucleotides 3064 to 3599 of SEQ ID NO: 55), which shows complementarity to the miR-15a and miR-16-1 microRNAs, was fused to a luciferase reporter gene. Interaction between either miRNA and the BCL2 mRNA should reduce the firefly luciferase activity (normalized to *Renilla* luciferase activity of the transfection control plasmid), whereas failure of either miRNA to interact with BCL2 mRNA should not affect reporter gene expression. The data presented in FIGS. 6A and 6B are consistent with a direct interaction between miR-15a/miR-16-1 miRNAs and BCL2 transcript, as significant repression of luciferase activity was observed following transfection with either or both microRNAs, relative to control vectors. A control experiment was performed using two types of mutated target mRNA sequences that lacked either 9 (3'M1) or 5 (3'M2) of the bases in miR-15a and miR-16-1 that are complementary to BCL2 cDNA. As expected, both mutants completely abolished the interaction between miR-15a and miR-16-1 and the 3'UTR of BCL2 (FIG. 6B). These data indicate that both miR-15a and miR-16-1 microRNAs directly interact with the 3'UTR of BCL2.

Translocations affecting the Bcl2 gene increase both messenger and protein levels (Tsujimoto, Y., et al., *Science* 228: 1440-1443 (1985)). Because it was recently shown that miRNAs can downregulate a specific target by affecting mRNA translation or mRNA stability (Lim, L. P., et al., *Nature* 433: 769-773 (2005)), the possibility that BCL2 was downregulated by miR15a/16-1 interaction via mRNA stability was tested. Levels of BCL2 mRNA were evaluated by RT-PCR amplification using extracts from cells that were transfected with either pSR-miR-15/16-WT or specific miR-15a and miR-16-1 RNA oligonucleotides. No differences in the level of Bcl2 expression were observed between control cells (e.g., untransfected cells or cells transfected with empty vector) and cells transfected with any of these constructs (FIG. 6A). These results indicate that miR-15a and miR-16-1 do not affect mRNA stability, but are likely to affect translation of Bcl2 mRNA.

Example 8

Identification of Putative microRNA/BCL2 Interactions

In the human genome, four members of the mir15/16 family of miRNAs are present and all have the same 9 bp sequence that is complementary to a region of Bcl2 transcripts. This functional redundancy suggests the existence of a very fine mechanism to regulate Bcl2 expression. Moreover, using a target prediction software (TargetScan (Lewis, R P., et al., *Cell* 120: 15-20 (2005)), BCL2 was identified as a potential target for 14 different miRNAs, including mir15 and mir16 (Table 5). These findings suggest that other microRNAs can regulate Bcl2 protein expression in various cell types.

TABLE 5

Predicted miRNA::BCL2 interactions by different target prediction programs.*

| Rank | microRNA | TargetScanS (p value) | PicTar (score) | Miranda (prediction) |
|---|---|---|---|---|
| 1 | mir-182 | 0.031 | 4.79 | N/A |
| 2 | mir-181 | 0.041 | N/A | N/A |
| 3 | mir-30 | 0.065 | N/A | N/A |
| 4 | mir-15 | 0.091 | 2.08 | N/A |
| 5 | mir-16 | 0.091 | 2.08 | N/A |
| 6 | mir-195 | 0.091 | 2.12 | N/A |
| 7 | mir-34 | 0.15 | 1.34 | Yes |
| 8 | mir-153 | 0.24 | 0.64 | N/A |
| 9 | mir-21 | 0.33 | 0.64 | N/A |
| 10 | mir-217 | 0.36 | 2.37 | N/A |
| 11 | mir-205 | 0.37 | N/A | N/A |
| 12 | mir-204 | 0.4 | 0.73 | Yes |
| 13 | mir-211 | 0.4 | 0.73 | Yes |
| 14 | mir-143 | 0.41 | 3.86 | N/A |
| 15 | mir-96 | N/A | 1.77 | N/A |
| 16 | mir-103 | N/A | 1.23 | N/A |
| 17 | mir-107 | N/A | 1.23 | N/A |
| 18 | mir-129 | N/A | N/A | Yes |
| 19 | mir-9 | N/A | N/A | Yes |
| 20 | mir-137 | N/A | N/A | Yes |
| 21 | mir-217 | N/A | N/A | Yes |
| 22 | mir-186 | N/A | N/A | Yes |

*Note:
TargetScan (MIT) at genes.mit.edu/targetscan/, PicTar (New Your University) at pictar-.bio.nyu.edu/ and Miranda (Memorial Sloan-Kettering Cancer Center) at www.microrna.org/.
N/A—prediction not available.

The data provided herein indicate that Bcl2 overexpression as a consequence of microRNA (e.g., miR-15a, miR-16-1) downregulation is an important mechanism contributing to the pathogenesis of human B-CLL. Notably, downregulation of miR-15a and miR-16-1 also has been reported in cases of diffuse large B cell lymphomas (DLBCL) (E is, P. S., et al., *Proc Natl. Acad. Sci. USA* 102: 3627-3632 (2005)). Therefore, Bcl2 overexpression as a consequence of microRNA (e.g., miR-15a, miR-16-1) downregulation is likely to be involved in other human malignancies.

Example 9

Expression of miR Gene Products in Human Cells

The cDNA sequences encoding one or more entire miR precursor RNAs are separately cloned into the context of an irrelevant mRNA expressed under the control of the cytomegalovirus immediate early (CMV-IE) promoter, according to the procedure of Zeng, et al., *Mol. Cell.* 9:1327-1333 (2002), the entire disclosure of which is herein incorporated by reference.

Briefly, Xho I linkers are placed on the end of double-stranded cDNA sequences encoding the miR precursors, and these constructs are separately cloned into the Xho I site present in the pBC12/CMV plasmid. The pBC12/CMV plasmid is described in Cullen, (1986), *Cell* 46: 973-982, the entire disclosure of which is herein incorporated by reference. The plasmid containing the miR precursor RNA sequences is called pCMV-miR (e.g., pCMV-miR16 for miR-16-1).

One or more pCMV-miR constructs are separately transfected into cultured human 293T cells by standard techniques using the FuGene 6 reagent (Roche). Total RNA is extracted as described above, and the presence of processed microRNA is detected by Northern blot analysis with miR-specific probes.

One or more pCMV-miR constructs are also separately transfected into cultured human cancer cell lines (e.g., carcinoma cell lines 2220, 2221, 11609, 11611, LNCAP, TSUR). Total RNA is extracted as described above, and the presence of processed microRNA in the cancer cells is detected by Northern blot analysis with miR-specific probes. The transfected cancer cells are also evaluated for changes in morphology, the ability to overcome contact inhibition, and other markers indicative of a transformed phenotype.

Example 10

Transfection of BCL2-Associated Cancer Cells with miR Gene Products

BCL2-associated cancer cells from a subject diagnosed with a BCL2-associated cancer are isolated and transfected with plasmids encoding one or more microRNAs as follows.

CD5+ B cells are isolated as described above and BCL2-associated cancer cells (e.g., CLL cells) are identified by visual inspection or, if the cancer is CLL, by determining the CLL Score according to the scoring system of Matutes, et al., *Leukemia* 8(10):1640-1645 (1994), the entire disclosure of which is herein incorporated by reference. CD5+ B cells with a CLL Score of at least 4 are considered CLL cells.

The isolated BCL2-associated cancer cells are transfected with miR expression constructs (e.g., pCMV-miR15, pCMV-miR16) by standard techniques. Total RNA is extracted as described above, and the presence of processed microRNA is detected by Northern blot analysis with probes specific for particular miRs (e.g., miR-15a, miR-16-1). Stable integration of miR gene sequences is also confirmed by Southern blot hybridization using probes specific for certain miR gene sequences.

Example 11

Transfection of Hematopoietic Stem Cells with miR Gene Products

Hematopoietic stem cells (HSC) from subjects diagnosed with a BCL2-associated cancer (e.g., CLL) are obtained from bone marrow as follows.

Bone marrow is harvested from the iliac bones of a subject under general anesthesia in an operating room using standard techniques. Multiple aspirations are taken into heparinized syringes for a total of about 750 to 1000 ml bone marrow. The aspirated marrow is transferred immediately into a transport medium (TC-199, Gibco, Grand Island, N.Y.) containing 10,000 units of preservative-free heparin per 100 ml of medium. The aspirated marrow is filtered through three progressively finer meshes to obtain a cell suspension devoid of cellular aggregates, debris and bone particles. The filtered marrow is then processed further into an automated cell separator (e.g., Cobe 2991 Cell Processor) to obtain the "buffy coat" (i.e., leukocytes devoid of red cells and platelets).

The buffy coat preparation is partially enriched for hematopoietic stem cells (HSC) by positively selecting for CD34+ cells with immunomagnetic beads (Dynal A.S., Oslo, Norway) as follows. The buffy coat preparation is suspended in supplemented alpha medium and incubated with mouse anti-HPCA-I antibody in 1:20 dilution, 45 minutes, at 4° C. with gentle inverting of tubes. The cells are washed 3× in supplemented alpha medium, and then incubated with beads coated with the Fc fragment of goat anti-mouse $IgG_1$ (75 µl of immunobeads/$10^7$ CD34+ cells). After 45 minutes of incubation at 4° C., cells adherent to the beads are positively selected using a magnetic particle concentrator, as directed by the manufacturer.

$2 \times 10^4$ cells from the preparation enriched for HSC are incubated in 5 ml polypropylene tubes (Fisher Scientific, Pittsburgh, Pa.) in a total volume of 0.4 ml of Iscove's modified Dulbecco's medium (IMDM) containing 2% human AB serum and 10 mM Hepes buffer, and are transfected with miR-expressing constructs (e.g., pCMV-miR15, pCMV-miR16) by standard techniques. Expression of microRNA is confirmed in a portion of the transfected HSC by Northern blot analysis, and stable integration of miR gene sequences in a portion of the HSC is confirmed by Southern blot analysis. Approximately $4 \times 10^8$/kg body weight to about $8 \times 10^8$/kg body weight of the remaining transfected cells are reimplanted into the subject according to standard bone marrow transplant techniques.

The experiment is repeated, but the bone marrow is purged of neoplastic cells with ionizing radiation prior to transfection and reimplantation, as follows. Cells in the buffy coat preparation are adjusted to a cell concentration of about $2 \times 10^7$/ml in TC-199 containing about 20% autologous plasma. Recombinant human hematopoietic growth factors rH IL-3 or rH GM-CSF are added to the cell suspension to stimulate growth of hematopoietic neoplasms and thereby increase their sensitivity to ionizing radiation. The cells are then exposed to 5-10 Gy ionizing radiation, washed once at 4° C. in TC-199 containing about 20% autologous plasma, and transfected with miR-expressing constructs (e.g., pCMV-miR15, pCMV-miR16) as above.

Example 12

Preparation of Liposomes Encapsulating microRNAs

Liposome Preparation 1—

Liposomes composed of lactosyl cerebroside, phosphatidylglycerol, phosphatidylcholine and cholesterol in molar ratios of 1:1:4:5 are prepared by the reverse phase evaporation method described in U.S. Pat. No. 4,235,871, the entire disclosure of which is herein incorporated by reference. The liposomes are prepared in an aqueous solution of 100 µg/ml processed microRNA or 500 µg/ml (e.g., pCMV-miR15, pCMV-miR16). The liposomes thus prepared encapsulate either the processed microRNA (e.g., miR-15a, miR-16-1 RNA), or the constructs expressing microRNA (e.g., pCMV-miR15, pCMV-miR16 plasmids).

The liposomes are then passed through a 0.4 polycarbonate membrane and suspended in saline, and are separated from non-encapsulated material by column chromatography in 135 mM sodium chloride, 10 mM sodium phosphate pH 7.4. The liposomes are used without further modification, or are modified as described below.

A quantity of the liposomes prepared above are charged to an appropriate reaction vessel to which is added, with stirring, a solution of 20 mM sodium metaperiodate, 135 mM sodium chloride and 10 mM sodium phosphate (pH 7.4). The resulting mixture is allowed to stand in darkness for 90 minutes at a temperature of about 20° C. Excess periodate is removed by dialysis of the reaction mixture against 250 ml of buffered saline (135 mM sodium chloride, 10 mM sodium phosphate, pH 7.4) for 2 hours. The product is a liposome having a surface modified by oxidation of carbohydrate hydroxyl groups to aldehyde groups. Targeting groups or opsonization inhibiting moieties are conjugated to the liposome surface via these aldehyde groups.

Liposome Preparation 2—

A second liposome preparation composed of maleimidobenzoyl-phosphatidylethanolamine (MBPE), phosphatidylcholine and cholesterol is obtained as follows. MBPE is an activated phospholipid for coupling sulfhydryl-containing compounds, including proteins, to the liposomes.

Dimyristoylphosphatidylethanolamine (DMPE) (100 mmoles) is dissolved in 5 ml of anhydrous methanol containing 2 equivalents of triethylamine and 50 mg of m-maleimidobenzoyl N-hydroxysuccinimide ester, as described in Kitagawa, et al., *J. Biochem.* 79:233-236 (1976), the entire disclosure of which is herein incorporated by reference. The resulting reaction is allowed to proceed under a nitrogen gas atmosphere overnight at room temperature, and is subjected to thin layer chromatography on Silica gel H in chloroform/methanol/water (65/25/4), which reveals quantitative conversion of the DMPE to a faster migrating product. Methanol is removed under reduced pressure and the products re-dissolved in chloroform. The chloroform phase is extracted twice with 1% sodium chloride and the maleimidobenzoyl-phosphatidylethanolamine (MBPE) purified by silicic acid chromatography with chloroform/methanol (4/1) as the solvent. Following purification, thin-layer chromatography indicates a single phosphate containing spot that is ninhydrin negative.

Liposomes are prepared with MBPE, phosphatidylcholine and cholesterol in molar ratios of 1:9:8 by the reverse phase evaporation method of U.S. Pat. No. 4,235,871, supra, in an aqueous solution of 100 µg/ml processed microRNA or a solution of microRNA-encoding plasmid. Liposomes are separated from non-encapsulated material by column chromatography in 100 mM sodium chloride-2 mM sodium phosphate (pH 6.0).

Example 13

Attachment of Anti-CD5+ or Anti-Prostate Tumor Antibodies to Liposomes Encapsulating miR Gene Products An appropriate vessel is charged with 1.1 ml (containing about 10 mmoles) of Liposome Preparation 1 carrying reactive aldehyde groups, or Liposome Preparation 2 above. 0.2 ml of a 200 mM sodium cyanoborohydride solution and 1.0 ml of a 3 mg/ml solution of a monoclonal antibody directed against the CD5+ cell surface marker or a prostate tumor cell antigen is added to the preparation, with stirring. The resulting reaction mixture is allowed to stand overnight while maintained at a temperature of 4° C. The reaction mixture is separated on a Biogel A5M agarose column (Biorad, Richmond, Calif.; 1.5×37 cm).

Example 14

Inhibition of Human Prostate Tumor Growth In Vivo with miR Gene Products

A hormone refractory human prostate adenocarcinoma cell line (PC-3) is inoculated into nude mice, and the mice are divided into treatment and control groups. When tumors in the mice reach 100 to 250 cubic millimeters, one or more processed microRNAs (e.g., miR-15a, miR-16-1) encapsulated in liposomes are injected directly into the tumors of the control group. The tumors of the control group are injected with liposomes encapsulating carrier solution only. Tumor volume is measured throughout the study. The efficacy of miR gene products in inhibiting prostate tumor growth in the Dunning R-3327 rat prostate adenocarcinoma model is also evaluated, as follows. A highly metastatic and malignant clone (RT-3.1) of Dunning R-3327 prostate adenocarcinoma cells is inoculated into Copenhagen rats, which are then divided into treatment and control groups. Both groups form solid tumor masses in approximately one week. The tumors of rats in the treatment group are then injected with processed microRNA encapsulated in liposomes twice a week for 5 weeks. The tumors of the control group are injected with liposomes encapsulating carrier solution only. Tumor volume is measured throughout the study.

The relevant teachings of all references not previously incorporated by reference are herein incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof.

What is claimed is:

1. A pharmaceutical composition for treating a Bcl2-associated cancer, comprising at least one anti-cancer agent and at least one miR-15a or miR-16-1 gene product, wherein the at least one miR-15a or miR-16-1 gene product consists of a nucleotide sequence that is complementary to nucleotides 3741-3749 of SEQ ID NO: 55, and is present in an amount to increase the efficacy of the anti-cancer agent.

2. The pharmaceutical composition of claim 1, wherein the anti-cancer agent is a chemotherapeutic agent.

3. The pharmaceutical composition of claim 1, wherein the cancer is chronic lymphocytic leukemia (CLL).

4. The pharmaceutical composition of claim 1, wherein the cancer is prostate cancer.

5. The pharmaceutical composition of claim 1, wherein the cancer is lung cancer.

6. The pharmaceutical composition of claim 1, wherein the cancer is colorectal cancer.

7. The pharmaceutical composition of claim 1, wherein the composition is formulated for administration to a human subject.

8. The pharmaceutical composition of claim 1, wherein the composition is formulated for administration to a human subject by intratumoral injection.

9. The pharmaceutical composition of claim 1, wherein the composition is formulated for administration to a human subject by intravenous infusion.

10. The pharmaceutical composition of claim 1, wherein the at least one miR-15a or miR-16-1 gene product comprises one or more ribonucleotides that are modified at the 2' position.

11. The pharmaceutical composition of claim 10, wherein the 2' modification is selected from the group consisting of fluoro, amino, alkyl, alkoxy, and O-allyl.

12. The pharmaceutical composition of claim 10, wherein the 2' modification comprises the formula 2' AR-nucleotide, wherein:
A is oxygen or a halogen; and
R is hydrogen or a straight or branched chain $C_{1-6}$ alkyl; provided that when A is a halogen, R is omitted.

13. The pharmaceutical composition of claim 12, wherein A is selected from the group consisting of fluorine, chlorine, and bromine.

14. The pharmaceutical composition of claim 10, wherein the at least one miR-15a or miR-16-1 gene product comprises a 2'-O methyl ribonucleotide.

15. The pharmaceutical composition of claim 10, wherein each ribonucleotide in the miR-15a or miR-16-1 gene product is a 2'-modified ribonucleotide.

16. The pharmaceutical composition of claim 1, wherein the anti-cancer agent is radiation therapy.

17. The pharmaceutical composition of claim 2, wherein the amount of the chemotherapeutic agent ranges from about 0.0001 mg/k to about 1000 mg/kg.

18. The pharmaceutical composition of claim 2, wherein the amount of the chemotherapeutic agent ranges from about 0.5 mg/kg to about 70 mg/kg.

19. The pharmaceutical composition of claim 2, wherein the amount of the chemotherapeutic agent ranges from about 1 mg/kg to about 50 mg/kg.

20. The pharmaceutical composition of claim 1, wherein the at least one miR-15a or miR-16-1 gene product is encapsulated in a liposome.

* * * * *

UNITED STATES PATENT AND TRADEMARK OFFICE
CERTIFICATE OF CORRECTION

PATENT NO. : 9,480,699 B2
APPLICATION NO. : 14/341145
DATED : November 1, 2016
INVENTOR(S) : Carlo M. Croce and George A. Calin It is certified that error appears in the above-identified patent and that said Letters Patent is hereby corrected as shown below:

In the Specification

Column 1, Lines 21-24 replace the Government Support Clause with:
--This invention was made with government support under grant numbers CA081534 and CA056036 awarded by the National Institutes of Health. The government has certain rights in the invention.--

Signed and Sealed this
Sixth Day of October, 2020

Andrei Iancu
*Director of the United States Patent and Trademark Office*

SEQUENCE LISTING

```
<160> NUMBER OF SEQ ID NOS: 344

<210> SEQ ID NO 1
<211> LENGTH: 83
<212> TYPE: RNA
<213> ORGANISM: Homo sapiens

<400> SEQUENCE: 1
ccuuggagua aaguagcagc acauaauggu uuguggauuu ugaaaaggug caggccauau        60
ugugcugccu caaaaauaca agg                                               83

<210> SEQ ID NO 2
<211> LENGTH: 89
<212> TYPE: RNA
<213> ORGANISM: Homo sapiens

<400> SEQUENCE: 2
gucagcagug ccuuagcagc acguaaauau uggcguuaag auucuaaaau uaucuccagu        60
auuaacugug cugcugaagu aagguugac                                         89

<210> SEQ ID NO 3
<211> LENGTH: 22
<212> TYPE: RNA
<213> ORGANISM: Homo sapiens
```

<400> SEQUENCE: 3
uagcagcaca uaaugguuug ug						22

<210> SEQ ID NO 4
<211> LENGTH: 22
<212> TYPE: RNA
<213> ORGANISM: Homo sapiens

<400> SEQUENCE: 4
uagcagcacg uaaauauugg cg						22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cacaaaccat tatgtgcttg cta						23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccaatattt acgtgctgct a							21

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atacacctct aaatatctgt tccag						25

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagtaggacc attctaatag cc						22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagtggcggt gagaaggtat						20

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agccattgct atctttgagg                                                    20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgggatatgc ttcagggac                                                     19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agctgacctt ggaatctggt t                                                  21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agatattgtc tccgttccat ga                                                 22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccagatata aggacctggc ta                                                 22

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctggcctgt tagtttttat tgtta                                              25
```

```
<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cccagtcttg ggtatgtttt ta                                              22

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtttcgccaa gcctgtt                                                    17

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttgacaata aaatacgcca ca                                              22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: a, c, g, t, unknown or other

<400> SEQUENCE: 19
ctgnggcaaa aacaactctt                                                 20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atctgtatgt cctcctttca atg                                             23

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
```
aacctcattt aaatgtaaag catca                                           25

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtaatgtcat tgcttttgat ttgc                                            24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctcttgaggg aaaaaaaaaa tca                                             23

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccaggcaacc aaccagtc                                                   18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atacagactt cccagtggct                                                 20

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agctattaaa gttccctgga taaat                                           25

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaggaatcag agaaatgggg                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gctgagtcag agggatttga                                    20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agaggtaaac aaaccaaacc c                                  21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gctgacaatc aagagaagat g                                  21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aaaatcaggt ggaaacagaa t                                  21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaaggctaac atcgaaggga                                    20

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cagaaccaga gaaacagc                                      18

```
<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atggcacaac agcttaac                                                    18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaatgcaggt gtacctatca ac                                               22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
actgagtgac tgctacccag                                                  20

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agctagccct atcagggt                                                    18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtaagtggag gttacctg                                                    18

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaatcattcg tgctaagtgg at                                               22
```

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
tgccaactgc ttgaagaatc tc                                              22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
acacctaact cctgggttgt tc                                              22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
actaaatgcc agcgtttgca tg                                              22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
ggtcttactc tggttaaatc t                                               21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
cattggtagc taaggaaaca c                                               21

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ccattcaagc ctggacaatc tt                                              22

```
<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gaaacttgag acaataagga gc                                              22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
catgtaacca agataaatcc gt                                              22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctggaaaatg tatgtgatga gg                                              22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctgttgctat ctgtaataac ac                                              22

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cttggaattt tccactgaat c                                               21

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcatcagaag aaatcaaggc ag                                              22

<210> SEQ ID NO 52
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cagtgttagg aatacgcatt ca                                              22

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccttgccagt acgcccacaa gctg                                            24

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccccacctat ggttgtagtg agcatcc                                         27

<210> SEQ ID NO 55
<211> LENGTH: 6492
<212> TYPE: DNA
<213> ORGANISM: Homo sapiens

<400> SEQUENCE: 55
tttctgtgaa gcagaagtct gggaatcgat ctggaaatcc tcctaatttt tactccctct      60
ccccgcgact cctgattcat tgggaagttt caaatcagct ataactggag agtgctgaag     120
attgatggga tcgttgcctt atgcatttgt tttggtttta caaaaaggaa acttgacaga     180
ggatcatgct gtacttaaaa aatacaacat cacagaggaa gtagactgat attaacaata     240
cttactaata ataacgtgcc tcatgaaata aagatccgaa aggaattgga ataaaaattt     300
cctgcatctc atgccaaggg ggaaacacca gaatcaagtg ttccgcgtga ttgaagacac     360
cccctcgtcc aagaatgcaa agcacatcca ataaaatagc tggattataa ctcctcttct     420
ttctctgggg gccgtggggt gggagctggg gcgagaggtg ccgttggccc ccgttgcttt     480
tcctctggga aggatggcgc acgctgggag aacagggtac gataaccggg agatagtgat     540
gaagtacatc cattataagc tgtcgcagag gggctacgag tgggatgcgg gagatgtggg     600
cgccgcgccc ccgggggccg cccccgcacc gggcatcttc tcctcccagc ccgggcacac     660
gccccatcca gccgcatccc gggacccggt cgccaggacc tcgccgctgc agaccccggc     720 tgccccggc gccgccgcgg ggcctgcgct cagcccggtg ccacctgtgg tccacctgac     780
cctccgccag gccggcgacg acttctcccg ccgctaccgc cgcgacttcg ccgagatgtc     840
cagccagctg cacctgacgc ccttcaccgc gcggggacgc tttgccacgg tggtggagga     900
gctcttcagg gacggggtga actggggag gattgtggcc ttctttgagt tcggtggggt     960
catgtgtgtg gagagcgtca accgggagat gtcgcccctg tggacaacaa tcgccctgtg    1020
```

```
gatgactgag tacctgaacc ggcacctgca cacctggatc caggataacg gaggctggga    1080
tgcctttgtg gaactgtacg gccccagcat gcggcctctg tttgatttct cctggctgtc    1140
tctgaagact ctgctcagtt tggccctggt gggagcttgc atcaccctgg gtgcctatct    1200
gggccacaag tgaagtcaac atgcctgccc caaacaaata tgcaaaaggt tcactaaagc    1260
agtagaaata atatgcattg tcagtgatgt accatgaaac aaagctgcag gctgtttaag    1320
aaaaaataac acacatataa acatcacaca cacagacaga cacacacaca caacaatt     1380
aacagtcttc aggcaaaacg tcgaatcagc tatttactgc caagggaaa tatcatttat     1440
ttttacatt attaagaaaa aaagatttat ttatttaaga cagtcccatc aaaactcctg     1500
tctttggaaa tccgaccact aattgccaag caccgcttcg tgtggctcca cctggatgtt   1560
ctgtgcctgt aaacatagat tcgctttcca tgttgttggc cggatcacca tctgaagagc    1620
agacggatgg aaaaaggacc tgatcattgg ggaagctggc tttctggctg ctggaggctg    1680
gggagaaggt gttcattcac ttgcatttct ttgccctggg ggctgtgata ttaacagagg    1740
gagggttcct gtgggggaa gtccatgcct ccctggcctg aagaagagac tctttgcata    1800
tgactcacat gatgcatacc tggtgggagg aaaagagttg ggaacttcag atggacctag    1860
tacccactga gatttccacg ccgaaggaca gcgatgggaa aaatgccctt aaatcatagg    1920
aaagtatttt tttaagctac caattgtgcc gagaaaagca ttttagcaat ttatacaata    1980
tcatccagta ccttaagccc tgattgtgta tattcatata ttttggatac gcaccccca     2040
actcccaata ctggctctgt ctgagtaaga aacagaatcc tctggaactt gaggaagtga    2100
acatttcggt gacttccgca tcaggaaggc tagagttacc cagagcatca ggccgccaca    2160
agtgcctgct tttaggagac cgaagtccgc agaacctgcc tgtgtcccag cttggaggcc    2220
tggtcctgga actgagccgg ggccctcact ggcctcctcc agggatgatc aacagggcag    2280
tgtggtctcc gaatgtctgg aagctgatgg agctcagaat tccactgtca agaaagagca    2340
gtagaggggt gtggctgggc ctgtcaccct ggggccctcc aggtaggccc gttttcacgt    2400
ggagcatggg agccacgacc cttcttaaga catgtatcac tgtagaggga aggaacagag    2460
gccctgggcc cttcctatca gaaggacatg gtgaaggctg ggaacgtgag gagaggcaat    2520
ggccacggcc catttttggct gtagcacatg gcacgttggc tgtgtggcct tggcccacct    2580
gtgagtttaa agcaaggctt taaatgactt tggagagggt cacaaatcct aaaagaagca    2640
ttgaagtgag gtgtcatgga ttaattgacc cctgtctatg gaattacatg taaaacatta    2700
tcttgtcact gtagtttggt tttatttgaa aacctgacaa aaaaaagtt ccaggtgtgg     2760
aatatggggg ttatctgtac atcctgggc attaaaaaaa aaatcaatgg tggggaacta    2820
taaagaagta acaaaagaag tgacatcttc agcaaataaa ctaggaaatt ttttttttctt   2880
ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaaatacat gcatctcagc gttttttgt ttttaattgt     3060
atttagttat ggcctataca ctatttgtga gcaaggtga tcgttttctg tttgagattt     3120
ttatctcttg attcttcaaa agcattctga gaaggtgaga taagccctga gtctcagcta    3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
```

```
accagcagat tcaaatctat ggtggtttga cctttagaga gttgctttac gtggcctgtt    3480
tcaacacaga cccacccaga gccctcctgc cctccttccg cggggggcttt ctcatggctg    3540 tccttcaggg tcttcctgaa atgcagtggt gcttacgctc caccaagaaa gcaggaaacc    3600
tgtggtatga agccagacct ccccggcggg cctcagggaa cagaatgatc agacctttga    3660
atgattctaa ttttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt    4140
ttttctcctc ttctttttttt tcattatatc taattatttt gcagttgggc aacagagaac    4200 catcccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata atcgagagg agttataata    4740 atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attagggagt cagttgaaat    5040
tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggattttt ttttaaatta ttatgggaca aaggacattt    5220
gttggagggg tgggagggag gaagaatttt taaatgtaaa acattccaa gtttggatca    5280 gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
caatggtata aatttcaagc tggatatgtc taatgggtat ttaaacaata aatgtgcagt    5520
tttaactaac aggatatttta atgacaacct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
```

```
atggagcatg aatggtactg taccggttca tctggactgc cccagaaaaa taacttcaag   5820
caaacatcct atcaacaaca aggttgttct gcataccaag ctgagcacag aagatgggaa   5880
cactggtgga ggatggaaag gctcgctcaa tcaagaaaat tctgagacta ttaataaata   5940
agactgtagt gtagatactg agtaaatcca tgcacctaaa ccttttggaa aatctgccgt   6000
gggccctcca gatagctcat ttcattaagt ttttccctcc aaggtagaat ttgcaagagt   6060
gacagtggat tgcatttctt ttggggaagc tttcttttgg tggttttgtt tattatacct   6120
tcttaagttt tcaaccaagg tttgcttttg ttttgagtta ctggggttat ttttgtttta   6180
aataaaaata agtgtacaat aagtgttttt gtattgaaag cttttgttat caagattttc   6240
atacttttac cttccatggc tcttttaag attgatactt ttaagaggtg gctgatattc   6300
tgcaacactg tacacataaa aaatacggta aggatacttt acatggttaa ggtaaagtaa   6360
gtctccagtt ggccaccatt agctataatg gcactttgtt tgtgttgttg gaaaaagtca   6420
cattgccatt aaactttcct tgtctgtcta gttaatattg tgaagaaaaa taaagtacag   6480
tgtgagatac tg                                                       6492
```

<210> SEQ ID NO 56
<211> LENGTH: 239
<212> TYPE: PRT
<213> ORGANISM: Homo sapiens

<400> SEQUENCE: 56

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235
```

<210> SEQ ID NO 57
<211> LENGTH: 30
<212> TYPE: DNA
<213> ORGANISM: Homo sapiens

<400> SEQUENCE: 57
tatggaatat ccaatcctgt gctgctatcc                              30

<210> SEQ ID NO 58
<211> LENGTH: 22
<212> TYPE: DNA
<213> ORGANISM: Homo sapiens

<400> SEQUENCE: 58
gtgtttggta atacacgacg at                                      22

<210> SEQ ID NO 59
<211> LENGTH: 22
<212> TYPE: DNA
<213> ORGANISM: Homo sapiens

<400> SEQUENCE: 59
gcggttataa atgcacgacg at                                      22

<210> SEQ ID NO 60
<211> LENGTH: 29
<212> TYPE: DNA
<213> ORGANISM: Homo sapiens

<400> SEQUENCE: 60
tggggaagcc tgcagtctgg ctgctagaa                               29

<210> SEQ ID NO 61
<211> LENGTH: 22
<212> TYPE: DNA
<213> ORGANISM: Homo sapiens

<400> SEQUENCE: 61
gtgtttggta atacacgacg at                                      22

<210> SEQ ID NO 62
<211> LENGTH: 22
<212> TYPE: DNA
<213> ORGANISM: Homo sapiens

<400> SEQUENCE: 62
gcggttataa atgcacgacg at                                      22

<210> SEQ ID NO 63
<211> LENGTH: 90
<212> TYPE: DNA
<213> ORGANISM: Homo sapiens

<400> SEQUENCE: 63
cactgtggga tgaggtagta ggttgtatag ttttagggtc acacccacca ctgggagata    60
actatacaat ctactgtctt tcctaacgtg                                    90

<210> SEQ ID NO 64
<211> LENGTH: 72
<212> TYPE: DNA
<213> ORGANISM: Homo sapiens

<400> SEQUENCE: 64

```
aggttgaggt agtaggttgt atagtttaga attacatcaa gggagataac tgtacagcct    60
cctagctttc ct                                                        72

<210> SEQ ID NO 65
<211> LENGTH: 74
<212> TYPE: DNA
<213> ORGANISM: Homo sapiens

<400> SEQUENCE: 65
gggtgaggta gtaggttgta tagtttgggg ctctgccctg ctatgggata actatacaat    60
ctactgtctt tcct                                                      74

<210> SEQ ID NO 66
<211> LENGTH: 107
<212> TYPE: DNA
<213> ORGANISM: Homo sapiens

<400> SEQUENCE: 66
gtgactgcat gctcccaggt tgaggtagta ggttgtatag tttagaatta cacaagggag    60
ataactgtac agcctcctag ctttccttgg gtcttgcact aaacaac                 107

<210> SEQ ID NO 67
<211> LENGTH: 85
<212> TYPE: DNA
<213> ORGANISM: Homo sapiens

<400> SEQUENCE: 67
ggcggggtga ggtagtaggt tgtgtggttt cagggcagtg atgttgcccc tcggaagata    60
actatacaac ctactgcctt ccctg                                          85

<210> SEQ ID NO 68
<211> LENGTH: 84
<212> TYPE: DNA
<213> ORGANISM: Homo sapiens

<400> SEQUENCE: 68
gcatccgggt tgaggtagta ggttgtatgg tttagagtta caccctggga gttaactgta    60
caaccttcta gctttccttg gagc                                           84

<210> SEQ ID NO 69
<211> LENGTH: 87
<212> TYPE: DNA
<213> ORGANISM: Homo sapiens

<400> SEQUENCE: 69
cctaggaaga ggtagtaggt tgcatagttt tagggcaggg attttgccca caaggaggta    60
actatacgac ctgctgcctt tcttagg                                        87

<210> SEQ ID NO 70
<211> LENGTH: 85
<212> TYPE: DNA
<213> ORGANISM: Homo sapiens

<400> SEQUENCE: 70
ctaggaagag gtagtagttt gcatagtttt agggcaaaga ttttgcccac aagtagttag    60
ctatacgacc tgcagccttt tgtag                                          85

<210> SEQ ID NO 71
```

```
<211> LENGTH: 85
<212> TYPE: DNA
<213> ORGANISM: Homo sapiens

<400> SEQUENCE: 71
ctggctgagg tagtagtttg tgctgttggt cgggttgtga cattgcccgc tgtggagata    60
actgcgcaag ctactgcctt gctag                                         85

<210> SEQ ID NO 72
<211> LENGTH: 79
<212> TYPE: DNA
<213> ORGANISM: Homo sapiens

<400> SEQUENCE: 72
cccgggctga ggtaggaggt tgtatagttg aggaggacac ccaaggagat cactatacgg    60
cctcctagct ttccccagg                                                79

<210> SEQ ID NO 73
<211> LENGTH: 87
<212> TYPE: DNA
<213> ORGANISM: Homo sapiens

<400> SEQUENCE: 73
tcagagtgag gtagtagatt gtatagttgt ggggtagtga ttttaccctg ttcaggagat    60
aactatacaa tctattgcct tccctga                                       87

<210> SEQ ID NO 74
<211> LENGTH: 89
<212> TYPE: DNA
<213> ORGANISM: Homo sapiens

<400> SEQUENCE: 74
ctgtgggatg aggtagtaga ttgtatagtt gtggggtagt gattttaccc tgttcaggag    60
ataactatac aatctattgc cttccctga                                     89

<210> SEQ ID NO 75
<211> LENGTH: 85
<212> TYPE: DNA
<213> ORGANISM: Homo sapiens

<400> SEQUENCE: 75
ctgtgggatg aggtagtaga ttgtatagtt ttagggtcat accccatctt ggagataact    60
atacagtcta ctgtctttcc cacgg                                         85

<210> SEQ ID NO 76
<211> LENGTH: 108
<212> TYPE: DNA
<213> ORGANISM: Homo sapiens

<400> SEQUENCE: 76
ttgcctgatt ccaggctgag gtagtagttt gtacagtttg agggtctatg ataccacccg    60
gtacaggaga taactgtaca ggccactgcc ttgccaggaa cagcgcgc               108

<210> SEQ ID NO 77
<211> LENGTH: 85
<212> TYPE: DNA
<213> ORGANISM: Homo sapiens

<400> SEQUENCE: 77
ctggctgagg tagtagtttg tgctgttggt cgggttgtga cattgcccgc tgtggagata    60
```

-continued actgcgcaag ctactgcctt gctag                                              85

<210> SEQ ID NO 78
<211> LENGTH: 85
<212> TYPE: DNA
<213> ORGANISM: Homo sapiens

<400> SEQUENCE: 78
acctactcag agtacatact tctttatgta cccatatgaa catacaatgc tatggaatgt        60
aaagaagtat gtattttgg taggc                                               85

<210> SEQ ID NO 79
<211> LENGTH: 108
<212> TYPE: DNA
<213> ORGANISM: Homo sapiens

<400> SEQUENCE: 79
cagctaacaa cttagtaata cctactcaga gtacatactt ctttatgtac ccatatgaac        60
atacaatgct atggaatgta aagaagtatg tattttggt aggcaata                     108

<210> SEQ ID NO 80
<211> LENGTH: 85
<212> TYPE: DNA
<213> ORGANISM: Homo sapiens

<400> SEQUENCE: 80
gcctgcttgg gaaacatact tctttatatg cccatatgga cctgctaagc tatggaatgt        60
aaagaagtat gtatctcagg ccggg                                              85

<210> SEQ ID NO 81
<211> LENGTH: 71
<212> TYPE: DNA
<213> ORGANISM: Homo sapiens

<400> SEQUENCE: 81
tgggaaacat acttctttat atgcccatat ggacctgcta agctatggaa tgtaaagaag        60
tatgtatctc a                                                             71

<210> SEQ ID NO 82
<211> LENGTH: 85
<212> TYPE: DNA
<213> ORGANISM: Homo sapiens

<400> SEQUENCE: 82
acctactcag agtacatact tctttatgta cccatatgaa catacaatgc tatggaatgt        60
aaagaagtat gtattttgg taggc                                               85

<210> SEQ ID NO 83
<211> LENGTH: 108
<212> TYPE: DNA
<213> ORGANISM: Homo sapiens

<400> SEQUENCE: 83
tggatgttgg cctagttctg tgtggaagac tagtgatttt gttgttttta gataactaaa        60
tcgacaacaa atcacagtct gccatatggc acaggccatg cctctaca                    108

<210> SEQ ID NO 84
<211> LENGTH: 110
<212> TYPE: DNA

<213> ORGANISM: Homo sapiens

<400> SEQUENCE: 84
ttggatgttg gcctagttct gtgtggaaga ctagtgattt tgttgttttt agataactaa     60
atcgacaaca aatcacagtc tgccatatgg cacaggccat gcctctacag              110

<210> SEQ ID NO 85
<211> LENGTH: 110
<212> TYPE: DNA
<213> ORGANISM: Homo sapiens

<400> SEQUENCE: 85
ctggatacag agtggaccgg ctggccccat ctggaagact agtgattttg ttgttgtctt     60
actgcgctca acaacaaatc ccagtctacc taatggtgcc agccatcgca              110

<210> SEQ ID NO 86
<211> LENGTH: 110
<212> TYPE: DNA
<213> ORGANISM: Homo sapiens

<400> SEQUENCE: 86
agattagagt ggctgtggtc tagtgctgtg tggaagacta gtgattttgt tgttctgatg     60
tactacgaca acaagtcaca gccggcctca tagcgcagac tcccttcgac              110

<210> SEQ ID NO 87
<211> LENGTH: 89
<212> TYPE: DNA
<213> ORGANISM: Homo sapiens

<400> SEQUENCE: 87
cggggttggt tgttatcttt ggttatctag ctgtatgagt ggtgtggagt cttcataaag     60
ctagataacc gaaagtaaaa ataacccca                                      89

<210> SEQ ID NO 88
<211> LENGTH: 87
<212> TYPE: DNA
<213> ORGANISM: Homo sapiens

<400> SEQUENCE: 88
ggaagcgagt tgttatcttt ggttatctag ctgtatgagt gtattggtct tcataaagct     60
agataaccga agtaaaaac tccttca                                         87

<210> SEQ ID NO 89
<211> LENGTH: 90
<212> TYPE: DNA
<213> ORGANISM: Homo sapiens

<400> SEQUENCE: 89
ggaggcccgt ttctctcttt ggttatctag ctgtatgagt gccacagagc cgtcataaag     60
ctagataacc gaaagtagaa atgattctca                                     90

<210> SEQ ID NO 90
<211> LENGTH: 110
<212> TYPE: DNA
<213> ORGANISM: Homo sapiens

<400> SEQUENCE: 90
gatctgtctg tcttctgtat ataccctgta gatccgaatt tgtgtaagga attttgtggt     60
cacaaattcg tatctagggg aatatgtagt tgacataaac actccgctct              110

<210> SEQ ID NO 91
<211> LENGTH: 110
<212> TYPE: DNA
<213> ORGANISM: Homo sapiens

<400> SEQUENCE: 91
ccagaggttg taacgttgtc tatatatacc ctgtagaacc gaatttgtgt ggtatccgta      60
tagtcacaga ttcgattcta ggggaatata tggtcgatgc aaaaacttca                110

<210> SEQ ID NO 92
<211> LENGTH: 108
<212> TYPE: DNA
<213> ORGANISM: Homo sapiens

<400> SEQUENCE: 92
gcgcgaatgt gtgtttaaaa aaaataaaac cttggagtaa agtagcagca cataatggtt      60
tgtggatttt gaaaaggtgc aggccatatt gtgctgcctc aaaaatac                  108

<210> SEQ ID NO 93
<211> LENGTH: 83
<212> TYPE: DNA
<213> ORGANISM: Homo sapiens

<400> SEQUENCE: 93
ccttggagta agtagcagc acataatggt tgtggatttt gaaaaggtg caggccatat        60 tgtgctgcct caaaaataca agg                                              83

<210> SEQ ID NO 94
<211> LENGTH: 64
<212> TYPE: DNA
<213> ORGANISM: Homo sapiens

<400> SEQUENCE: 94
ctgtagcagc acatcatggt ttacatgcta cagtcaagat gcgaatcatt atttgctgct      60
ctag                                                                   64

<210> SEQ ID NO 95
<211> LENGTH: 98
<212> TYPE: DNA
<213> ORGANISM: Homo sapiens

<400> SEQUENCE: 95
ttgaggcctt aaagtactgt agcagcacat catggtttac atgctacagt caagatgcga      60
atcattattt gctgctctag aaatttaagg aaattcat                              98

<210> SEQ ID NO 96
<211> LENGTH: 89
<212> TYPE: DNA
<213> ORGANISM: Homo sapiens

<400> SEQUENCE: 96
gtcagcagtg ccttagcagc acgtaaatat tggcgttaag attctaaaat tatctccagt      60
attaactgtg ctgctgaagt aaggttgac                                        89

<210> SEQ ID NO 97
<211> LENGTH: 81
<212> TYPE: DNA
<213> ORGANISM: Homo sapiens

```
<400> SEQUENCE: 97
gttccactct agcagcacgt aaatattggc gtagtgaaat atatattaaa caccaatatt    60
actgtgctgc tttagtgtga c                                             81

<210> SEQ ID NO 98
<211> LENGTH: 81
<212> TYPE: DNA
<213> ORGANISM: Homo sapiens

<400> SEQUENCE: 98
gcagtgcctt agcagcacgt aaatattggc gttaagattc taaaattatc tccagtatta    60
actgtgctgc tgaagtaagg t                                             81

<210> SEQ ID NO 99
<211> LENGTH: 84
<212> TYPE: DNA
<213> ORGANISM: Homo sapiens

<400> SEQUENCE: 99
gtcagaataa tgtcaaagtg cttacagtgc aggtagtgat atgtgcatct actgcagtga    60
aggcacttgt agcattatgg tgac                                          84

<210> SEQ ID NO 100
<211> LENGTH: 71
<212> TYPE: DNA
<213> ORGANISM: Homo sapiens

<400> SEQUENCE: 100
tgttctaagg tgcatctagt gcagatagtg aagtagatta gcatctactg ccctaagtgc    60
tccttctggc a                                                        71

<210> SEQ ID NO 101
<211> LENGTH: 81
<212> TYPE: DNA
<213> ORGANISM: Homo sapiens

<400> SEQUENCE: 101
tttttgttct aaggtgcatc tagtgcagat agtgaagtag attagcatct actgccctaa    60
gtgctccttc tggcataaga a                                             81

<210> SEQ ID NO 102
<211> LENGTH: 82
<212> TYPE: DNA
<213> ORGANISM: Homo sapiens

<400> SEQUENCE: 102
gcagtcctct gttagttttg catagttgca ctacaagaag aatgtagttg tgcaaatcta    60
tgcaaaactg atggtggcct gc                                            82

<210> SEQ ID NO 103
<211> LENGTH: 80
<212> TYPE: DNA
<213> ORGANISM: Homo sapiens

<400> SEQUENCE: 103
cagtcctctg ttagttttgc atagttgcac tacaagaaga atgtagttgt gcaaatctat    60
gcaaaactga tggtggcctg                                               80
```

<210> SEQ ID NO 104
<211> LENGTH: 87
<212> TYPE: DNA
<213> ORGANISM: Homo sapiens

<400> SEQUENCE: 104
cactgttcta tggttagttt tgcaggtttg catccagctg tgtgatattc tgctgtgcaa      60
atccatgcaa aactgactgt ggtagtg                                         87

<210> SEQ ID NO 105
<211> LENGTH: 96
<212> TYPE: DNA
<213> ORGANISM: Homo sapiens

<400> SEQUENCE: 105
acattgctac ttacaattag ttttgcaggt ttgcatttca gcgtatatat gtatatgtgg      60
ctgtgcaaat ccatgcaaaa ctgattgtga taatgt                               96

<210> SEQ ID NO 106
<211> LENGTH: 80
<212> TYPE: DNA
<213> ORGANISM: Homo sapiens

<400> SEQUENCE: 106
ttctatggtt agttttgcag gtttgcatcc agctgtgtga tattctgctg tgcaaatcca      60
tgcaaaactg actgtggtag                                                 80

<210> SEQ ID NO 107
<211> LENGTH: 81
<212> TYPE: DNA
<213> ORGANISM: Homo sapiens

<400> SEQUENCE: 107
ttacaattag ttttgcaggt ttgcatttca gcgtatatat gtatatgtgg ctgtgcaaat      60
ccatgcaaaa ctgattgtga t                                               81

<210> SEQ ID NO 108
<211> LENGTH: 71
<212> TYPE: DNA
<213> ORGANISM: Homo sapiens

<400> SEQUENCE: 108
gtagcactaa agtgcttata gtgcaggtag tgtttagtta tctactgcat tatgagcact      60
taaagtactg c                                                          71

<210> SEQ ID NO 109
<211> LENGTH: 72
<212> TYPE: DNA
<213> ORGANISM: Homo sapiens

<400> SEQUENCE: 109
tgtcgggtag cttatcagac tgatgttgac tgttgaatct catggcaaca ccagtcgatg      60
ggctgtctga ca                                                         72

<210> SEQ ID NO 110
<211> LENGTH: 81
<212> TYPE: DNA
<213> ORGANISM: Homo sapiens

<400> SEQUENCE: 110
accttgtcgg gtagcttatc agactgatgt tgactgttga atctcatggc aacaccagtc    60
gatgggctgt ctgacattt g                                               81

<210> SEQ ID NO 111
<211> LENGTH: 85
<212> TYPE: DNA
<213> ORGANISM: Homo sapiens

<400> SEQUENCE: 111
ggctgagccg cagtagttct tcagtggcaa gctttatgtc ctgacccagc taaagctgcc    60
agttgaagaa ctgttgccct ctgcc                                          85

<210> SEQ ID NO 112
<211> LENGTH: 73
<212> TYPE: DNA
<213> ORGANISM: Homo sapiens

<400> SEQUENCE: 112
ggccggctgg ggttcctggg gatgggattt gcttcctgtc acaaatcaca ttgccaggga    60
tttccaaccg acc                                                       73

<210> SEQ ID NO 113
<211> LENGTH: 97
<212> TYPE: DNA
<213> ORGANISM: Homo sapiens

<400> SEQUENCE: 113
ctcaggtgct ctggctgctt gggttcctgg catgctgatt tgtgacttaa gattaaaatc    60
acattgccag ggattaccac gcaaccacga ccttggc                             97

<210> SEQ ID NO 114
<211> LENGTH: 81
<212> TYPE: DNA
<213> ORGANISM: Homo sapiens

<400> SEQUENCE: 114
ccacggccgg ctggggttcc tggggatggg atttgcttcc tgtcacaaat cacattgcca    60
gggatttcca accgaccctg a                                              81

<210> SEQ ID NO 115
<211> LENGTH: 68
<212> TYPE: DNA
<213> ORGANISM: Homo sapiens

<400> SEQUENCE: 115
ctccggtgcc tactgagctg atatcagttc tcattttaca cactggctca gttcagcagg    60
aacaggag                                                             68

<210> SEQ ID NO 116
<211> LENGTH: 73
<212> TYPE: DNA
<213> ORGANISM: Homo sapiens

<400> SEQUENCE: 116
ctctgcctcc cgtgcctact gagctgaaac acagttggtt tgtgtacact ggctcagttc    60
agcaggaaca ggg                                                       73

<210> SEQ ID NO 117
<211> LENGTH: 81

<212> TYPE: DNA
<213> ORGANISM: Homo sapiens

<400> SEQUENCE: 117
ccctgggctc tgcctcccgt gcctactgag ctgaaacaca gttggtttgt gtacactggc    60
tcagttcagc aggaacaggg g                                              81

<210> SEQ ID NO 118
<211> LENGTH: 71
<212> TYPE: DNA
<213> ORGANISM: Homo sapiens

<400> SEQUENCE: 118
ccctccggtg cctactgagc tgatatcagt tctcatttta cacactggct cagttcagca    60
ggaacagcat c                                                         71

<210> SEQ ID NO 119
<211> LENGTH: 84
<212> TYPE: DNA
<213> ORGANISM: Homo sapiens

<400> SEQUENCE: 119
ggccagtgtt gagaggcgga gacttgggca attgctggac gctgccctgg gcattgcact    60
tgtctcggtc tgacagtgcc ggcc                                           84

<210> SEQ ID NO 120
<211> LENGTH: 86
<212> TYPE: DNA
<213> ORGANISM: Homo sapiens

<400> SEQUENCE: 120
aggccgtggc ctcgttcaag taatccagga taggctgtgc aggtcccaat ggcctatctt    60
ggttacttgc acggggacgc gggcct                                         86

<210> SEQ ID NO 121
<211> LENGTH: 77
<212> TYPE: DNA
<213> ORGANISM: Homo sapiens

<400> SEQUENCE: 121
ccgggaccca gttcaagtaa ttcaggatag gttgtgtgct gtccagcctg ttctccatta    60
cttggctcgg ggaccgg                                                   77

<210> SEQ ID NO 122
<211> LENGTH: 78
<212> TYPE: DNA
<213> ORGANISM: Homo sapiens

<400> SEQUENCE: 122
ctgaggagca gggcttagct gcttgtgagc agggtccaca ccaagtcgtg ttcacagtgg    60
ctaagttccg cccccccag                                                 78

<210> SEQ ID NO 123
<211> LENGTH: 73
<212> TYPE: DNA
<213> ORGANISM: Homo sapiens

<400> SEQUENCE: 123
aggtgcagag cttagctgat tggtgaacag tgattggttt ccgctttgtt cacagtggct    60

-continued aagttctgca cct                                                                73

<210> SEQ ID NO 124
<211> LENGTH: 97
<212> TYPE: DNA
<213> ORGANISM: Homo sapiens

<400> SEQUENCE: 124
acctctctaa caaggtgcag agcttagctg attggtgaac agtgattggt ttccgctttg      60
ttcacagtgg ctaagttctg cacctgaaga gaaggtg                              97

<210> SEQ ID NO 125
<211> LENGTH: 80
<212> TYPE: DNA
<213> ORGANISM: Homo sapiens

<400> SEQUENCE: 125
cctgaggagc agggcttagc tgcttgtgag cagggtccac accaagtcgt gttcacagtg      60
gctaagttcc gcccccccagg                                                80

<210> SEQ ID NO 126
<211> LENGTH: 86
<212> TYPE: DNA
<213> ORGANISM: Homo sapiens

<400> SEQUENCE: 126
ggtccttgcc ctcaaggagc tcacagtcta ttgagttacc tttctgactt tcccactaga      60
ttgtgagctc ctggagggca ggcact                                          86

<210> SEQ ID NO 127
<211> LENGTH: 108
<212> TYPE: DNA
<213> ORGANISM: Homo sapiens

<400> SEQUENCE: 127
ccttctgtga ccccttagag gatgactgat ttcttttggt gttcagagtc aatataattt     60
tctagcacca tctgaaatcg gttataatga ttggggaaga gcaccatg                  108

<210> SEQ ID NO 128
<211> LENGTH: 64
<212> TYPE: DNA
<213> ORGANISM: Homo sapiens

<400> SEQUENCE: 128
atgactgatt tcttttggtg ttcagagtca atataatttt ctagcaccat ctgaaatcgg     60
ttat                                                                  64

<210> SEQ ID NO 129
<211> LENGTH: 110
<212> TYPE: DNA
<213> ORGANISM: Homo sapiens

<400> SEQUENCE: 129
accactggcc catctcttac acaggctgac cgatttctcc tggtgttcag agtctgtttt     60
tgtctagcac catttgaaat cggttatgat gtaggggaa aagcagcagc                 110

<210> SEQ ID NO 130
<211> LENGTH: 71
<212> TYPE: DNA
<213> ORGANISM: Homo sapiens

<400> SEQUENCE: 130
gcgactgtaa acatcctcga ctggaagctg tgaagccaca gatgggcttt cagtcggatg    60
tttgcagctg c    71

<210> SEQ ID NO 131
<211> LENGTH: 60
<212> TYPE: DNA
<213> ORGANISM: Homo sapiens

<400> SEQUENCE: 131
atgtaaacat cctacactca gctgtaatac atggattggc tgggaggtgg atgtttacgt    60

<210> SEQ ID NO 132
<211> LENGTH: 88
<212> TYPE: DNA
<213> ORGANISM: Homo sapiens

<400> SEQUENCE: 132
accaagtttc agttcatgta aacatcctac actcagctgt aatacatgga ttggctggga    60
ggtggatgtt tacttcagct gacttgga    88

<210> SEQ ID NO 133
<211> LENGTH: 72
<212> TYPE: DNA
<213> ORGANISM: Homo sapiens

<400> SEQUENCE: 133
agatactgta aacatcctac actctcagct gtggaaagta agaaagctgg gagaaggctg    60
tttactcttt ct    72

<210> SEQ ID NO 134
<211> LENGTH: 70
<212> TYPE: DNA
<213> ORGANISM: Homo sapiens

<400> SEQUENCE: 134
gttgttgtaa acatccccga ctggaagctg taagacacag ctaagctttc agtcagatgt    60
ttgctgctac    70

<210> SEQ ID NO 135
<211> LENGTH: 71
<212> TYPE: DNA
<213> ORGANISM: Homo sapiens

<400> SEQUENCE: 135
ggagaggagg caagatgctg gcatagctgt tgaactggga acctgctatg ccaacatatt    60
gccatctttc c    71

<210> SEQ ID NO 136
<211> LENGTH: 70
<212> TYPE: DNA
<213> ORGANISM: Homo sapiens

<400> SEQUENCE: 136
ggagatattg cacattacta agttgcatgt tgtcacggcc tcaatgcaat ttagtgtgtg    60
tgatattttc    70

<210> SEQ ID NO 137

```
<211> LENGTH: 110
<212> TYPE: DNA
<213> ORGANISM: Homo sapiens

<400> SEQUENCE: 137
gggggccgag agaggcgggc ggccccgcgg tgcattgctg ttgcattgca cgtgtgtgag      60
gcgggtgcag tgcctcggca gtgcagcccg gagccggccc ctggcaccac                110

<210> SEQ ID NO 138
<211> LENGTH: 69
<212> TYPE: DNA
<213> ORGANISM: Homo sapiens

<400> SEQUENCE: 138
ctgtggtgca ttgtagttgc attgcatgtt ctggtggtac ccatgcaatg tttccacagt      60
gcatcacag                                                             69

<210> SEQ ID NO 139
<211> LENGTH: 110
<212> TYPE: DNA
<213> ORGANISM: Homo sapiens

<400> SEQUENCE: 139
ggccagctgt gagtgtttct ttggcagtgt cttagctggt tgttgtgagc aatagtaagg      60
aagcaatcag caagtatact gccctagaag tgctgcacgt tgtggggccc                110

<210> SEQ ID NO 140
<211> LENGTH: 82
<212> TYPE: DNA
<213> ORGANISM: Homo sapiens

<400> SEQUENCE: 140
tcagaataat gtcaaagtgc ttacagtgca ggtagtgata tgtgcatcta ctgcagtgaa      60
ggcacttgta gcattatggt ga                                              82

<210> SEQ ID NO 141
<211> LENGTH: 78
<212> TYPE: DNA
<213> ORGANISM: Homo sapiens

<400> SEQUENCE: 141
ctttctacac aggttgggat cggttgcaat gctgtgtttc tgtatggtat tgcacttgtc      60
ccggcctgtt gagtttgg                                                   78

<210> SEQ ID NO 142
<211> LENGTH: 75
<212> TYPE: DNA
<213> ORGANISM: Homo sapiens

<400> SEQUENCE: 142
tcatccctgg gtgggatttg ttgcattacc ttgtgttcta tataaagtat tgcacttgtc      60
ccggcctgtg gaaga                                                      75

<210> SEQ ID NO 143
<211> LENGTH: 80
<212> TYPE: DNA
<213> ORGANISM: Homo sapiens

<400> SEQUENCE: 143
ctgggggctc caaagtgctg ttcgtgcagg tagtgtgatt acccaaccta ctgctgagct      60
```
agcacttccc gagcccccgg                                                    80

<210> SEQ ID NO 144
<211> LENGTH: 81
<212> TYPE: DNA
<213> ORGANISM: Homo sapiens

<400> SEQUENCE: 144
aacacagtgg gcactcaata aatgtctgtt gaattgaaat gcgttacatt caacgggtat        60
ttattgagca cccactctgt g                                                  81

<210> SEQ ID NO 145
<211> LENGTH: 78
<212> TYPE: DNA
<213> ORGANISM: Homo sapiens

<400> SEQUENCE: 145
tggccgattt tggcactagc acattttgc ttgtgtctct ccgctctgag caatcatgtg         60
cagtgccaat atgggaaa                                                      78

<210> SEQ ID NO 146
<211> LENGTH: 80
<212> TYPE: DNA
<213> ORGANISM: Homo sapiens

<400> SEQUENCE: 146
gtgaggtagt aagttgtatt gttgtggggt agggatatta ggcccccaatt agaagataac      60 tatacaactt actactttcc                                                    80

<210> SEQ ID NO 147
<211> LENGTH: 70
<212> TYPE: DNA
<213> ORGANISM: Homo sapiens

<400> SEQUENCE: 147
ggcacccacc cgtagaaccg accttgcggg gccttcgccg cacacaagct cgtgtctgtg        60
ggtccgtgtc                                                               70

<210> SEQ ID NO 148
<211> LENGTH: 81
<212> TYPE: DNA
<213> ORGANISM: Homo sapiens

<400> SEQUENCE: 148
cccattggca taaacccgta gatccgatct tgtggtgaag tggaccgcac aagctcgctt        60
ctatgggtct gtgtcagtgt g                                                  81

<210> SEQ ID NO 149
<211> LENGTH: 108
<212> TYPE: DNA
<213> ORGANISM: Homo sapiens

<400> SEQUENCE: 149
aagagagaag atattgaggc ctgttgccac aaacccgtag atccgaactt gtggtattag        60
tccgcacaag cttgtatcta taggtatgtg tctgttaggc aatctcac                    108

<210> SEQ ID NO 150
<211> LENGTH: 80
<212> TYPE: DNA

<213> ORGANISM: Homo sapiens

<400> SEQUENCE: 150
cctgttgcca caacccgta gatccgaact tgtggtatta gtccgcacaa gcttgtatct    60
ataggtatgt gtctgttagg                                              80

<210> SEQ ID NO 151
<211> LENGTH: 110
<212> TYPE: DNA
<213> ORGANISM: Homo sapiens

<400> SEQUENCE: 151
aggctgccct ggctcagtta tcacagtgct gatgctgtct attctaaagg tacagtactg    60
tgataactga aggatggcag ccatcttacc ttccatcaga ggagcctcac              110

<210> SEQ ID NO 152
<211> LENGTH: 57
<212> TYPE: DNA
<213> ORGANISM: Homo sapiens

<400> SEQUENCE: 152
tcagttatca cagtgctgat gctgtccatt ctaaaggtac agtactgtga taactga      57

<210> SEQ ID NO 153
<211> LENGTH: 75
<212> TYPE: DNA
<213> ORGANISM: Homo sapiens

<400> SEQUENCE: 153
tgccctggct cagttatcac agtgctgatg ctgtctattc taaaggtaca gtactgtgat    60
aactgaagga tggca                                                   75

<210> SEQ ID NO 154
<211> LENGTH: 75
<212> TYPE: DNA
<213> ORGANISM: Homo sapiens

<400> SEQUENCE: 154
tgtccttttt cggttatcat ggtaccgatg ctgtatatct gaaaggtaca gtactgtgat    60
aactgaagaa tggtg                                                   75

<210> SEQ ID NO 155
<211> LENGTH: 81
<212> TYPE: DNA
<213> ORGANISM: Homo sapiens

<400> SEQUENCE: 155
cttctggaag ctggtttcac atggtggctt agattttcc atctttgtat ctagcaccat    60
ttgaaatcag tgttttagga g                                            81

<210> SEQ ID NO 156
<211> LENGTH: 81
<212> TYPE: DNA
<213> ORGANISM: Homo sapiens

<400> SEQUENCE: 156
cttcaggaag ctggtttcat atggtggttt agatttaaat agtgattgtc tagcaccatt    60
tgaaatcagt gttcttgggg g                                            81

```
<210> SEQ ID NO 157
<211> LENGTH: 78
<212> TYPE: DNA
<213> ORGANISM: Homo sapiens

<400> SEQUENCE: 157
ttgtgctttc agcttcttta cagtgctgcc ttgtagcatt caggtcaagc aacattgtac      60
agggctatga aagaacca                                                   78

<210> SEQ ID NO 158
<211> LENGTH: 78
<212> TYPE: DNA
<213> ORGANISM: Homo sapiens

<400> SEQUENCE: 158
tactgccctc ggcttcttta cagtgctgcc ttgttgcata tggatcaagc agcattgtac      60
agggctatga aggcattg                                                   78

<210> SEQ ID NO 159
<211> LENGTH: 78
<212> TYPE: DNA
<213> ORGANISM: Homo sapiens

<400> SEQUENCE: 159
aaatgtcaga cagcccatcg actggtgttg ccatgagatt caacagtcaa catcagtctg      60
ataagctacc cgacaagg                                                   78

<210> SEQ ID NO 160
<211> LENGTH: 81
<212> TYPE: DNA
<213> ORGANISM: Homo sapiens

<400> SEQUENCE: 160
tgtgcatcgt ggtcaaatgc tcagactcct gtggtggctg ctcatgcacc acggatgttt      60
gagcatgtgc tacggtgtct a                                               81

<210> SEQ ID NO 161
<211> LENGTH: 81
<212> TYPE: DNA
<213> ORGANISM: Homo sapiens

<400> SEQUENCE: 161
ccttggccat gtaaaagtgc ttacagtgca ggtagctttt tgagatctac tgcaatgtaa      60
gcacttctta cattaccatg g                                               81

<210> SEQ ID NO 162
<211> LENGTH: 81
<212> TYPE: DNA
<213> ORGANISM: Homo sapiens

<400> SEQUENCE: 162
ctctctgctt tcagcttctt tacagtgttg ccttgtggca tggagttcaa gcagcattgt      60
acagggctat caaagcacag a                                               81

<210> SEQ ID NO 163
<211> LENGTH: 85
<212> TYPE: DNA
<213> ORGANISM: Homo sapiens

<400> SEQUENCE: 163
```

```
ccttagcaga gctgtggagt gtgacaatgg tgtttgtgtc taaactatca aacgccatta      60
tcacactaaa tagctactgc taggc                                           85

<210> SEQ ID NO 164
<211> LENGTH: 66
<212> TYPE: DNA
<213> ORGANISM: Homo sapiens

<400> SEQUENCE: 164
agctgtggag tgtgacaatg gtgtttgtgt ccaaactatc aaacgccatt atcacactaa      60
atagct                                                                66

<210> SEQ ID NO 165
<211> LENGTH: 61
<212> TYPE: DNA
<213> ORGANISM: Homo sapiens

<400> SEQUENCE: 165
acattattac ttttggtacg cgctgtgaca cttcaaactc gtaccgtgag taataatgcg      60
c                                                                     61

<210> SEQ ID NO 166
<211> LENGTH: 100
<212> TYPE: DNA
<213> ORGANISM: Homo sapiens

<400> SEQUENCE: 166
tccttcctca ggagaaaggc ctctctctcc gtgttcacag cggaccttga tttaaatgtc      60
catacaatta aggcacgcgg tgaatgccaa gaatggggct                           100

<210> SEQ ID NO 167
<211> LENGTH: 85
<212> TYPE: DNA
<213> ORGANISM: Homo sapiens

<400> SEQUENCE: 167
aggcctctct ctccgtgttc acagcggacc ttgatttaaa tgtccataca attaaggcac      60
gcggtgaatg ccaagaatgg ggctg                                           85

<210> SEQ ID NO 168
<211> LENGTH: 110
<212> TYPE: DNA
<213> ORGANISM: Homo sapiens

<400> SEQUENCE: 168
atcaagatta gaggctctgc tctccgtgtt cacagcggac cttgatttaa tgtcatacaa      60
ttaaggcacg cggtgaatgc caagagcgga gcctacggct gcacttgaag               110

<210> SEQ ID NO 169
<211> LENGTH: 110
<212> TYPE: DNA
<213> ORGANISM: Homo sapiens

<400> SEQUENCE: 169
cccgccccag ccctgagggc ccctctgcgt gttcacagcg gaccttgatt taatgtctat      60
acaattaagg cacgcggtga atgccaagag aggcgcctcc gccgctcctt               110

<210> SEQ ID NO 170
<211> LENGTH: 87
```

<212> TYPE: DNA
<213> ORGANISM: Homo sapiens

<400> SEQUENCE: 170
tgagggcccc tctgcgtgtt cacagcggac cttgatttaa tgtctataca attaaggcac    60
gcggtgaatg ccaagagagg cgcctcc                                       87

<210> SEQ ID NO 171
<211> LENGTH: 68
<212> TYPE: DNA
<213> ORGANISM: Homo sapiens

<400> SEQUENCE: 171
ctctgcgtgt tcacagcgga ccttgattta atgtctatac aattaaggca cgcggtgaat    60
gccaagag                                                            68

<210> SEQ ID NO 172
<211> LENGTH: 67
<212> TYPE: DNA
<213> ORGANISM: Homo sapiens

<400> SEQUENCE: 172
ctctccgtgt tcacagcgga ccttgattta atgtcataca attaaggcac gcggtgaatg    60
ccaagag                                                             67

<210> SEQ ID NO 173
<211> LENGTH: 86
<212> TYPE: DNA
<213> ORGANISM: Homo sapiens

<400> SEQUENCE: 173
tgccagtctc taggtccctg agacccttta acctgtgagg acatccaggg tcacaggtga    60
ggttcttggg agcctggcgt ctggcc                                        86

<210> SEQ ID NO 174
<211> LENGTH: 65
<212> TYPE: DNA
<213> ORGANISM: Homo sapiens

<400> SEQUENCE: 174
ggtccctgag acccttaac ctgtgaggac atccagggtc acaggtgagg ttcttgggag    60
cctgg                                                               65

<210> SEQ ID NO 175
<211> LENGTH: 108
<212> TYPE: DNA
<213> ORGANISM: Homo sapiens

<400> SEQUENCE: 175
acattgttgc gctcctctca gtccctgaga ccctaacttg tgatgtttac cgtttaaatc    60
cacgggttag gctcttggga gctgcgagtc gtgcttttgc atcctgga               108

<210> SEQ ID NO 176
<211> LENGTH: 88
<212> TYPE: DNA
<213> ORGANISM: Homo sapiens

<400> SEQUENCE: 176
tgcgctcctc tcagtccctg agaccctaac ttgtgatgtt taccgtttaa atccacgggt    60
taggctcttg ggagctgcga gtcgtgct                                              88

<210> SEQ ID NO 177
<211> LENGTH: 89
<212> TYPE: DNA
<213> ORGANISM: Homo sapiens

<400> SEQUENCE: 177
accagacttt tcctagtccc tgagaccta acttgtgagg tattttagta acatcacaag            60
tcaggctctt gggacctagg cggagggga                                             89

<210> SEQ ID NO 178
<211> LENGTH: 70
<212> TYPE: DNA
<213> ORGANISM: Homo sapiens

<400> SEQUENCE: 178
cctagtccct gagaccctaa cttgtgaggt attttagtaa catcacaagt caggctcttg           60
ggacctaggc                                                                  70

<210> SEQ ID NO 179
<211> LENGTH: 85
<212> TYPE: DNA
<213> ORGANISM: Homo sapiens

<400> SEQUENCE: 179
cgctggcgac gggacattat tactttggt acgcgctgtg acacttcaaa ctcgtaccgt            60
gagtaataat gcgccgtcca cggca                                                 85

<210> SEQ ID NO 180
<211> LENGTH: 61
<212> TYPE: DNA
<213> ORGANISM: Homo sapiens

<400> SEQUENCE: 180
acattattac ttttggtacg cgctgtgaca cttcaaactc gtaccgtgag taataatgcg           60
c                                                                           61

<210> SEQ ID NO 181
<211> LENGTH: 97
<212> TYPE: DNA
<213> ORGANISM: Homo sapiens

<400> SEQUENCE: 181
tgtgatcact gtctccagcc tgctgaagct cagagggctc tgattcagaa agatcatcgg           60
atccgtctga gcttggctgg tcggaagtct catcatc                                    97

<210> SEQ ID NO 182
<211> LENGTH: 70
<212> TYPE: DNA
<213> ORGANISM: Homo sapiens

<400> SEQUENCE: 182
ccagcctgct gaagctcaga gggctctgat tcagaaagat catcggatcc gtctgagctt           60
ggctggtcgg                                                                  70

<210> SEQ ID NO 183
<211> LENGTH: 82
<212> TYPE: DNA
<213> ORGANISM: Homo sapiens

<400> SEQUENCE: 183
tgagctgttg gattcggggc cgtagcactg tctgagaggt ttacatttct cacagtgaac    60
cggtctcttt ttcagctgct tc                                             82

<210> SEQ ID NO 184
<211> LENGTH: 110
<212> TYPE: DNA
<213> ORGANISM: Homo sapiens

<400> SEQUENCE: 184
gcccggcagc cactgtgcag tgggaagggg ggccgataca ctgtacgaga gtgagtagca    60
ggtctcacag tgaaccggtc tctttcccta ctgtgtcaca ctcctaatgg              110

<210> SEQ ID NO 185
<211> LENGTH: 70
<212> TYPE: DNA
<213> ORGANISM: Homo sapiens

<400> SEQUENCE: 185
gttggattcg gggccgtagc actgtctgag aggtttacat ttctcacagt gaaccggtct    60 cttttttcagc                                                           70

<210> SEQ ID NO 186
<211> LENGTH: 74
<212> TYPE: DNA
<213> ORGANISM: Homo sapiens

<400> SEQUENCE: 186
tggatctttt tgcggtctgg gcttgctgtt cctctcaaca gtagtcagga agcccttacc    60
ccaaaaagta tcta                                                       74

<210> SEQ ID NO 187
<211> LENGTH: 89
<212> TYPE: DNA
<213> ORGANISM: Homo sapiens

<400> SEQUENCE: 187
tgctgctggc cagagctctt ttcacattgt gctactgtct gcacctgtca ctagcagtgc    60
aatgttaaaa gggcattggc cgtgtagtg                                       89

<210> SEQ ID NO 188
<211> LENGTH: 110
<212> TYPE: DNA
<213> ORGANISM: Homo sapiens

<400> SEQUENCE: 188
gccaggaggc ggggttggtt gttatctttg gttatctagc tgtatgagtg gtgtggagtc    60
ttcataaagc tagataaccg aaagtaaaaa taccccata cactgcgcag                110

<210> SEQ ID NO 189
<211> LENGTH: 110
<212> TYPE: DNA
<213> ORGANISM: Homo sapiens

<400> SEQUENCE: 189
cacggcgcgg cagcggcact ggctaaggga ggcccgtttc tctctttggt tatctagctg    60
tatgagtgcc acagagccgt cataaagcta gataaccgaa agtagaaatg              110

<210> SEQ ID NO 190
<211> LENGTH: 72
<212> TYPE: DNA
<213> ORGANISM: Homo sapiens

<400> SEQUENCE: 190
gttgttatct ttggttatct agctgtatga gtgtattggt cttcataaag ctagataacc        60
gaaagtaaaa ac                                                            72

<210> SEQ ID NO 191
<211> LENGTH: 101
<212> TYPE: DNA
<213> ORGANISM: Homo sapiens

<400> SEQUENCE: 191
ccgcccccgc gtctccaggg caaccgtggc tttcgattgt tactgtggga actggaggta        60
acagtctaca gccatggtcg ccccgcagca cgcccacgcg c                           101

<210> SEQ ID NO 192
<211> LENGTH: 66
<212> TYPE: DNA
<213> ORGANISM: Homo sapiens

<400> SEQUENCE: 192
gggcaaccgt ggctttcgat tgttactgtg ggaactggag gtaacagtct acagccatgg        60
tcgccc                                                                   66

<210> SEQ ID NO 193
<211> LENGTH: 88
<212> TYPE: DNA
<213> ORGANISM: Homo sapiens

<400> SEQUENCE: 193
acaatgcttt gctagagctg gtaaaatgga accaaatcgc ctcttcaatg gatttggtcc        60
ccttcaacca gctgtagcta tgcattga                                           88

<210> SEQ ID NO 194
<211> LENGTH: 102
<212> TYPE: DNA
<213> ORGANISM: Homo sapiens

<400> SEQUENCE: 194
gggagccaaa tgctttgcta gagctggtaa aatggaacca atcgactgt ccaatggatt         60 tggtcccctt caaccagctg tagctgtgca ttgatggcgc cg                          102

<210> SEQ ID NO 195
<211> LENGTH: 68
<212> TYPE: DNA
<213> ORGANISM: Homo sapiens

<400> SEQUENCE: 195
gctagagctg gtaaaatgga accaaatcgc ctcttcaatg gatttggtcc ccttcaacca        60
gctgtagc                                                                 68

<210> SEQ ID NO 196
<211> LENGTH: 73
<212> TYPE: DNA
<213> ORGANISM: Homo sapiens

<400> SEQUENCE: 196

```
cagggtgtgt gactggttga ccagaggggc atgcactgtg ttcaccctgt gggccaccta    60
gtcaccaacc ctc                                                       73

<210> SEQ ID NO 197
<211> LENGTH: 71
<212> TYPE: DNA
<213> ORGANISM: Homo sapiens

<400> SEQUENCE: 197
agggtgtgtg actggttgac cagaggggca tgcactgtgt tcaccctgtg gccacctag    60 tcaccaaccc t                                                         71

<210> SEQ ID NO 198
<211> LENGTH: 90
<212> TYPE: DNA
<213> ORGANISM: Homo sapiens

<400> SEQUENCE: 198
aggcctcgct gttctctatg gcttttatt cctatgtgat tctactgctc actcatatag    60
ggattggagc cgtggcgcac ggcggggaca                                     90

<210> SEQ ID NO 199
<211> LENGTH: 100
<212> TYPE: DNA
<213> ORGANISM: Homo sapiens

<400> SEQUENCE: 199
agataaattc actctagtgc tttatggctt tttattccta tgtgatagta ataaagtctc    60
atgtagggat ggaagccatg aaatacattg tgaaaaatca                         100

<210> SEQ ID NO 200
<211> LENGTH: 60
<212> TYPE: DNA
<213> ORGANISM: Homo sapiens

<400> SEQUENCE: 200
ctatggcttt ttattcctat gtgattctac tgctcactca tatagggatt ggagccgtgg    60

<210> SEQ ID NO 201
<211> LENGTH: 82
<212> TYPE: DNA
<213> ORGANISM: Homo sapiens

<400> SEQUENCE: 201
tgagccctcg gaggactcca tttgttttga tgatggattc ttatgctcca tcatcgtctc    60
aaatgagtct tcagagggtt ct                                             82

<210> SEQ ID NO 202
<211> LENGTH: 62
<212> TYPE: DNA
<213> ORGANISM: Homo sapiens

<400> SEQUENCE: 202
gaggactcca tttgttttga tgatggattc ttatgctcca tcatcgtctc aaatgagtct    60
tc                                                                   62

<210> SEQ ID NO 203
<211> LENGTH: 73
<212> TYPE: DNA
```

<213> ORGANISM: Homo sapiens

<400> SEQUENCE: 203
cttcggtgac gggtattctt ggtggataa tacggattac gttgttattg cttaagaata    60
cgcgtagtcg agg                                                       73

<210> SEQ ID NO 204
<211> LENGTH: 99
<212> TYPE: DNA
<213> ORGANISM: Homo sapiens

<400> SEQUENCE: 204
ccctggcatg gtgtggtggg gcagctggtg ttgtgaatca ggccgttgcc aatcagagaa    60
cggctacttc acaacaccag ggccacacca cactacagg                           99

<210> SEQ ID NO 205
<211> LENGTH: 84
<212> TYPE: DNA
<213> ORGANISM: Homo sapiens

<400> SEQUENCE: 205
cgttgctgca gctggtgttg tgaatcaggc cgacgagcag cgcatcctct tacccggcta    60
tttcacgaca ccagggttgc atca                                           84

<210> SEQ ID NO 206
<211> LENGTH: 71
<212> TYPE: DNA
<213> ORGANISM: Homo sapiens

<400> SEQUENCE: 206
cagctggtgt tgtgaatcag gccgacgagc agcgcatcct cttacccggc tatttcacga    60
caccagggtt g                                                         71

<210> SEQ ID NO 207
<211> LENGTH: 68
<212> TYPE: DNA
<213> ORGANISM: Homo sapiens

<400> SEQUENCE: 207
gtgtattcta cagtgcacgt gtctccagtg tggctcggag gctggagacg cggccctgtt    60
ggagtaac                                                             68

<210> SEQ ID NO 208
<211> LENGTH: 100
<212> TYPE: DNA
<213> ORGANISM: Homo sapiens

<400> SEQUENCE: 208
tgtgtctctc tctgtgtcct gccagtggtt ttaccctatg gtaggttacg tcatgctgtt    60
ctaccacagg gtagaaccac ggacaggata ccggggcacc                         100

<210> SEQ ID NO 209
<211> LENGTH: 72
<212> TYPE: DNA
<213> ORGANISM: Homo sapiens

<400> SEQUENCE: 209
tcctgccagt ggttttaccc tatggtaggt tacgtcatgc tgttctacca cagggtagaa    60
ccacggacag ga                                                        72

<210> SEQ ID NO 210
<211> LENGTH: 70
<212> TYPE: DNA
<213> ORGANISM: Homo sapiens

<400> SEQUENCE: 210
cctgccagtg gttttaccct atggtaggtt acgtcatgct gttctaccac agggtagaac    60
cacggacagg                                                          70

<210> SEQ ID NO 211
<211> LENGTH: 95
<212> TYPE: DNA
<213> ORGANISM: Homo sapiens

<400> SEQUENCE: 211
cggccggccc tgggtccatc ttccagtaca gtgttggatg gtctaattgt gaagctccta    60
acactgtctg gtaaagatgg ctcccgggtg ggttc                              95

<210> SEQ ID NO 212
<211> LENGTH: 72
<212> TYPE: DNA
<213> ORGANISM: Homo sapiens

<400> SEQUENCE: 212
gggtccatct tccagtacag tgttggatgg tctaattgtg aagctcctaa cactgtctgg    60
taaagatggc cc                                                       72

<210> SEQ ID NO 213
<211> LENGTH: 64
<212> TYPE: DNA
<213> ORGANISM: Homo sapiens

<400> SEQUENCE: 213
acccataaag tagaaagcac tactaacagc actggagggt gtagtgtttc ctactttatg    60
gatg                                                                64

<210> SEQ ID NO 214
<211> LENGTH: 64
<212> TYPE: DNA
<213> ORGANISM: Homo sapiens

<400> SEQUENCE: 214
acccataaag tagaaagcac tactaacagc actggagggt gtagtgtttc ctactttatg    60
gatg                                                                64

<210> SEQ ID NO 215
<211> LENGTH: 106
<212> TYPE: DNA
<213> ORGANISM: Homo sapiens

<400> SEQUENCE: 215
gcgcagcgcc ctgtctccca gcctgaggtg cagtgctgca tctctggtca gttgggagtc    60
tgagatgaag cactgtagct caggaagaga gaagttgttc tgcagc                  106

<210> SEQ ID NO 216
<211> LENGTH: 63
<212> TYPE: DNA
<213> ORGANISM: Homo sapiens

```
<400> SEQUENCE: 216
cctgaggtgc agtgctgcat ctctggtcag ttgggagtct gagatgaagc actgtagctc    60
agg                                                                  63

<210> SEQ ID NO 217
<211> LENGTH: 86
<212> TYPE: DNA
<213> ORGANISM: Homo sapiens

<400> SEQUENCE: 217
tggggccctg gctgggatat catcatatac tgtaagtttg cgatgagaca ctacagtata    60
gatgatgtac tagtccgggc accccc                                         86

<210> SEQ ID NO 218
<211> LENGTH: 66
<212> TYPE: DNA
<213> ORGANISM: Homo sapiens

<400> SEQUENCE: 218
ggctgggata tcatcatata ctgtaagttt gcgatgagac actacagtat agatgatgta    60
ctagtc                                                               66

<210> SEQ ID NO 219
<211> LENGTH: 88
<212> TYPE: DNA
<213> ORGANISM: Homo sapiens

<400> SEQUENCE: 219
caccttgtcc tcacggtcca gttttcccag gaatccctta gatgctaaga tgggattcc     60 tggaaatact gttcttgagg tcatggtt                                       88

<210> SEQ ID NO 220
<211> LENGTH: 70
<212> TYPE: DNA
<213> ORGANISM: Homo sapiens

<400> SEQUENCE: 220
ctcacggtcc agttttccca ggaatccctt agatgctaag atggggattc ctggaaatac    60
tgttcttgag                                                           70

<210> SEQ ID NO 221
<211> LENGTH: 99
<212> TYPE: DNA
<213> ORGANISM: Homo sapiens

<400> SEQUENCE: 221
ccgatgtgta tcctcagctt tgagaactga attccatggg ttgtgtcagt gtcagacctc    60
tgaaattcag ttcttcagct gggatatctc tgtcatcgt                           99

<210> SEQ ID NO 222
<211> LENGTH: 65
<212> TYPE: DNA
<213> ORGANISM: Homo sapiens

<400> SEQUENCE: 222
agctttgaga actgaattcc atgggttgtg tcagtgtcag acctgtgaaa ttcagttctt    60
cagct                                                                65
```

```
<210> SEQ ID NO 223
<211> LENGTH: 72
<212> TYPE: DNA
<213> ORGANISM: Homo sapiens

<400> SEQUENCE: 223
aatctaaaga caacatttct gcacacacac cagactatgg aagccagtgt gtggaaatgc      60
ttctgctaga tt                                                         72

<210> SEQ ID NO 224
<211> LENGTH: 68
<212> TYPE: DNA
<213> ORGANISM: Homo sapiens

<400> SEQUENCE: 224
gaggcaaagt tctgagacac tccgactctg agtatgatag aagtcagtgc actacagaac     60
tttgtctc                                                              68

<210> SEQ ID NO 225
<211> LENGTH: 89
<212> TYPE: DNA
<213> ORGANISM: Homo sapiens

<400> SEQUENCE: 225
gccggcgccc gagctctggc tccgtgtctt cactcccgtg cttgtccgag gagggaggga     60
gggacggggg ctgtgctggg gcagctgga                                       89

<210> SEQ ID NO 226
<211> LENGTH: 53
<212> TYPE: DNA
<213> ORGANISM: Homo sapiens

<400> SEQUENCE: 226
gctctggctc cgtgtcttca ctcccgtgct tgtccgagga gggagggagg gac            53

<210> SEQ ID NO 227
<211> LENGTH: 84
<212> TYPE: DNA
<213> ORGANISM: Homo sapiens

<400> SEQUENCE: 227
ctccccatgg ccctgtctcc caaccttgt accagtgctg ggctcagacc ctggtacagg      60
cctgggggac agggacctgg ggac                                            84

<210> SEQ ID NO 228
<211> LENGTH: 64
<212> TYPE: DNA
<213> ORGANISM: Homo sapiens

<400> SEQUENCE: 228
ccctgtctcc caaccttgt accagtgctg ggctcagacc ctggtacagg cctgggggac      60
aggg                                                                  64

<210> SEQ ID NO 229
<211> LENGTH: 69
<212> TYPE: DNA
<213> ORGANISM: Homo sapiens

<400> SEQUENCE: 229
cctgccctcg aggagctcac agtctagtat gtctcatccc ctactagact gaagctcctt    60
```

```
gaggacagg                                                                     69

<210> SEQ ID NO 230
<211> LENGTH: 87
<212> TYPE: DNA
<213> ORGANISM: Homo sapiens

<400> SEQUENCE: 230 tgtcccccc ggcccaggtt ctgtgataca ctccgactcg ggctctggag cagtcagtgc              60
atgacagaac ttgggcccgg aaggacc                                                 87

<210> SEQ ID NO 231
<211> LENGTH: 71
<212> TYPE: DNA
<213> ORGANISM: Homo sapiens

<400> SEQUENCE: 231
ggcccaggtt ctgtgataca ctccgactcg ggctctggag cagtcagtgc atgacagaac             60
ttgggccccg g                                                                  71

<210> SEQ ID NO 232
<211> LENGTH: 90
<212> TYPE: DNA
<213> ORGANISM: Homo sapiens

<400> SEQUENCE: 232
ctcacagctg ccagtgtcat ttttgtgatc tgcagctagt attctcactc cagttgcata            60
gtcacaaaag tgatcattgg caggtgtggc                                              90

<210> SEQ ID NO 233
<211> LENGTH: 71
<212> TYPE: DNA
<213> ORGANISM: Homo sapiens

<400> SEQUENCE: 233
tctctctctc cctcacagct gccagtgtca ttgtcacaaa agtgatcatt ggcaggtgtg             60
gctgctgcat g                                                                  71

<210> SEQ ID NO 234
<211> LENGTH: 87
<212> TYPE: DNA
<213> ORGANISM: Homo sapiens

<400> SEQUENCE: 234
agcggtggcc agtgtcattt tgtgatgtt gcagctagta atatgagccc agttgcatag              60
tcacaaaagt gatcattgga aactgtg                                                 87

<210> SEQ ID NO 235
<211> LENGTH: 69
<212> TYPE: DNA
<213> ORGANISM: Homo sapiens

<400> SEQUENCE: 235
cagtgtcatt tttgtgatgt tgcagctagt aatatgagcc cagttgcata gtcacaaaag             60
tgatcattg                                                                     69

<210> SEQ ID NO 236
<211> LENGTH: 84
<212> TYPE: DNA
<213> ORGANISM: Homo sapiens
```

<400> SEQUENCE: 236
gtggtacttg aagataggtt atccgtgttg ccttcgcttt atttgtgacg aatcatacac    60
ggttgaccta tttttcagta ccaa                                          84

<210> SEQ ID NO 237
<211> LENGTH: 66
<212> TYPE: DNA
<213> ORGANISM: Homo sapiens

<400> SEQUENCE: 237
gaagataggt tatccgtgtt gccttcgctt tatttgtgac gaatcataca cggttgacct    60
attttt                                                              66

<210> SEQ ID NO 238
<211> LENGTH: 65
<212> TYPE: DNA
<213> ORGANISM: Homo sapiens

<400> SEQUENCE: 238
ctgttaatgc taatcgtgat aggggttttt gcctccaact gactcctaca tattagcatt    60
aacag                                                               65

<210> SEQ ID NO 239
<211> LENGTH: 108
<212> TYPE: DNA
<213> ORGANISM: Homo sapiens

<400> SEQUENCE: 239
caatgtcagc agtgccttag cagcacgtaa atattggcgt taagattcta aaattatctc    60
cagtattaac tgtgctgctg aagtaaggtt gaccatactc tacagttg               108

<210> SEQ ID NO 240
<211> LENGTH: 110
<212> TYPE: DNA
<213> ORGANISM: Homo sapiens

<400> SEQUENCE: 240
agaagggcta tcaggccagc cttcagagga ctccaaggaa cattcaacgc tgtcggtgag    60
tttgggattt gaaaaaacca ctgaccgttg actgtacctt ggggtcctta              110

<210> SEQ ID NO 241
<211> LENGTH: 110
<212> TYPE: DNA
<213> ORGANISM: Homo sapiens

<400> SEQUENCE: 241
tgagttttga ggttgcttca gtgaacattc aacgctgtcg gtgagtttgg aattaaaatc    60
aaaaccatcg accgttgatt gtaccctatg gctaaccatc atctactcca              110

<210> SEQ ID NO 242
<211> LENGTH: 110
<212> TYPE: DNA
<213> ORGANISM: Homo sapiens

<400> SEQUENCE: 242
cggaaaattt gccaagggtt tgggggaaca ttcaacctgt cggtgagttt ggcagctca     60 ggcaaaccat cgaccgttga gtggaccctg aggcctggaa ttgccatcct              110

<210> SEQ ID NO 243
<211> LENGTH: 110
<212> TYPE: DNA
<213> ORGANISM: Homo sapiens

<400> SEQUENCE: 243
gagctgcttg cctcccccg tttttggcaa tggtagaact cacactggtg aggtaacagg      60
atccggtggt tctagacttg ccaactatgg ggcgaggact cagccggcac              110

<210> SEQ ID NO 244
<211> LENGTH: 70
<212> TYPE: DNA
<213> ORGANISM: Homo sapiens

<400> SEQUENCE: 244
tttttggcaa tggtagaact cacactggtg aggtaacagg atccggtggt tctagacttg      60
ccaactatgg                                                            70

<210> SEQ ID NO 245
<211> LENGTH: 110
<212> TYPE: DNA
<213> ORGANISM: Homo sapiens

<400> SEQUENCE: 245
ccgcagagtg tgactcctgt tctgtgtatg gcactggtag aattcactgt gaacagtctc      60
agtcagtgaa ttaccgaagg gccataaaca gagcagagac agatccacga              110

<210> SEQ ID NO 246
<211> LENGTH: 84
<212> TYPE: DNA
<213> ORGANISM: Homo sapiens

<400> SEQUENCE: 246
ccagtcacgt cccttatca cttttccagc ccagctttgt gactgtaagt gttggacgga      60
gaactgataa gggtaggtga ttga                                           84

<210> SEQ ID NO 247
<211> LENGTH: 65
<212> TYPE: DNA
<213> ORGANISM: Homo sapiens

<400> SEQUENCE: 247
ccttatcact tttccagccc agctttgtga ctgtaagtgt tggacggaga actgataagg      60
gtagg                                                                65

<210> SEQ ID NO 248
<211> LENGTH: 82
<212> TYPE: DNA
<213> ORGANISM: Homo sapiens

<400> SEQUENCE: 248 aggggggcgag ggattggaga gaaaggcagt tcctgatggt cccctcccca ggggctggct      60
ttcctctggt ccttccctcc ca                                             82

<210> SEQ ID NO 249
<211> LENGTH: 66
<212> TYPE: DNA
<213> ORGANISM: Homo sapiens

<400> SEQUENCE: 249

```
agggattgga gagaaaggca gttcctgatg gtcccctccc caggggctgg cttttcctctg    60 gtccctt                                                               66

<210> SEQ ID NO 250
<211> LENGTH: 86
<212> TYPE: DNA
<213> ORGANISM: Homo sapiens

<400> SEQUENCE: 250
tgcttgtaac tttccaaaga attctccttt tgggctttct ggttttattt taagcccaaa    60
ggtgaatttt ttgggaagtt tgagct                                         86

<210> SEQ ID NO 251
<211> LENGTH: 71
<212> TYPE: DNA
<213> ORGANISM: Homo sapiens

<400> SEQUENCE: 251
actttccaaa gaattctcct tttgggcttt ctggttttat tttaagccca aaggtgaatt    60
ttttgggaag t                                                         71

<210> SEQ ID NO 252
<211> LENGTH: 109
<212> TYPE: DNA
<213> ORGANISM: Homo sapiens

<400> SEQUENCE: 252
ggtcgggctc accatgacac agtgtgagac tcgggctaca acacaggacc cggggcgctg    60
ctctgacccc tcgtgtcttg tgttgcagcc ggagggacgc aggtccgca              109

<210> SEQ ID NO 253
<211> LENGTH: 86
<212> TYPE: DNA
<213> ORGANISM: Homo sapiens

<400> SEQUENCE: 253
tgctccctct ctcacatccc ttgcatggtg gagggtgagc tttctgaaaa cccctcccac    60
atgcagggtt tgcaggatgg cgagcc                                         86

<210> SEQ ID NO 254
<211> LENGTH: 68
<212> TYPE: DNA
<213> ORGANISM: Homo sapiens

<400> SEQUENCE: 254
tctcacatcc cttgcatggt ggagggtgag ctttctgaaa accctccca catgcagggt    60 ttgcagga                                                             68

<210> SEQ ID NO 255
<211> LENGTH: 102
<212> TYPE: DNA
<213> ORGANISM: Homo sapiens

<400> SEQUENCE: 255
ctgtcgattg gacccgcccc ccggtgccta ctgagctgat atcagttctc attttacaca    60
ctggctcagt tcagcaggaa caggagtcga gcccttgagc aa                      102

<210> SEQ ID NO 256
```

```
<211> LENGTH: 68
<212> TYPE: DNA
<213> ORGANISM: Homo sapiens

<400> SEQUENCE: 256
ctccggtgcc tactgagctg atatcagttc tcattttaca cactggctca gttcagcagg      60
aacaggag                                                              68

<210> SEQ ID NO 257
<211> LENGTH: 85
<212> TYPE: DNA
<213> ORGANISM: Homo sapiens

<400> SEQUENCE: 257
tgcaggcctc tgtgtgatat gtttgatata ttaggttgtt atttaatcca actatatatc      60
aaacatattc ctacagtgtc ttgcc                                           85

<210> SEQ ID NO 258
<211> LENGTH: 67
<212> TYPE: DNA
<213> ORGANISM: Homo sapiens

<400> SEQUENCE: 258
ctgtgtgata tgtttgatat attaggttgt tatttaatcc aactatatat caaacatatt      60
cctacag                                                               67

<210> SEQ ID NO 259
<211> LENGTH: 92
<212> TYPE: DNA
<213> ORGANISM: Homo sapiens

<400> SEQUENCE: 259
cggctggaca gcgggcaacg gaatcccaaa agcagctgtt gtctccagag cattccagct      60
gcgcttggat ttcgtcccct gctctcctgc ct                                   92

<210> SEQ ID NO 260
<211> LENGTH: 74
<212> TYPE: DNA
<213> ORGANISM: Homo sapiens

<400> SEQUENCE: 260
agcgggcaac ggaatcccaa aagcagctgt tgtctccaga gcattccagc tgcgcttgga      60
tttcgtcccc tgct                                                       74

<210> SEQ ID NO 261
<211> LENGTH: 108
<212> TYPE: DNA
<213> ORGANISM: Homo sapiens

<400> SEQUENCE: 261
ccgagaccga gtgcacaggg ctctgaccta tgaattgaca gccagtgctc tcgtctcccc      60
tctggctgcc aattccatag gtcacaggta tgttcgcctc aatgccag                  108

<210> SEQ ID NO 262
<211> LENGTH: 110
<212> TYPE: DNA
<213> ORGANISM: Homo sapiens

<400> SEQUENCE: 262
gccgagaccg agtgcacagg gctctgacct atgaattgac agccagtgct ctcgtctccc      60
```
ctctggctgc caattccata ggtcacaggt atgttcgcct caatgccagc        110

<210> SEQ ID NO 263
<211> LENGTH: 88
<212> TYPE: DNA
<213> ORGANISM: Homo sapiens

<400> SEQUENCE: 263
cgaggatggg agctgagggc tgggtctttg cgggcgagat gagggtgtcg gatcaactgg        60
cctacaaagt cccagttctc ggcccccg        88

<210> SEQ ID NO 264
<211> LENGTH: 58
<212> TYPE: DNA
<213> ORGANISM: Homo sapiens

<400> SEQUENCE: 264
gctgggtctt tgcgggcgag atgagggtgt cggatcaact ggcctacaaa gtcccagt        58

<210> SEQ ID NO 265
<211> LENGTH: 85
<212> TYPE: DNA
<213> ORGANISM: Homo sapiens

<400> SEQUENCE: 265
atggtgttat caagtgtaac agcaactcca tgtggactgt gtaccaattt ccagtggaga        60
tgctgttact tttgatggtt accaa        85

<210> SEQ ID NO 266
<211> LENGTH: 63
<212> TYPE: DNA
<213> ORGANISM: Homo sapiens

<400> SEQUENCE: 266
gtgtaacagc aactccatgt ggactgtgta ccaatttcca gtggagatgc tgttactttt        60
gat        63

<210> SEQ ID NO 267
<211> LENGTH: 87
<212> TYPE: DNA
<213> ORGANISM: Homo sapiens

<400> SEQUENCE: 267
agcttccctg gctctagcag cacagaaata ttggcacagg aagcgagtc tgccaatatt        60 ggctgtgctg ctccaggcag ggtggtg        87

<210> SEQ ID NO 268
<211> LENGTH: 58
<212> TYPE: DNA
<213> ORGANISM: Homo sapiens

<400> SEQUENCE: 268
tagcagcaca gaaatattgg cacagggaag cgagtctgcc aatattggct gtgctgct        58

<210> SEQ ID NO 269
<211> LENGTH: 110
<212> TYPE: DNA
<213> ORGANISM: Homo sapiens

<400> SEQUENCE: 269

```
ctagagcttg aattggaact gctgagtgaa ttaggtagtt tcatgttgtt gggcctgggt    60
ttctgaacac aacaacatta aaccacccga ttcacggcag ttactgctcc              110
```

<210> SEQ ID NO 270
<211> LENGTH: 70
<212> TYPE: DNA
<213> ORGANISM: Homo sapiens

<400> SEQUENCE: 270

```
gtgaattagg tagtttcatg ttgttgggcc tgggtttctg aacacaacaa cattaaacca    60
cccgattcac                                                          70
```

<210> SEQ ID NO 271
<211> LENGTH: 110
<212> TYPE: DNA
<213> ORGANISM: Homo sapiens

<400> SEQUENCE: 271

```
tgctcgctca gctgatctgt ggcttaggta gtttcatgtt gttgggattg agttttgaac    60
tcggcaacaa gaaactgcct gagttacatc agtcggtttt cgtcgagggc              110
```

<210> SEQ ID NO 272
<211> LENGTH: 70
<212> TYPE: DNA
<213> ORGANISM: Homo sapiens

<400> SEQUENCE: 272

```
gtgaattagg tagtttcatg ttgttgggcc tgggtttctg aacacaacaa cattaaacca    60
cccgattcac                                                          70
```

<210> SEQ ID NO 273
<211> LENGTH: 75
<212> TYPE: DNA
<213> ORGANISM: Homo sapiens

<400> SEQUENCE: 273

```
ggctgtgccg ggtagagagg gcagtgggag gtaagagctc ttcacccttc accaccttct    60
ccacccagca tggcc                                                    75
```

<210> SEQ ID NO 274
<211> LENGTH: 62
<212> TYPE: DNA
<213> ORGANISM: Homo sapiens

<400> SEQUENCE: 274

```
tcattggtcc agagggagga taggttcctg tgattttttcc ttcttctcta tagaataaat   60
ga                                                                  62
```

<210> SEQ ID NO 275
<211> LENGTH: 71
<212> TYPE: DNA
<213> ORGANISM: Homo sapiens

<400> SEQUENCE: 275

```
gccaacccag tgttcagact acctgttcag gaggctctca atgtgtacag tagtctgcac    60
attggttagg c                                                        71
```

<210> SEQ ID NO 276
<211> LENGTH: 110

<212> TYPE: DNA
<213> ORGANISM: Homo sapiens

<400> SEQUENCE: 276
aggaagcttc tggagatcct gctccgtcgc cccagtgttc agactacctg ttcaggacaa    60
tgccgttgta cagtagtctg cacattggtt agactgggca agggagagca               110

<210> SEQ ID NO 277
<211> LENGTH: 110
<212> TYPE: DNA
<213> ORGANISM: Homo sapiens

<400> SEQUENCE: 277
ccagaggaca cctccactcc gtctacccag tgtttagact atctgttcag gactcccaaa    60
ttgtacagta gtctgcacat tggttaggct gggctgggtt agaccctcgg               110

<210> SEQ ID NO 278
<211> LENGTH: 71
<212> TYPE: DNA
<213> ORGANISM: Homo sapiens

<400> SEQUENCE: 278
gccaacccag tgttcagact acctgttcag gaggctctca atgtgtacag tagtctgcac    60
attggttagg c                                                         71

<210> SEQ ID NO 279
<211> LENGTH: 70
<212> TYPE: DNA
<213> ORGANISM: Homo sapiens

<400> SEQUENCE: 279
gccgtggcca tcttactggg cagcattgga tggagtcagg tctctaatac tgcctggtaa    60
tgatgacggc                                                           70

<210> SEQ ID NO 280
<211> LENGTH: 95
<212> TYPE: DNA
<213> ORGANISM: Homo sapiens

<400> SEQUENCE: 280
ccagctcggg cagccgtggc catcttactg ggcagcattg gatggagtca ggtctctaat    60
actgcctggt aatgatgacg gcggagccct gcacg                               95

<210> SEQ ID NO 281
<211> LENGTH: 72
<212> TYPE: DNA
<213> ORGANISM: Homo sapiens

<400> SEQUENCE: 281
gttccttttt cctatgcata tacttctttg aggatctggc ctaaagaggt atagggcatg    60
ggaagatgga gc                                                        72

<210> SEQ ID NO 282
<211> LENGTH: 110
<212> TYPE: DNA
<213> ORGANISM: Homo sapiens

<400> SEQUENCE: 282
gtgttgggga ctcgcgcgct gggtccagtg gttcttaaca gttcaacagt tctgtagcgc    60

```
aattgtgaaa tgtttaggac cactagaccc ggcgggcgcg gcgacagcga              110
```

<210> SEQ ID NO 283
<211> LENGTH: 110
<212> TYPE: DNA
<213> ORGANISM: Homo sapiens

<400> SEQUENCE: 283

```
ggctacagtc tttcttcatg tgactcgtgg acttcccttt gtcatcctat gcctgagaat    60
atatgaagga ggctgggaag gcaaagggac gttcaattgt catcactggc              110
```

<210> SEQ ID NO 284
<211> LENGTH: 110
<212> TYPE: DNA
<213> ORGANISM: Homo sapiens

<400> SEQUENCE: 284

```
aaagatcctc agacaatcca tgtgcttctc ttgtccttca ttccaccgga gtctgtctca    60
tacccaacca gatttcagtg gagtgaagtt caggaggcat ggagctgaca              110
```

<210> SEQ ID NO 285
<211> LENGTH: 86
<212> TYPE: DNA
<213> ORGANISM: Homo sapiens

<400> SEQUENCE: 285

```
tgcttcccga ggccacatgc ttctttatat ccccatatgg attactttgc tatggaatgt    60
aaggaagtgt gtggtttcgg caagtg                                         86
```

<210> SEQ ID NO 286
<211> LENGTH: 69
<212> TYPE: DNA
<213> ORGANISM: Homo sapiens

<400> SEQUENCE: 286

```
aggccacatg cttctttata tccccatatg gattactttg ctatggaatg taaggaagtg    60
tgtggtttt                                                            69
```

<210> SEQ ID NO 287
<211> LENGTH: 71
<212> TYPE: DNA
<213> ORGANISM: Homo sapiens

<400> SEQUENCE: 287

```
tgacgggcga gcttttggcc cgggttatac ctgatgctca cgtataagac gagcaaaaag    60
cttgttggtc a                                                         71
```

<210> SEQ ID NO 288
<211> LENGTH: 110
<212> TYPE: DNA
<213> ORGANISM: Homo sapiens

<400> SEQUENCE: 288

```
acccggcagt gcctccaggc gcagggcagc ccctgcccac cgcacactgc gctgccccag    60
acccactgtg cgtgtgacag cggctgatct gtgcctgggc agcgcgaccc              110
```

<210> SEQ ID NO 289
<211> LENGTH: 110
<212> TYPE: DNA
<213> ORGANISM: Homo sapiens

```
<400> SEQUENCE: 289
tcacctggcc atgtgacttg tgggcttccc tttgtcatcc ttcgcctagg gctctgagca       60
gggcagggac agcaaagggg tgctcagttg tcacttccca cagcacggag                110

<210> SEQ ID NO 290
<211> LENGTH: 110
<212> TYPE: DNA
<213> ORGANISM: Homo sapiens

<400> SEQUENCE: 290
cggggcaccc cgcccggaca gcgcgccggc accttggctc tagactgctt actgcccggg       60
ccgccctcag taacagtctc cagtcacggc caccgacgcc tggccccgcc                110

<210> SEQ ID NO 291
<211> LENGTH: 110
<212> TYPE: DNA
<213> ORGANISM: Homo sapiens

<400> SEQUENCE: 291
cctgtgcaga gattattttt taaaaggtca caatcaacat tcattgctgt cggtgggttg       60
aactgtgtgg acaagctcac tgaacaatga atgcaactgt ggccccgctt                110

<210> SEQ ID NO 292
<211> LENGTH: 108
<212> TYPE: DNA
<213> ORGANISM: Homo sapiens

<400> SEQUENCE: 292
gagttttgag gttgcttcag tgaacattca acgctgtcgg tgagtttgga attaaaatca       60
aaaccatcga ccgttgattg taccctatgg ctaaccatca tctactcc                   108

<210> SEQ ID NO 293
<211> LENGTH: 110
<212> TYPE: DNA
<213> ORGANISM: Homo sapiens

<400> SEQUENCE: 293
ggcctggctg gacagagttg tcatgtgtct gcctgtctac acttgctgtg cagaacatcc       60
gctcacctgt acagcaggca cagacaggca gtcacatgac aacccagcct                110

<210> SEQ ID NO 294
<211> LENGTH: 110
<212> TYPE: DNA
<213> ORGANISM: Homo sapiens

<400> SEQUENCE: 294
atcattcaga aatggtatac aggaaaatga cctatgaatt gacagacaat atagctgagt       60
ttgtctgtca tttctttagg ccaatattct gtatgactgt gctacttcaa                110

<210> SEQ ID NO 295
<211> LENGTH: 110
<212> TYPE: DNA
<213> ORGANISM: Homo sapiens

<400> SEQUENCE: 295
gatggctgtg agttggctta atctcagctg gcaactgtga gatgttcata caatccctca       60
cagtggtctc tgggattatg ctaaacagag caatttccta gccctcacga                110
```

<210> SEQ ID NO 296
<211> LENGTH: 110
<212> TYPE: DNA
<213> ORGANISM: Homo sapiens

<400> SEQUENCE: 296
agtataatta ttacatagtt tttgatgtcg cagatactgc atcaggaact gattggataa    60
gaatcagtca ccatcagttc ctaatgcatt gccttcagca tctaaacaag              110

<210> SEQ ID NO 297
<211> LENGTH: 110
<212> TYPE: DNA
<213> ORGANISM: Homo sapiens

<400> SEQUENCE: 297
gtgataatgt agcgagattt tctgttgtgc ttgatctaac catgtggttg cgaggtatga    60
gtaaaacatg gttccgtcaa gcaccatgga acgtcacgca gctttctaca              110

<210> SEQ ID NO 298
<211> LENGTH: 110
<212> TYPE: DNA
<213> ORGANISM: Homo sapiens

<400> SEQUENCE: 298
gaccagtcgc tgcggggctt tcctttgtgc ttgatctaac catgtggtgg aacgatggaa    60
acggaacatg gttctgtcaa gcaccgcgga aagcaccgtg ctctcctgca              110

<210> SEQ ID NO 299
<211> LENGTH: 110
<212> TYPE: DNA
<213> ORGANISM: Homo sapiens

<400> SEQUENCE: 299
ccgccccggg ccgcggctcc tgattgtcca aacgcaattc tcgagtctat ggctccggcc    60
gagagttgag tctggacgtc ccgagccgcc gcccccaaac ctcgagcggg              110

<210> SEQ ID NO 300
<211> LENGTH: 110
<212> TYPE: DNA
<213> ORGANISM: Homo sapiens

<400> SEQUENCE: 300
gacagtgtgg cattgtaggg ctccacaccg tatctgacac tttgggcgag ggcaccatgc    60
tgaaggtgtt catgatgcgg tctgggaact cctcacggat cttactgatg              110

<210> SEQ ID NO 301
<211> LENGTH: 110
<212> TYPE: DNA
<213> ORGANISM: Homo sapiens

<400> SEQUENCE: 301
tgaacatcca ggtctggggc atgaacctgg catacaatgt agatttctgt gttcgttagg    60
caacagctac attgtctgct gggtttcagg ctacctggaa acatgttctc              110

<210> SEQ ID NO 302
<211> LENGTH: 110
<212> TYPE: DNA
<213> ORGANISM: Homo sapiens

<400> SEQUENCE: 302
gctgctggaa ggtgtaggta ccctcaatgg ctcagtagcc agtgtagatc ctgtctttcg    60
taatcagcag ctacatctgg ctactgggtc tctgatggca tcttctagct               110

<210> SEQ ID NO 303
<211> LENGTH: 110
<212> TYPE: DNA
<213> ORGANISM: Homo sapiens

<400> SEQUENCE: 303
cctggcctcc tgcagtgcca cgctccgtgt atttgacaag ctgagttgga cactccatgt    60
ggtagagtgt cagtttgtca aatacccaa gtgcggcaca tgcttaccag                110

<210> SEQ ID NO 304
<211> LENGTH: 81
<212> TYPE: DNA
<213> ORGANISM: Homo sapiens

<400> SEQUENCE: 304
gggctttcaa gtcactagtg gttccgttta gtagatgatt gtgcattgtt tcaaaatggt    60
gccctagtga ctacaaagcc c                                              81

<210> SEQ ID NO 305
<211> LENGTH: 81
<212> TYPE: DNA
<213> ORGANISM: Homo sapiens

<400> SEQUENCE: 305
cttctggaag ctggtttcac atggtggctt agattttttcc atctttgtat ctagcaccat    60
ttgaaatcag tgttttagga g                                              81

<210> SEQ ID NO 306
<211> LENGTH: 81
<212> TYPE: DNA
<213> ORGANISM: Homo sapiens

<400> SEQUENCE: 306
cttcaggaag ctggttttcat atggtggttt agatttaaat agtgattgtc tagcaccatt    60
tgaaatcagt gttcttgggg g                                              81

<210> SEQ ID NO 307
<211> LENGTH: 80
<212> TYPE: DNA
<213> ORGANISM: Homo sapiens

<400> SEQUENCE: 307
gtgagcgact gtaaacatcc tcgactggaa gctgtgaagc cacagatggg ctttcagtcg    60
gatgtttgca gctgcctact                                                80

<210> SEQ ID NO 308
<211> LENGTH: 88
<212> TYPE: DNA
<213> ORGANISM: Homo sapiens

<400> SEQUENCE: 308
accaagtttc agttcatgta aacatcctac actcagctgt aatacatgga ttggctggga    60
ggtggatgtt tacttcagct gacttgga                                       88

<210> SEQ ID NO 309

```
<211> LENGTH: 75
<212> TYPE: DNA
<213> ORGANISM: Homo sapiens

<400> SEQUENCE: 309
tgccctggct cagttatcac agtgctgatg ctgtctattc taaaggtaca gtactgtgat    60
aactgaagga tggca                                                    75

<210> SEQ ID NO 310
<211> LENGTH: 90
<212> TYPE: DNA
<213> ORGANISM: Homo sapiens

<400> SEQUENCE: 310
acactgcaag aacaataagg attttaggg gcattatgac tgagtcagaa aacacagctg    60
cccctgaaag tccctcattt ttcttgctgt                                    90

<210> SEQ ID NO 311
<211> LENGTH: 80
<212> TYPE: DNA
<213> ORGANISM: Homo sapiens

<400> SEQUENCE: 311
actgcaagag caataaggat ttttaggggc attatgatag tggaatggaa acacatctgc    60
ccccaaaagt ccctcatttt                                               80

<210> SEQ ID NO 312
<211> LENGTH: 85
<212> TYPE: DNA
<213> ORGANISM: Homo sapiens

<400> SEQUENCE: 312
cgctggcgac gggacattat tacttttggt acgcgctgtg acacttcaaa ctcgtaccgt    60
gagtaataat gcgccgtcca cggca                                         85

<210> SEQ ID NO 313
<211> LENGTH: 61
<212> TYPE: DNA
<213> ORGANISM: Homo sapiens

<400> SEQUENCE: 313
acattattac ttttggtacg cgctgtgaca cttcaaactc gtaccgtgag taataatgcg    60
c                                                                   61

<210> SEQ ID NO 314
<211> LENGTH: 74
<212> TYPE: DNA
<213> ORGANISM: Homo sapiens

<400> SEQUENCE: 314
tggatctttt tgcggtctgg gcttgctgtt cctctcaaca gtagtcagga agcccttacc    60
ccaaaaagta tcta                                                     74

<210> SEQ ID NO 315
<211> LENGTH: 90
<212> TYPE: DNA
<213> ORGANISM: Homo sapiens

<400> SEQUENCE: 315
tgcccttcgc gaatcttttt gcggtctggg cttgctgtac ataactcaat agccggaagc    60
```

-continued

```
ccttacccca aaaagcattt gcggagggcg                                           90
```

<210> SEQ ID NO 316
<211> LENGTH: 80
<212> TYPE: DNA
<213> ORGANISM: Homo sapiens

<400> SEQUENCE: 316

```
gcccctgct ctggctggtc aaacggaacc aagtccgtct tcctgagagg tttggtcccc          60
ttcaaccagc tacagcaggg                                                      80
```

<210> SEQ ID NO 317
<211> LENGTH: 100
<212> TYPE: DNA
<213> ORGANISM: Homo sapiens

<400> SEQUENCE: 317

```
agataaattc actctagtgc tttatggctt tttattccta tgtgatagta ataaagtctc          60
atgtagggat ggaagccatg aaatacattg tgaaaaatca                               100
```

<210> SEQ ID NO 318
<211> LENGTH: 70
<212> TYPE: DNA
<213> ORGANISM: Homo sapiens

<400> SEQUENCE: 318

```
aagcacgatt agcatttgag gtgaagttct gttatacact caggctgtgg ctctctgaaa         60
gtcagtgcat                                                                70
```

<210> SEQ ID NO 319
<211> LENGTH: 69
<212> TYPE: DNA
<213> ORGANISM: Homo sapiens

<400> SEQUENCE: 319

```
cctgtcctca aggagcttca gtctagtagg ggatgagaca tactagactg tgagctcctc         60
gagggcagg                                                                 69
```

<210> SEQ ID NO 320
<211> LENGTH: 65
<212> TYPE: DNA
<213> ORGANISM: Homo sapiens

<400> SEQUENCE: 320

```
ctgttaatgc taatcgtgat aggggttttt gcctccaact gactcctaca tattagcatt         60
aacag                                                                     65
```

<210> SEQ ID NO 321
<211> LENGTH: 82
<212> TYPE: DNA
<213> ORGANISM: Homo sapiens

<400> SEQUENCE: 321

```
cctaacactg tctggtaaag atggctcccg ggtgggttct ctcggcagta accttcaggg         60
agccctgaag accatggagg ac                                                  82
```

<210> SEQ ID NO 322
<211> LENGTH: 110
<212> TYPE: DNA

<213> ORGANISM: Homo sapiens

<400> SEQUENCE: 322

| gccgagaccg agtgcacagg gctctgacct atgaattgac agccagtgct ctcgtctccc | 60 |
| ctctggctgc caattccata ggtcacaggt atgttcgcct caatgccagc | 110 |

<210> SEQ ID NO 323
<211> LENGTH: 80
<212> TYPE: DNA
<213> ORGANISM: Homo sapiens

<400> SEQUENCE: 323

| tcccgccccc tgtaacagca actccatgtg gaagtgccca ctggttccag tggggctgct | 60 |
| gttatctggg gcgagggcca | 80 |

<210> SEQ ID NO 324
<211> LENGTH: 70
<212> TYPE: DNA
<213> ORGANISM: Homo sapiens

<400> SEQUENCE: 324

| aaagctgggt tgagagggcg aaaaaggatg aggtgactgg tctgggctac gctatgctgc | 60 |
| ggcgctcggg | 70 |

<210> SEQ ID NO 325
<211> LENGTH: 64
<212> TYPE: DNA
<213> ORGANISM: Homo sapiens

<400> SEQUENCE: 325

| cattggcctc ctaagccagg gattgtgggt tcgagtccca cccggggtaa agaaaggccg | 60 |
| aatt | 64 |

<210> SEQ ID NO 326
<211> LENGTH: 70
<212> TYPE: DNA
<213> ORGANISM: Homo sapiens

<400> SEQUENCE: 326

| cctaagccag ggattgtggg ttcgagtccc acctggggta gaggtgaaag ttcctttttac | 60 |
| ggaattttt | 70 |

<210> SEQ ID NO 327
<211> LENGTH: 81
<212> TYPE: DNA
<213> ORGANISM: Homo sapiens

<400> SEQUENCE: 327

| gggcttttcaa gtcactagtg gttccgttta gtagatgatt gtgcattgtt tcaaaatggt | 60 |
| gccctagtga ctacaaagcc c | 81 |

<210> SEQ ID NO 328
<211> LENGTH: 70
<212> TYPE: DNA
<213> ORGANISM: Homo sapiens

<400> SEQUENCE: 328

| acgcaagtgt cctaaggtga gctcagggag cacagaaacc tccagtggaa cagaagggca | 60 |
| aaagctcatt | 70 |

<210> SEQ ID NO 329
<211> LENGTH: 70
<212> TYPE: DNA
<213> ORGANISM: Homo sapiens

<400> SEQUENCE: 329
catgtgtcac tttcaggtgg agtttcaaga gtcccttcct ggttcaccgt ctcctttgct    60
cttccacaac                                                          70

<210> SEQ ID NO 330
<211> LENGTH: 109
<212> TYPE: DNA
<213> ORGANISM: Homo sapiens

<400> SEQUENCE: 330
ggtcgggctc accatgacac agtgtgagac tcgggctaca acacaggacc cggggcgctg    60
ctctgacccc tcgtgtcttg tgttgcagcc ggagggacgc aggtccgca               109

<210> SEQ ID NO 331
<211> LENGTH: 86
<212> TYPE: DNA
<213> ORGANISM: Homo sapiens

<400> SEQUENCE: 331
tgctccctct ctcacatccc ttgcatggtg gagggtgagc tttctgaaaa ccctcccac     60 atgcagggtt tgcaggatgg cgagcc                                        86

<210> SEQ ID NO 332
<211> LENGTH: 85
<212> TYPE: DNA
<213> ORGANISM: Homo sapiens

<400> SEQUENCE: 332
tgcaggcctc tgtgtgatat gtttgatata ttaggttgtt atttaatcca actatatatc    60
aaacatattc ctacagtgtc ttgcc                                         85

<210> SEQ ID NO 333
<211> LENGTH: 60
<212> TYPE: DNA
<213> ORGANISM: Homo sapiens

<400> SEQUENCE: 333
gtgcatgtgt atgtatgtgt gcatgtgcat gtgtatgtgt atgagtgcat gcgtgtgtgc    60

<210> SEQ ID NO 334
<211> LENGTH: 75
<212> TYPE: DNA
<213> ORGANISM: Homo sapiens

<400> SEQUENCE: 334
ggctgtgccg ggtagagagg gcagtgggag gtaagagctc ttcacccttc accaccttct    60
ccacccagca tggcc                                                    75

<210> SEQ ID NO 335
<211> LENGTH: 72
<212> TYPE: DNA
<213> ORGANISM: Homo sapiens

<400> SEQUENCE: 335

```
gttccttttt cctatgcata tacttctttg aggatctggc ctaaagaggt atagggcatg    60
ggaagatgga gc                                                       72

<210> SEQ ID NO 336
<211> LENGTH: 60
<212> TYPE: DNA
<213> ORGANISM: Homo sapiens

<400> SEQUENCE: 336
caatcttcct ttatcatggt attgattttt cagtgcttcc cttttgtgtg agagaagata    60

<210> SEQ ID NO 337
<211> LENGTH: 102
<212> TYPE: DNA
<213> ORGANISM: Homo sapiens

<400> SEQUENCE: 337
atggagctgc tcaccctgtg ggcctcaaat gtggaggaac tattctgatg tccaagtgga    60
aagtgctgcg acatttgagc gtcaccggtg acgcccatat ca                      102

<210> SEQ ID NO 338
<211> LENGTH: 101
<212> TYPE: DNA
<213> ORGANISM: Homo sapiens

<400> SEQUENCE: 338
gcatcccctc agcctgtggc actcaaactg tgggggcact ttctgctctc tggtgaaagt    60
gccgccatct tttgagtgtt accgcttgag aagactcaac c                       101

<210> SEQ ID NO 339
<211> LENGTH: 102
<212> TYPE: DNA
<213> ORGANISM: Homo sapiens

<400> SEQUENCE: 339
cgaggagctc atactgggat actcaaaatg ggggcgcttt ccttttttgtc tgttactggg   60 aagtgcttcg attttggggt gtccctgttt gagtagggca tc                      102

<210> SEQ ID NO 340
<211> LENGTH: 81
<212> TYPE: DNA
<213> ORGANISM: Homo sapiens

<400> SEQUENCE: 340
cttcaggaag ctggtttcat atggtggttt agatttaaat agtgattgtc tagcaccatt    60
tgaaatcagt gttcttgggg g                                             81

<210> SEQ ID NO 341
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 341
uagcagcacg uaaauauugg cg                                            22

<210> SEQ ID NO 342
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      primer

<400> SEQUENCE: 342
uagcagcaca uaaugguuug ug                                                  22

<210> SEQ ID NO 343
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
ctagtctaga gcctcaggga acagaatgat cag                                      33

<210> SEQ ID NO 344
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
ctagtctaga aagcgtccac gttcttcatt g                                        31
```